US010569052B2

(12) United States Patent
Kokish et al.

(10) Patent No.: US 10,569,052 B2
(45) Date of Patent: Feb. 25, 2020

(54) ANTI-BUCKLING MECHANISMS FOR CATHETERS

(71) Applicant: Auris Health, Inc., Redwood City, CA (US)

(72) Inventors: Arkady Kokish, Los Gatos, CA (US); Kent Stalker, San Marcos, CA (US); Jason J. Hsu, Mountain View, CA (US)

(73) Assignee: Auris Health, Inc., Redwood City, CA (US)

( * ) Notice: Subject to any disclaimer, the term of this patent is extended or adjusted under 35 U.S.C. 154(b) by 689 days.

(21) Appl. No.: 14/713,895

(22) Filed: May 15, 2015

(65) Prior Publication Data
US 2015/0327939 A1 Nov. 19, 2015

Related U.S. Application Data

(60) Provisional application No. 61/993,370, filed on May 15, 2014, provisional application No. 62/014,189, (Continued)

(51) Int. Cl.
*A61M 25/01* (2006.01)
*F16L 3/12* (2006.01)
*A61B 34/30* (2016.01)

(52) U.S. Cl.
CPC ......... *A61M 25/0102* (2013.01); *A61B 34/30* (2016.02); *F16L 3/1222* (2013.01)

(58) Field of Classification Search
CPC ..................... A61M 25/0102; A61B 8/4218
See application file for complete search history.

(56) References Cited

U.S. PATENT DOCUMENTS 2,556,601 A 6/1951 Schofield
2,566,183 A 8/1951 Forss
(Continued)

FOREIGN PATENT DOCUMENTS

CN 101500470 8/2009
CN 102665590 9/2012
(Continued)

OTHER PUBLICATIONS

"Speciality Guidewires," http://www.galtmedical.com/pdf/Guidewires.pdf, retrieved on Jun. 18, 2014 (2 pages).
(Continued)

*Primary Examiner* — Bhisma Mehta
*Assistant Examiner* — Matthew A Engel
(74) *Attorney, Agent, or Firm* — Knobbe, Martens, Olson & Bear LLP

(57) ABSTRACT

A device is provided for preventing buckling of a flexible elongate member during insertion of the flexible elongate member. The device includes a support frame comprising a first end, a second end, and multiple pairs of support members. The support frame is configured to reversibly move from a collapsed configuration to an expanded configuration when the first and second ends are moved away from each other. The device also includes multiple open channels coupled to the multiple pairs of support members of the support frame. The multiple open channels are configured to allow the flexible elongate member to be top loaded into the multiple open channels. Also, the multiple open channels are maintained in an axial alignment as the support frame is moved between the expanded and collapsed configurations.

12 Claims, 36 Drawing Sheets

Related U.S. Application Data filed on Jun. 19, 2014, provisional application No. 62/057,356, filed on Sep. 30, 2014.

(56) References Cited

U.S. PATENT DOCUMENTS

| | | |
|---|---|---|
| 2,730,699 A | 1/1956 | Gratian |
| 2,884,808 A | 5/1959 | Mueller |
| 3,294,183 A | 12/1966 | Riley et al. |
| 3,472,083 A | 10/1969 | Schnepel |
| 3,513,724 A | 5/1970 | Box |
| 3,595,074 A | 7/1971 | Johnson |
| 3,734,207 A | 5/1973 | Fishbein |
| 4,141,245 A | 2/1979 | Brandstetter |
| 4,241,884 A | 12/1980 | Lynch |
| 4,243,034 A | 1/1981 | Brandt |
| 4,351,493 A | 9/1982 | Sonnek |
| 4,357,843 A | 11/1982 | Peck et al. |
| 4,384,493 A | 5/1983 | Grunbaum |
| 4,507,026 A | 3/1985 | Lund |
| 4,530,471 A | 7/1985 | Inoue |
| 4,555,960 A | 12/1985 | King |
| 4,688,555 A | 8/1987 | Wardle |
| 4,745,908 A | 5/1988 | Wardle |
| 4,784,150 A | 11/1988 | Voorhies et al. |
| 4,857,058 A * | 8/1989 | Payton .................. A61M 25/02 604/180 |
| 4,907,168 A | 3/1990 | Boggs |
| 4,945,790 A | 8/1990 | Golden |
| 5,207,128 A | 5/1993 | Albright |
| 5,234,428 A | 8/1993 | Kaufman |
| 5,256,150 A | 10/1993 | Quiachon et al. |
| 5,277,085 A | 1/1994 | Tanimura et al. |
| 5,350,101 A | 9/1994 | Godlewski |
| 5,426,687 A | 6/1995 | Goodall et al. |
| 5,507,725 A | 4/1996 | Savage et al. |
| 5,559,294 A | 9/1996 | Hoium et al. |
| 5,767,840 A | 6/1998 | Selker |
| 5,779,623 A | 7/1998 | Bonnell |
| 5,792,135 A | 8/1998 | Madhani et al. |
| 5,855,583 A | 1/1999 | Wang et al. |
| 5,921,968 A | 7/1999 | Lampropoulos et al. |
| 5,967,934 A | 10/1999 | Ishida et al. |
| 6,084,371 A | 7/2000 | Kress et al. |
| 6,096,004 A | 8/2000 | Meglan et al. |
| 6,154,000 A | 11/2000 | Rastegar et al. |
| 6,171,234 B1 | 1/2001 | White et al. |
| 6,185,478 B1 | 2/2001 | Koakutsu et al. |
| 6,272,371 B1 | 8/2001 | Shlomo |
| 6,289,579 B1 * | 9/2001 | Viza ...................... B65G 47/26 29/739 |
| 6,394,998 B1 | 5/2002 | Wallace et al. |
| 6,401,572 B1 | 6/2002 | Provost |
| 6,436,107 B1 | 8/2002 | Wang et al. |
| 6,487,940 B2 | 12/2002 | Hart et al. |
| 6,491,701 B2 | 12/2002 | Tierney et al. |
| 6,695,818 B2 | 2/2004 | Wollschlager |
| 6,726,675 B1 | 4/2004 | Beyar |
| 6,786,896 B1 | 9/2004 | Madhani et al. |
| 6,827,712 B2 | 12/2004 | Tovey et al. |
| 7,044,936 B2 | 5/2006 | Harding |
| 7,172,580 B2 | 2/2007 | Hruska et al. |
| 7,276,044 B2 | 10/2007 | Ferry et al. |
| 7,615,042 B2 | 11/2009 | Beyar et al. |
| 7,635,342 B2 | 12/2009 | Ferry et al. |
| 7,766,856 B2 | 8/2010 | Ferry et al. |
| 7,938,809 B2 | 5/2011 | Lampropoulos et al. |
| 7,974,674 B2 * | 7/2011 | Hauck .................. A61B 5/6885 600/374 |
| 7,998,020 B2 | 8/2011 | Kidd et al. |
| 8,052,621 B2 | 11/2011 | Wallace et al. |
| 8,052,636 B2 | 11/2011 | Moll et al. |
| 8,092,397 B2 | 1/2012 | Wallace et al. |
| 8,157,308 B2 | 4/2012 | Pedersen |
| 8,182,415 B2 | 5/2012 | Larkin et al. |
| 8,291,791 B2 | 10/2012 | Light et al. |
| 8,746,252 B2 | 6/2014 | McGrogan et al. |
| 8,894,610 B2 | 11/2014 | MacNamara et al. |
| 8,961,533 B2 * | 2/2015 | Stahler .................... A61B 6/12 606/108 |
| 9,014,851 B2 | 4/2015 | Wong et al. |
| 9,138,166 B2 | 9/2015 | Wong et al. |
| 9,173,713 B2 | 11/2015 | Hart et al. |
| 9,204,933 B2 | 12/2015 | Reis et al. |
| 9,326,822 B2 | 5/2016 | Lewis et al. |
| 9,408,669 B2 | 8/2016 | Kokish et al. |
| 9,452,018 B2 | 9/2016 | Yu |
| 9,457,168 B2 | 10/2016 | Moll et al. |
| 9,498,601 B2 | 11/2016 | Tanner et al. |
| 9,504,604 B2 | 11/2016 | Alvarez |
| 9,561,083 B2 | 2/2017 | Yu et al. |
| 9,622,827 B2 | 4/2017 | Yu et al. |
| 9,636,184 B2 | 5/2017 | Lee et al. |
| 9,636,483 B2 | 5/2017 | Hart et al. |
| 9,668,814 B2 | 6/2017 | Kokish |
| 9,710,921 B2 | 7/2017 | Wong et al. |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 2001/0042643 A1 | 11/2001 | Krueger et al. |
| 2002/0045905 A1 | 4/2002 | Gerbi et al. |
| 2002/0098938 A1 | 7/2002 | Milbourne et al. |
| 2002/0117017 A1 | 8/2002 | Bernhardt et al. |
| 2002/0161355 A1 | 10/2002 | Wollschlager |
| 2002/0161426 A1 * | 10/2002 | Iancea .................... A61F 2/958 623/1.11 |
| 2002/0177789 A1 | 11/2002 | Ferry et al. |
| 2004/0015053 A1 | 1/2004 | Bieger |
| 2004/0152972 A1 | 8/2004 | Hunter |
| 2004/0243147 A1 | 12/2004 | Lipow |
| 2005/0183532 A1 | 8/2005 | Najaf et al. |
| 2005/0222554 A1 | 10/2005 | Wallace et al. |
| 2006/0111692 A1 | 5/2006 | Hlavka et al. |
| 2006/0201688 A1 | 9/2006 | Jenner et al. |
| 2006/0224162 A1 | 10/2006 | Suzuki et al. |
| 2006/0237205 A1 | 10/2006 | Sia et al. |
| 2007/0000498 A1 | 1/2007 | Glynn et al. |
| 2007/0013336 A1 | 1/2007 | Nowlin et al. |
| 2007/0060879 A1 | 3/2007 | Weitzner et al. |
| 2007/0112355 A1 | 5/2007 | Salahieh |
| 2007/0149946 A1 | 6/2007 | Viswanathan |
| 2007/0191177 A1 | 8/2007 | Nagai et al. |
| 2007/0245175 A1 | 10/2007 | Zheng et al. |
| 2007/0299427 A1 | 12/2007 | Yeung et al. |
| 2008/0039255 A1 | 2/2008 | Jinno et al. |
| 2008/0046122 A1 | 2/2008 | Manzo et al. |
| 2008/0065103 A1 | 3/2008 | Cooper et al. |
| 2008/0140087 A1 | 6/2008 | Barbagli et al. |
| 2008/0147011 A1 | 6/2008 | Urmey |
| 2008/0177285 A1 | 7/2008 | Brock et al. |
| 2008/0214925 A1 | 9/2008 | Wilson et al. |
| 2008/0243064 A1 | 10/2008 | Stahler |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0302200 A1 | 12/2008 | Tobey |
| 2009/0082722 A1 | 3/2009 | Munger et al. |
| 2009/0098971 A1 | 4/2009 | Ho et al. |
| 2009/0247944 A1 | 10/2009 | Kirschenman et al. |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0130987 A1 | 5/2010 | Wenderow et al. |

(56) References Cited

U.S. PATENT DOCUMENTS

| | | |
|---|---|---|
| 2010/0204646 A1 | 8/2010 | Plicchi et al. |
| 2010/0210923 A1 | 8/2010 | Li et al. |
| 2010/0248177 A1 | 9/2010 | Mangelberger et al. |
| 2011/0015484 A1 | 1/2011 | Alvarez et al. |
| 2011/0015648 A1 | 1/2011 | Alvarez et al. |
| 2011/0028991 A1 | 2/2011 | Ikeda et al. |
| 2011/0130718 A1* | 6/2011 | Kidd ............ A61M 25/0105 604/95.01 |
| 2011/0147030 A1 | 6/2011 | Blum et al. |
| 2011/0238083 A1 | 9/2011 | Moll et al. |
| 2011/0261183 A1 | 10/2011 | Ma et al. |
| 2011/0277775 A1 | 11/2011 | Holop et al. |
| 2011/0288573 A1 | 11/2011 | Yates et al. |
| 2011/0306836 A1 | 12/2011 | Ohline et al. |
| 2012/0071821 A1 | 3/2012 | Yu |
| 2012/0071894 A1* | 3/2012 | Tanner ............ A61B 6/12 606/130 |
| 2012/0071895 A1* | 3/2012 | Stahler ............ A61B 6/12 606/130 |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0191107 A1* | 7/2012 | Tanner ............ A61B 6/12 606/130 |
| 2012/0239012 A1 | 9/2012 | Laurent et al. |
| 2012/0283747 A1 | 11/2012 | Popovic |
| 2013/0018400 A1 | 1/2013 | Milton et al. |
| 2013/0030363 A1 | 1/2013 | Wong et al. |
| 2013/0072787 A1 | 3/2013 | Wallace et al. |
| 2013/0144116 A1 | 6/2013 | Cooper et al. |
| 2013/0231678 A1 | 9/2013 | Wenderow |
| 2013/0304084 A1 | 11/2013 | Beira et al. |
| 2013/0317519 A1 | 11/2013 | Romo et al. |
| 2013/0345519 A1 | 12/2013 | Piskun et al. |
| 2014/0000411 A1 | 1/2014 | Shelton, IV et al. |
| 2014/0069437 A1 | 3/2014 | Reis et al. |
| 2014/0142591 A1 | 5/2014 | Alvarez et al. |
| 2014/0166023 A1 | 6/2014 | Kishi |
| 2014/0222019 A1 | 8/2014 | Brudnick |
| 2014/0276233 A1 | 9/2014 | Murphy |
| 2014/0276389 A1 | 9/2014 | Walker |
| 2014/0276392 A1 | 9/2014 | Wong et al. |
| 2014/0276394 A1 | 9/2014 | Wong et al. |
| 2014/0276594 A1 | 9/2014 | Tanner et al. |
| 2014/0276933 A1 | 9/2014 | Hart et al. |
| 2014/0276934 A1 | 9/2014 | Balaji et al. |
| 2014/0276935 A1 | 9/2014 | Yu |
| 2014/0276936 A1 | 9/2014 | Kokish et al. |
| 2014/0276937 A1 | 9/2014 | Wong et al. |
| 2014/0276938 A1 | 9/2014 | Hsu et al. |
| 2014/0276939 A1 | 9/2014 | Kokish et al. |
| 2014/0277334 A1 | 9/2014 | Yu et al. |
| 2014/0309649 A1 | 10/2014 | Alvarez et al. |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0051592 A1 | 2/2015 | Kintz |
| 2015/0090063 A1 | 4/2015 | Lantermann et al. |
| 2015/0101442 A1 | 4/2015 | Romo |
| 2015/0119638 A1 | 4/2015 | Yu et al. |
| 2015/0133963 A1 | 5/2015 | Barbagli |
| 2015/0142013 A1 | 5/2015 | Tanner et al. |
| 2015/0148600 A1 | 5/2015 | Ashinuma et al. |
| 2015/0164594 A1 | 6/2015 | Romo et al. |
| 2015/0164596 A1 | 6/2015 | Romo |
| 2015/0182250 A1 | 7/2015 | Conlon et al. |
| 2015/0231364 A1* | 8/2015 | Blanchard ......... A61M 25/0105 604/164.08 |
| 2015/0327939 A1* | 11/2015 | Kokish ............ A61B 34/37 604/95.01 |
| 2015/0335480 A1 | 11/2015 | Alvarez et al. |
| 2015/0374445 A1 | 12/2015 | Gombert et al. |
| 2016/0001038 A1 | 1/2016 | Romo et al. |
| 2016/0007881 A1 | 1/2016 | Wong et al. |
| 2016/0166234 A1 | 6/2016 | Zhang |
| 2016/0235946 A1 | 8/2016 | Lewis et al. |
| 2016/0270865 A1 | 9/2016 | Landey et al. |
| 2016/0279394 A1 | 9/2016 | Moll et al. |
| 2016/0287279 A1 | 10/2016 | Bovay et al. |
| 2016/0296294 A1 | 10/2016 | Moll et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0354582 A1 | 12/2016 | Yu et al. |
| 2016/0374541 A1 | 12/2016 | Agrawal et al. |
| 2016/0374590 A1 | 12/2016 | Wong et al. |
| 2017/0007337 A1 | 1/2017 | Dan |
| 2017/0007343 A1 | 1/2017 | Yu |
| 2017/0065364 A1 | 3/2017 | Schuh et al. |
| 2017/0065365 A1 | 3/2017 | Schuh |
| 2017/0071684 A1 | 3/2017 | Kokish et al. |
| 2017/0100199 A1 | 4/2017 | Yu et al. |
| 2017/0105803 A1 | 4/2017 | Wong et al. |
| 2017/0105804 A1 | 4/2017 | Yu |
| 2017/0119411 A1 | 5/2017 | Shah |
| 2017/0119412 A1 | 5/2017 | Noonan et al. |
| 2017/0119413 A1 | 5/2017 | Romo |
| 2017/0119481 A1 | 5/2017 | Romo et al. |
| 2017/0119484 A1 | 5/2017 | Tanner et al. |
| 2017/0151028 A1 | 6/2017 | Ogawa et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209672 A1 | 7/2017 | Hart et al. |
| 2017/0252540 A1 | 9/2017 | Weitzner et al. |
| 2017/0290631 A1 | 10/2017 | Lee et al. |
| 2017/0296784 A1 | 10/2017 | Kokish |
| 2017/0312481 A1 | 11/2017 | Covington et al. |
| 2017/0333679 A1 | 11/2017 | Jiang |
| 2017/0340396 A1 | 11/2017 | Romo et al. |
| 2017/0360418 A1 | 12/2017 | Wong et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0042464 A1 | 2/2018 | Arai |
| 2018/0049792 A1 | 2/2018 | Eckert |
| 2018/0055583 A1 | 3/2018 | Schuh et al. |
| 2018/0056044 A1 | 3/2018 | Choi et al. |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |

FOREIGN PATENT DOCUMENTS

| | | |
|---|---|---|
| DE | 19649082 | 1/1998 |
| DE | 102004020465 | 9/2005 |
| EP | 1 442 720 | 8/2004 |
| EP | 3 025 630 | 6/2016 |
| JP | 2009-139187 | 6/2009 |
| JP | 2010-046384 | 3/2010 |
| WO | 9945994 A1 | 9/1999 |
| WO | WO 02/074178 | 9/2002 |
| WO | WO 09/092059 | 7/2009 |
| WO | WO 11/005335 | 1/2011 |
| WO | 2012037506 A2 | 3/2012 |

(56) References Cited

FOREIGN PATENT DOCUMENTS

| WO | WO 13/179600 | 12/2013 |
| WO | WO 15/127231 | 8/2015 |

OTHER PUBLICATIONS

Mayo Clinic, Robotic Surgery, https://www.mayoclinic.org/tests-procedures/robotic-surgery/about/pac-20394974?p=1, downloaded from the internet on Jul. 12, 2018, 2 pp.

* cited by examiner

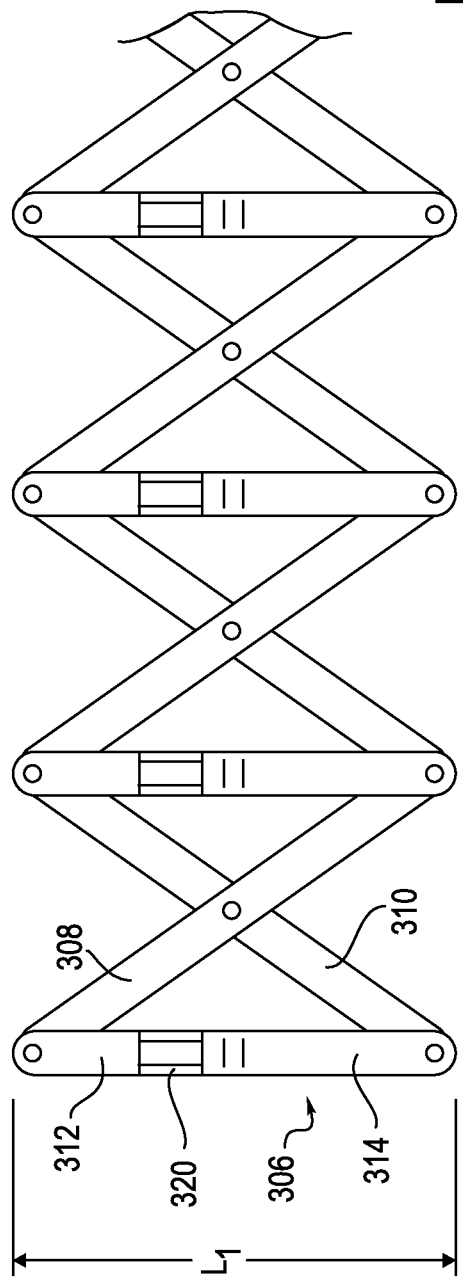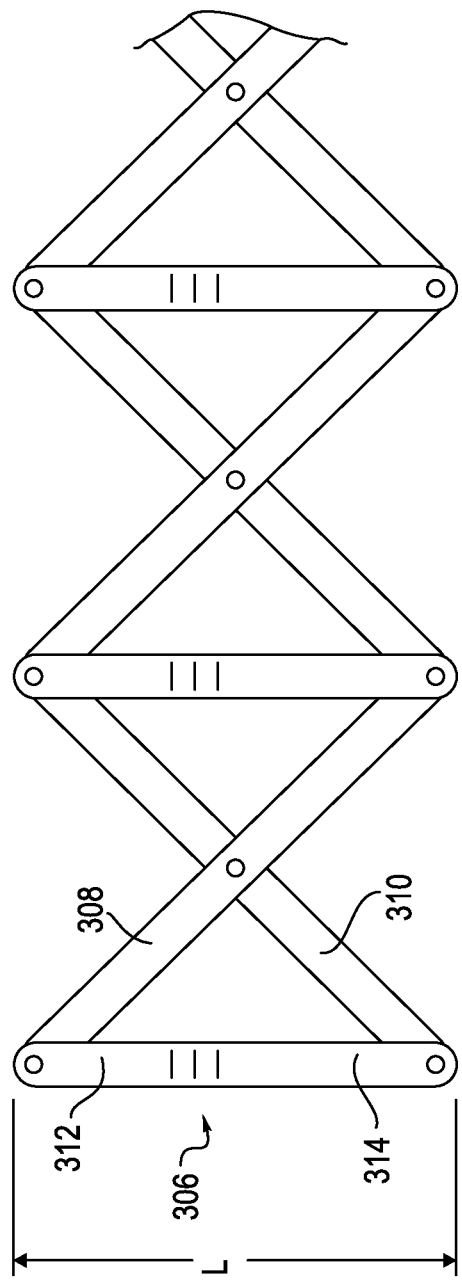

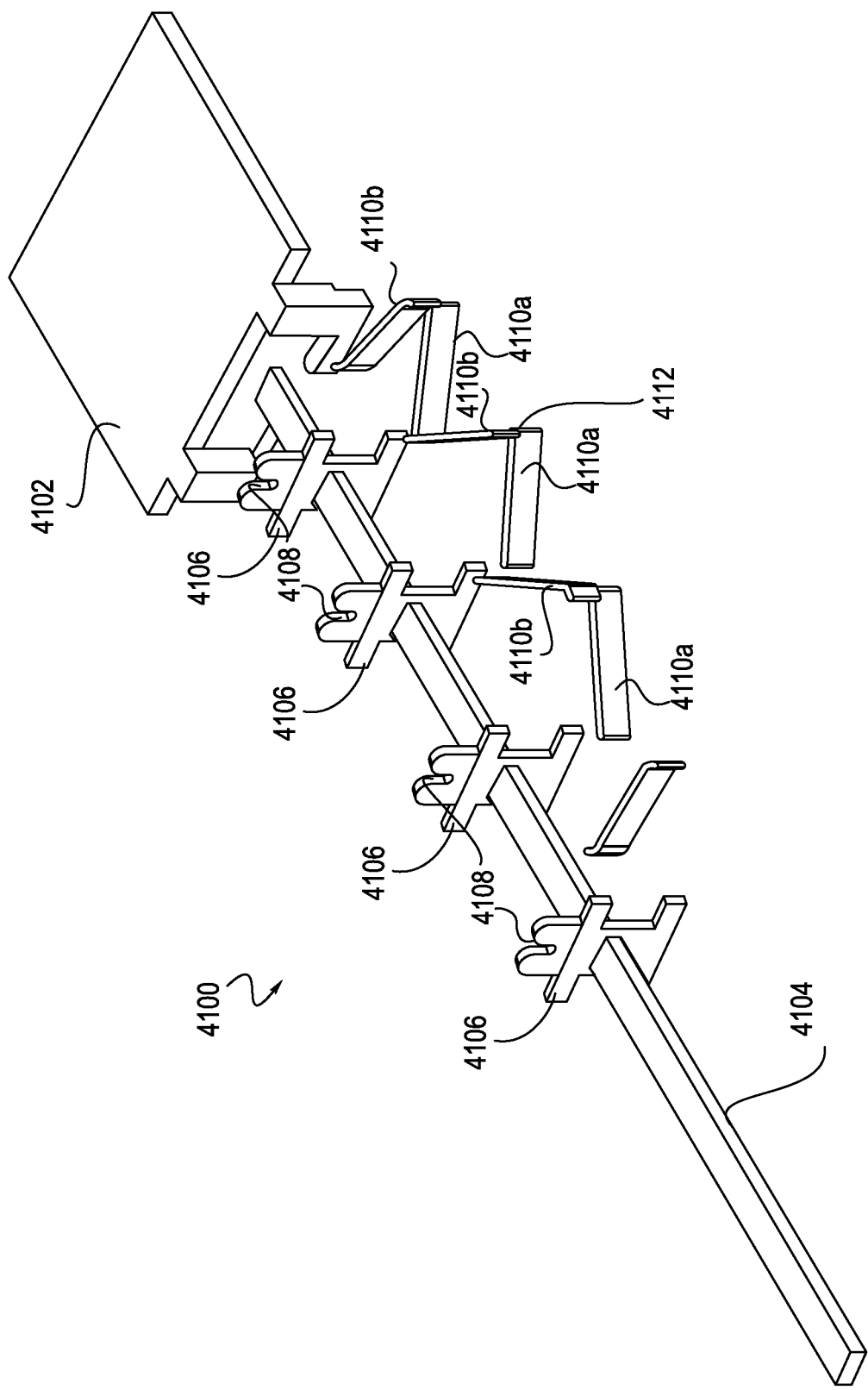

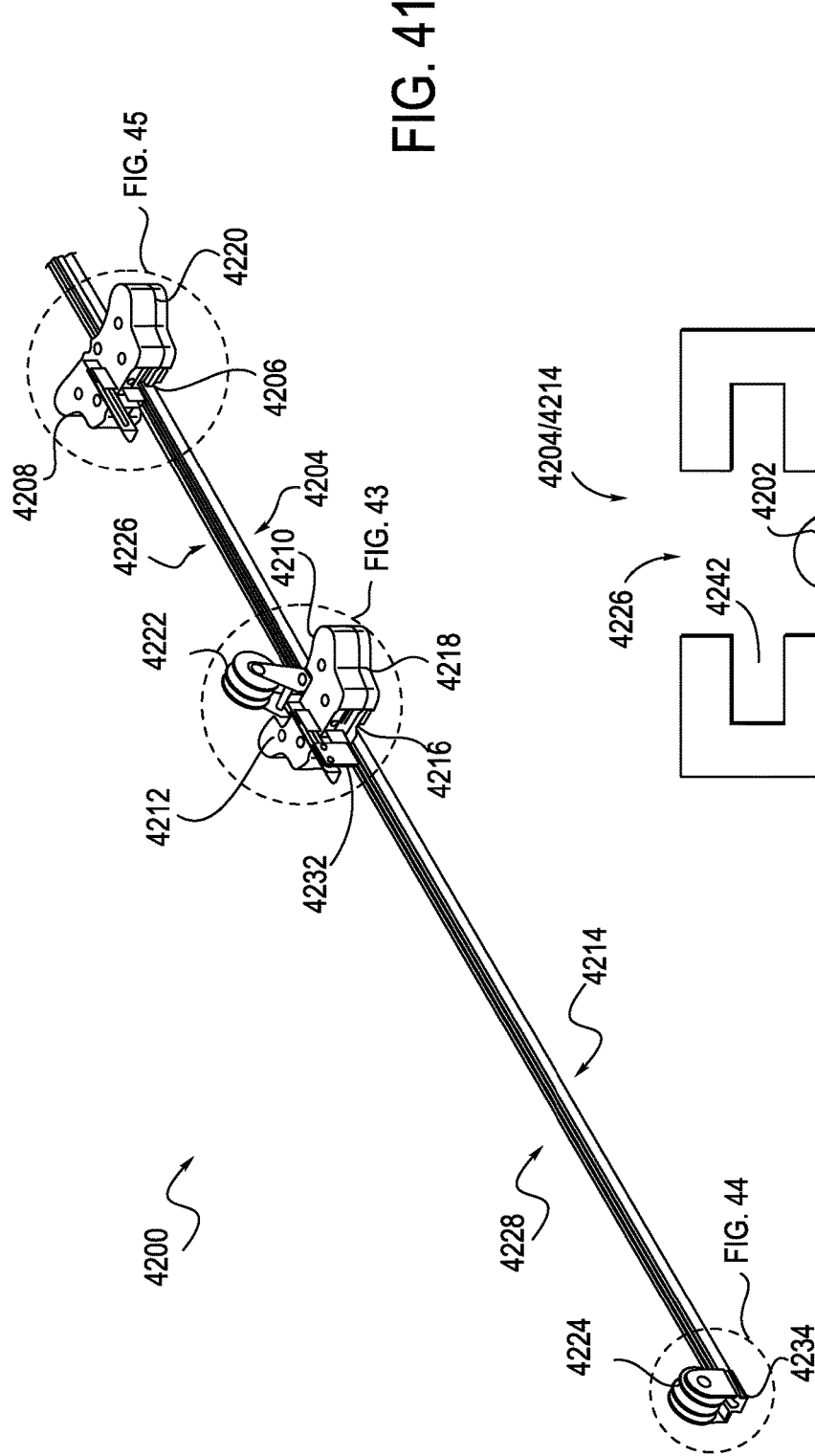
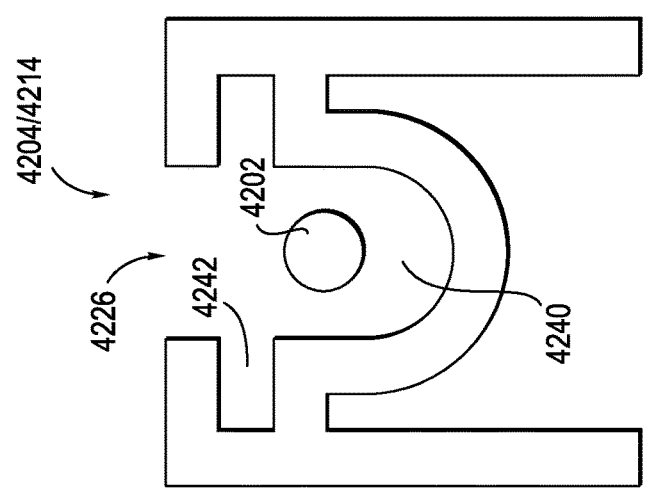

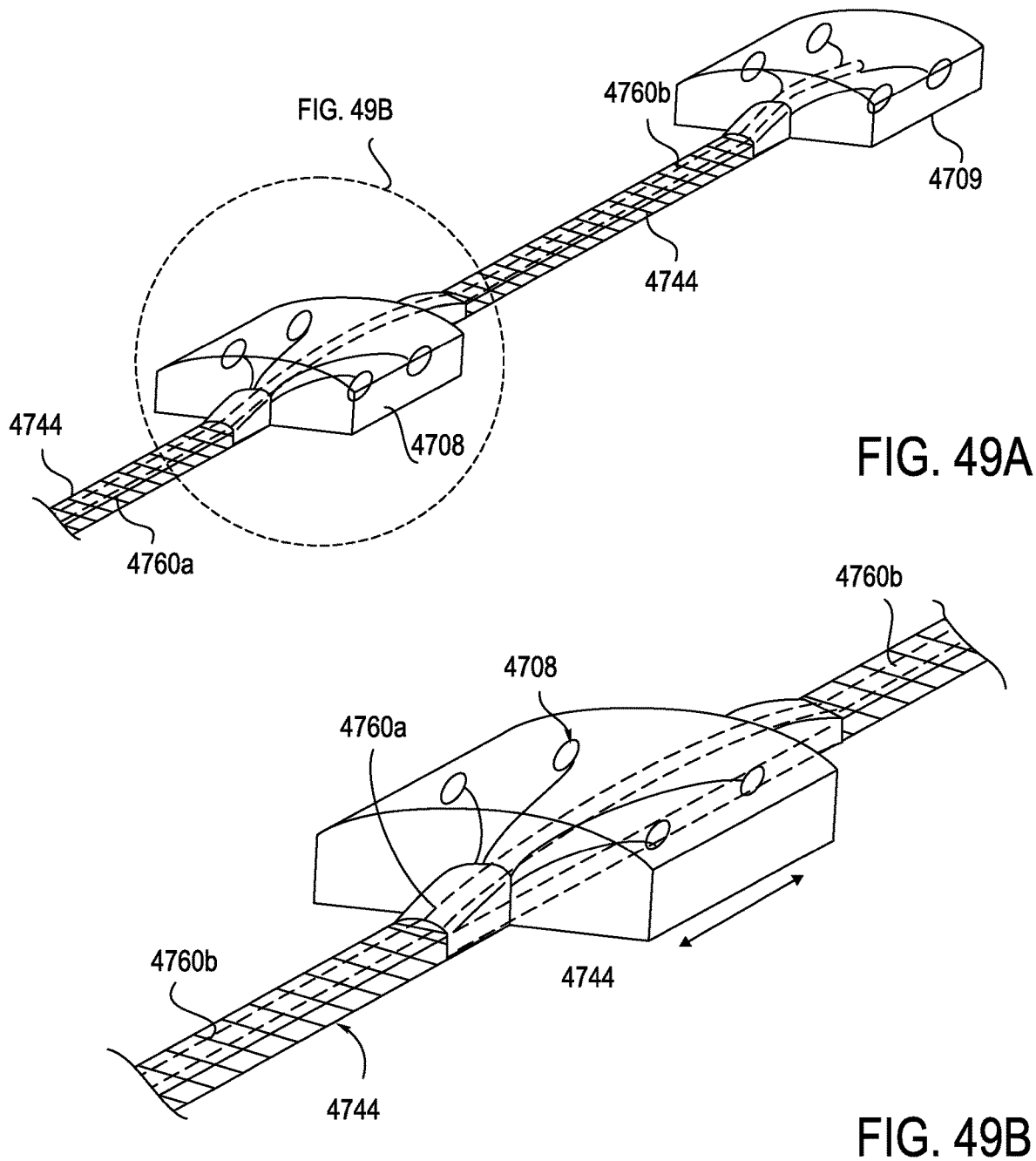

ANTI-BUCKLING MECHANISMS FOR CATHETERS

CROSS-REFERENCE TO RELATED APPLICATIONS

This application claims priority to U.S. Provisional Application No. 61/993,370, Anti-Buckling Channel, filed May 15, 2014, which is incorporated by reference in its entirety herein; U.S. Provisional Application No. 62/014,189, Anti-Buckling Mechanism for Catheters, filed Jun. 19, 2014, which is incorporated by reference in its entirety herein; and U.S. Provisional Application No. 62/057,356, Anti-Buckling Mechanism for Catheters, filed Sep. 30, 2014, which is incorporated by reference in its entirety herein.

This application is related to U.S. Nonprovisional application Ser. No. 13/174,563, Anti-Buckling Mechanisms and Methods, filed Jun. 30, 2011, which is incorporated by reference in its entirety herein.

BACKGROUND

Robotic surgical systems and devices are well suited for use in performing minimally invasive medical procedures, as opposed to conventional techniques that may require large incisions to open the patient's body cavity to provide the surgeon with access to internal organs. For example, a robotic surgical system may be utilized to facilitate imaging, diagnosis, and treatment of tissues which may lie deep within a patient, and which may be preferably accessed only via naturally-occurring pathways such as blood vessels or the gastrointestinal tract. One such robotic surgical system that may be utilized in such a minimally invasive procedure is a robotic catheter system. A robotic catheter system utilizes a robot, external to the patient's body cavity, to insert a catheter through a small incision in a patient's body cavity and guide the catheter to a location of interest.

Catheters by design are typically made of a flexible material that allows for maneuverability through the patient's body cavity, especially the complex tortuosity of blood vessels. The flexible nature of the catheter can cause the catheter to bend, flex, or buckle in an undesirable manner at a point external to the patient's body cavity when force is exerted to insert the catheter into and throughout the body cavity.

Current anti-buckling devices may protect the catheter from undesired flexing and bending, but typically are cost-prohibitive as their structures are complex, requiring multiple components and increased assembly time. Further, known anti-buckling mechanisms often must be placed within the sterile field, requiring disposal of the anti-buckling mechanism at the conclusion of each procedure. Accordingly, there is a need for alternative anti-buckling mechanisms.

SUMMARY

In one aspect, a device for preventing buckling of a flexible elongate member during insertion of the flexible elongate member may include a support frame having a first end, a second end, and multiple pairs of support members. The support frame is configured to reversibly move from a collapsed configuration to an expanded configuration when the first and second ends are moved away from each other. The device may further include multiple open channels coupled to the multiple pairs of support members of the support frame. The multiple open channels are configured to allow the flexible elongate member to be top loaded into the multiple open channels. Also the multiple open channels are maintained in an axial alignment as the support frame is moved between the expanded and collapsed configurations.

In some embodiments, each pair of support members is an alignment member. In some such embodiments, each alignment member defines one of the multiple open channels. In some such embodiments, each alignment member includes a slidable member configured to slide laterally with respect to the open channel to close or open the open channel. In some embodiments, each of the multiple open channels is secured to one of the pairs of support members, such that each open channel is maintained in a substantially fixed rotational position with respect to its corresponding pair of support members.

In some embodiments, the device may further include the flexible elongate member, and each of the multiple open channels may have a diameter that is larger than an outer diameter of the flexible elongate member. Optionally, the device may also include at least one cover configured to selectively cover one of the multiple open channels. In some embodiments, the cover is slidably connected to the one of the multiple open channels. Also optionally, the device may also include multiple alignment members, each defining one of the multiple open channels, where the cover is configured to slide laterally with respect to the one of the multiple open channels. In some embodiments, a diameter of each of the multiple open channels is sufficiently larger than a diameter of the flexible elongate member to allow the elongate member to maintain the axial alignment when the first and second ends are moved with respect to each other. In some embodiments, the device may also include a first coupler positioned on the first end of the support frame, and a second coupler positioned on the second end of the support frame, where the second coupler is configured to position the flexible elongate member.

In another aspect, a device for preventing buckling of a flexible elongate member during insertion of the flexible elongate member may include a support frame as descried above, which includes a first end, a second end, and multiple pairs of support members, and wherein the support frame is configured to reversibly move from a collapsed configuration to an expanded configuration when the first and second ends are moved away from each other. The device may further include multiple alignment members coupled to the multiple pairs of support members of the support frame, where the multiple alignment members are configured to receive the flexible elongate member.

In some embodiments, the multiple pairs of support members and the multiple alignment members are coupled to each other through an axially-centered pivot point. Some embodiments may further include an aperture in each of the multiple alignment members for receiving the flexible elongate member. In some embodiments, each aperture is located at a position off-center from a centerline axis of the anti-buckling device. In some embodiments, each aperture is rotationally constrained. In some embodiments, each alignment member includes a top element and a bottom element, and the bottom element includes rails for slidably coupling to the top element. In some embodiments, each alignment member comprises a slot for slidably coupling to a pin disposed on the multiple pairs of support members to couple the alignment member to the multiple pairs of support members.

These and other aspects and embodiments will be described in further detail below, in reference to the attached drawing figures.

BRIEF DESCRIPTION OF THE DRAWINGS

While the claims are not limited to the illustrated embodiments, an appreciation of various aspects is best gained through a discussion of various examples thereof. Referring now to the drawings, illustrative examples are shown in detail. Although the drawings represent the exemplary illustrations disclosed herein, the drawings are not necessarily to scale and certain features may be exaggerated to better illustrate and explain an innovative aspect of an example. Further, the examples described herein are not intended to be exhaustive or otherwise limiting or restricting to the precise form and configuration shown in the drawings and disclosed in the following detailed description. Exemplary illustrations of the present invention are described in detail by referring to the drawings as follows.

FIGS. 12 and 13 are top views of the anti-buckling mechanism of FIGS. 9-11;

FIG. 40 a schematic illustration of an exemplary anti-buckling support, according to one embodiment;

FIG. 41 is perspective view of an anti-buckling support structure, according to one embodiment;

FIG. 42 is an end-on, cross-sectional view of an exemplary sheath rail, according to one embodiment;

FIGS. 49A and 49B are perspective views of another exemplary anti-buckling mechanism, which includes a long channel, which encapsulates the catheter and employs separate rails for the sheath catheter and leader, according to an alternative embodiment.

DETAILED DESCRIPTION

Figure 1A:
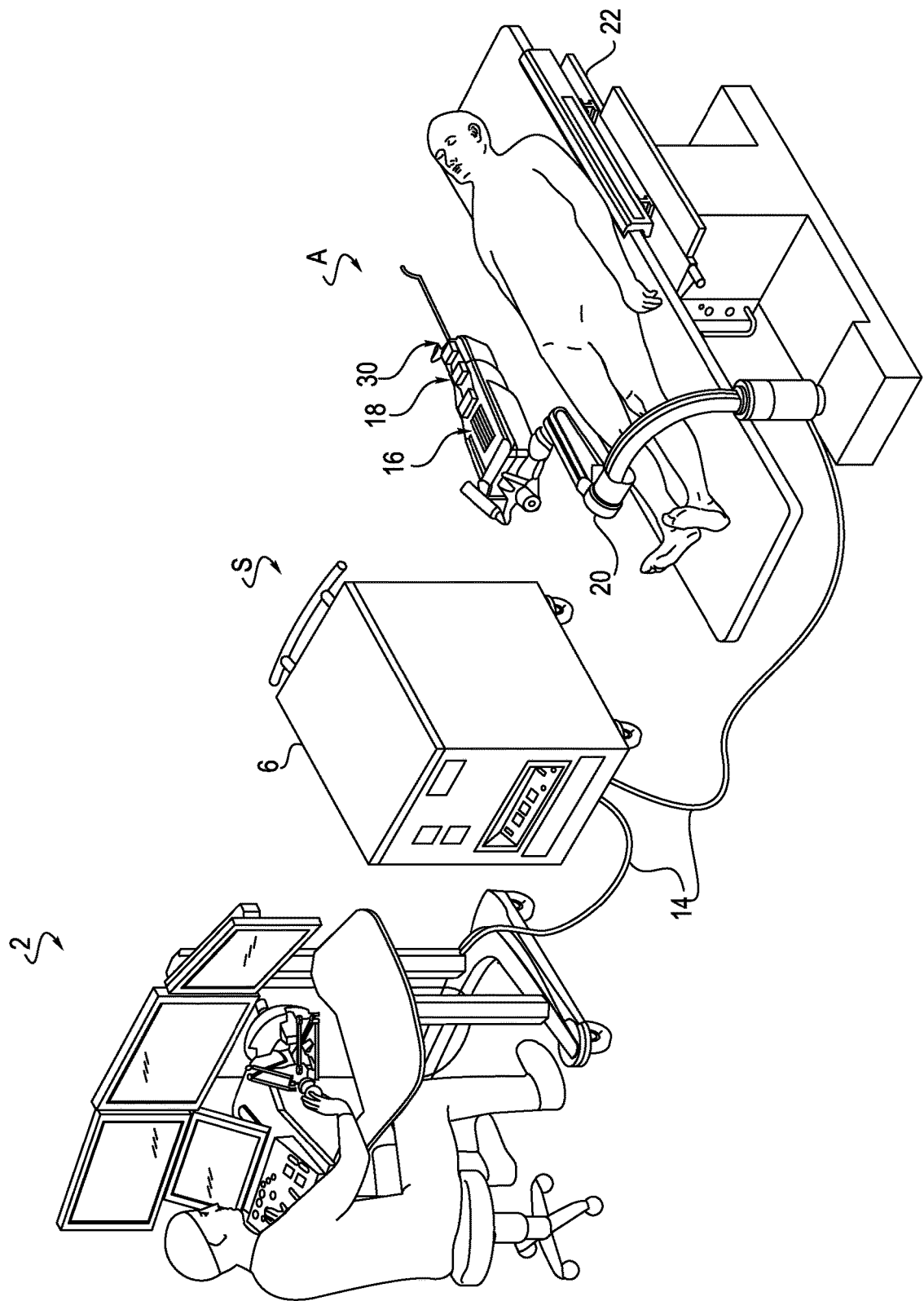
FIG. 1A is a perspective view of a robotically controlled surgical system, according to one embodiment.

Referring now to the discussion that follows and to the drawings, illustrative approaches to the disclosed assemblies are shown in detail. Although the drawings represent some possible approaches, the drawings are not necessarily to scale, and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Exemplary illustrations are generally directed to an anti-buckling mechanism for use with a medical device, including but not limited to use of the anti-buckling mechanism to stabilize a flexible catheter external to a patient's body cavity. The anti-buckling mechanism may take many different forms and may include multiple and/or alternate components and facilities. The exemplary components illustrated are not intended to be limiting. Indeed, additional or alternative components and/or implementations may be used.

System

Referring to FIG. 1A, a robotically controlled surgical system (S), in which various alternative arrangements of exemplary apparatuses may be implemented, includes a robotic catheter assembly (A) having a first or outer robotic steerable component, otherwise referred to as a sheath instrument 30 (generally referred to as "sheath" or "sheath instrument") and/or a second or inner steerable component, otherwise referred to as a robotic catheter or guide or catheter instrument 18 (generally referred to as "catheter" or "catheter instrument"). The sheath instrument 30 and catheter instrument 18 are controllable using a robotic instrument driver 16 (generally referred to as "instrument driver"). During use, a patient is positioned on an operating table or surgical bed 22 (generally referred to as "operating table"), to which a robotic catheter assembly (A) is coupled or mounted. In the illustrated example, the system (S) further includes an operator workstation 2, an electronics rack 6 and associated bedside electronics box, a setup joint mounting brace 20, and the instrument driver 16. In use, a surgeon is positioned at the operator workstation 2 and can monitor the surgical procedure and patient vitals, and control one or more catheter devices, remote from the patient.

While various system (S) components with which embodiments described herein may be implemented are illustrated in close proximity to each other in FIG. 1, embodiments may also be implemented in systems (S) in which components are separated from each other in separate rooms, buildings, and/or geographical locations. For example, the instrument driver 16, operating table 22, and bedside electronics box may be located in a surgical area with the patient, and the operator workstation 2 and the electronics rack 6 may be located outside the surgical area and behind a shielded partition. System (S) components may also communicate with other system (S) components via a network to allow for remote surgical procedures during which the surgeon may be located at a different location, for example in a different building or at a different hospital, using a communication link that transfers signals between the operator control station 2 and the instrument driver 16. System (S) components may also be coupled together via a hard-wired connection 14, for example multiple cables or other suitable connectors to provide for data communication, or one or more components may be equipped with wireless communication components to reduce or eliminate cables 14. In this manner, a surgeon or other operator may control a surgical instrument while being located away from or remotely from radiation sources, thereby decreasing the operator's exposure to radiation.

Figure 1B:
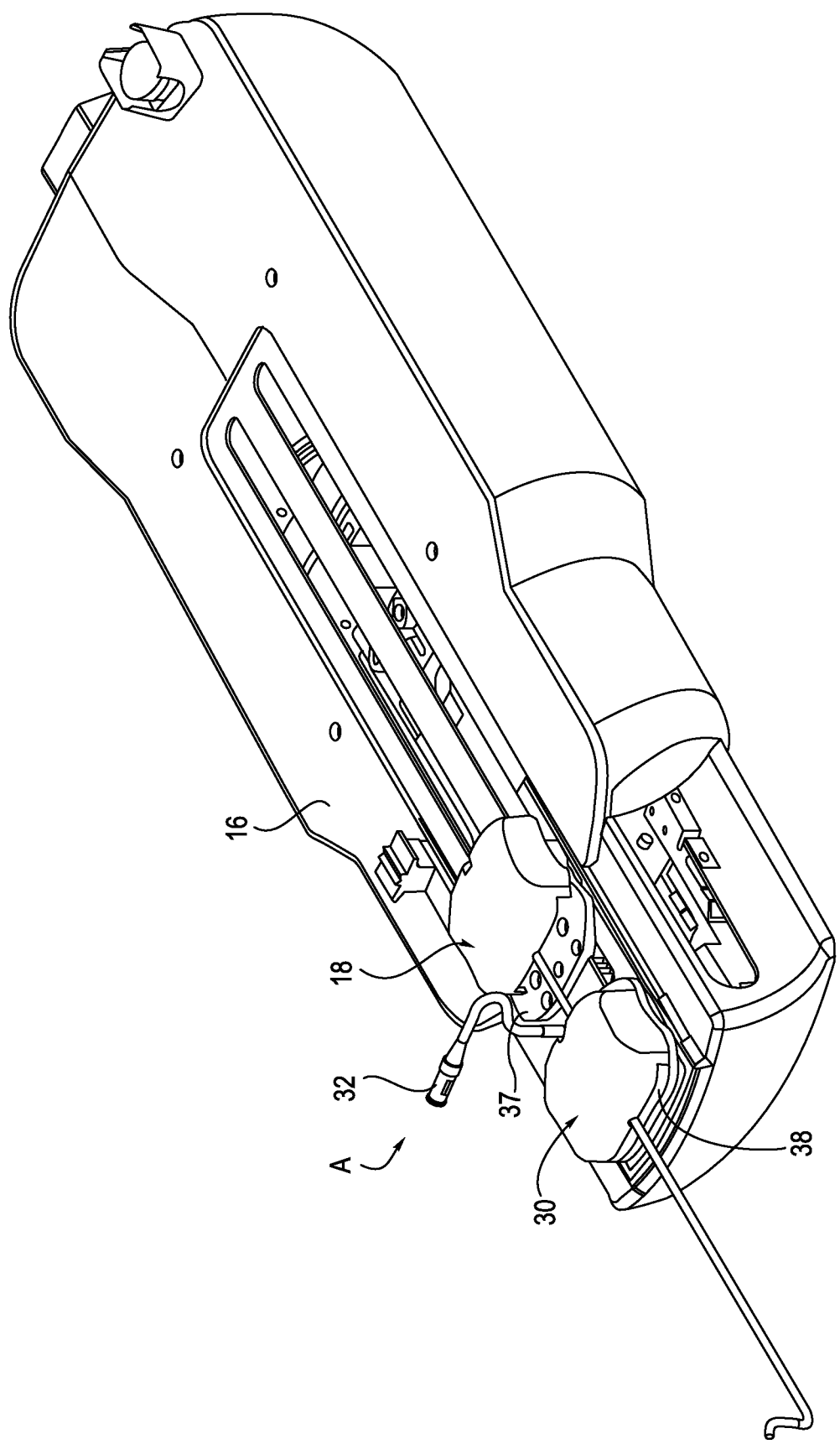
FIG. 1B is a perspective view of an exemplary catheter assembly of the surgical system of FIG. 1A.

With further reference to FIG. 1B, an instrument assembly (A) comprised of a sheath instrument or splayer 30 and an associated guide or catheter instrument or splayer 18 is mounted to mounting plates 37, 38 on a top portion of the instrument driver 16. Embodiments described herein are similar to those described in detail in U.S. patent application Ser. Nos. 11/678,001, 11/678,016, and 11/804,585, each of which is incorporated by reference herein in its entirety.

Figure 1C:
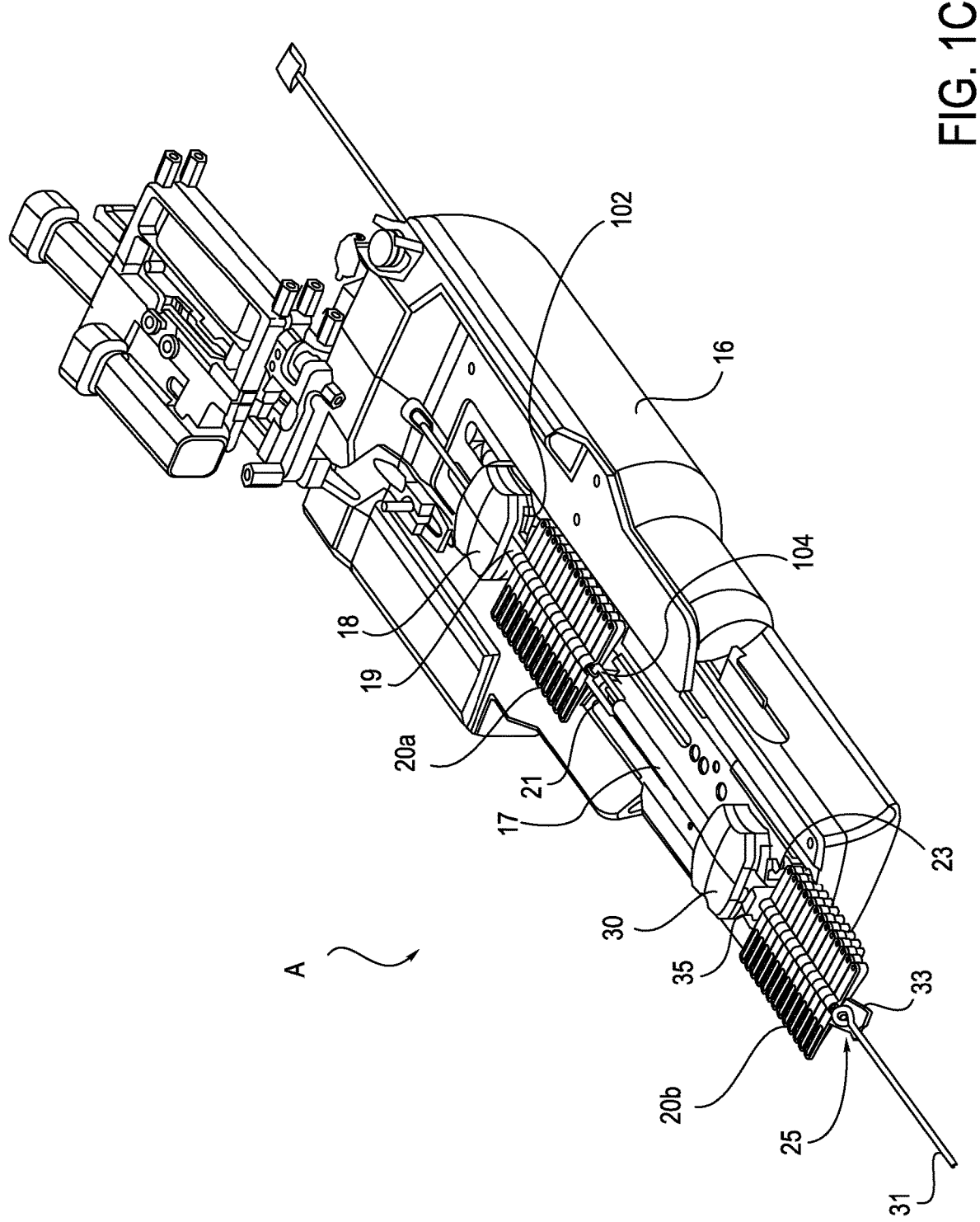
FIG. 1C is a perspective view of an exemplary catheter assembly with a prior art anti-buckling mechanism.

FIG. 1C illustrates further detail of the instrument assembly (A) of FIG. 1B. The instrument driver 16 includes the catheter instrument 18 for positioning a catheter 17, and the sheath instrument 30 for positioning a sheath 31 that is placed coaxially around the catheter 17. In the illustrated embodiments, the sheath instrument 30 is moveable relative to the catheter instrument 18. The sheath and catheter instruments 30 and 18 each have four drivable elements for moving the catheter 17, and the sheath 31, respectively, in different directions. However, in other embodiments, the number of drivable elements in each of the sheath and catheter instruments 30 and 18 may be less than four or more than four. The instrument driver 16 may also include two anti-buckling mechanisms 20a, 20b for preventing the buckling of the catheter 17, and the buckling of the sheath 31, respectively, during use. Various exemplary arrangements of the anti-buckling mechanisms will be described in further detail below.

Anti-buckling mechanisms 20a, 20b are configured to detachably couple to the catheter instrument 18 and sheath instrument 30, respectively. The anti-buckling mechanism 20a may be configured with a first end 102 (shown in FIG. 1C) for detachably coupling to the catheter instrument 18, and a second end 104 for detachably coupling to the sheath assembly (shown in FIG. 1C). During use, the anti-buckling mechanism 20a is placed around an elongate member, for example the catheter 17. The anti-buckling mechanism 20a is then secured to the catheter instrument 18 at the first end 102, and to the sheath instrument 30 at the second end 104. The anti-buckling mechanism 20a provides support along the length of the catheter 17 (or other elongate member) between the instruments 18, 30, such that as the catheter 17 is pushed towards the patient (resulting in the catheter 17 being compressed), and the catheter 17 is prevented from buckling.

The anti-buckling mechanism 20a further includes a first coupler 19 operatively connected to the first end 102 and a second coupler 21 operatively connected to the second end 104. The first coupler 19 is configured to detachably mate with an anchor element of the catheter instrument 18. The second coupler 21 is configured to detachably mate with a mounting element of the sheath instrument 30. An exemplary configuration of the first coupler and anchor element and the second coupler and mounting element is shown and described in U.S. patent application Ser. No. 13/174,563, the contents of which are incorporated by reference in its entirety.

Figure 2:
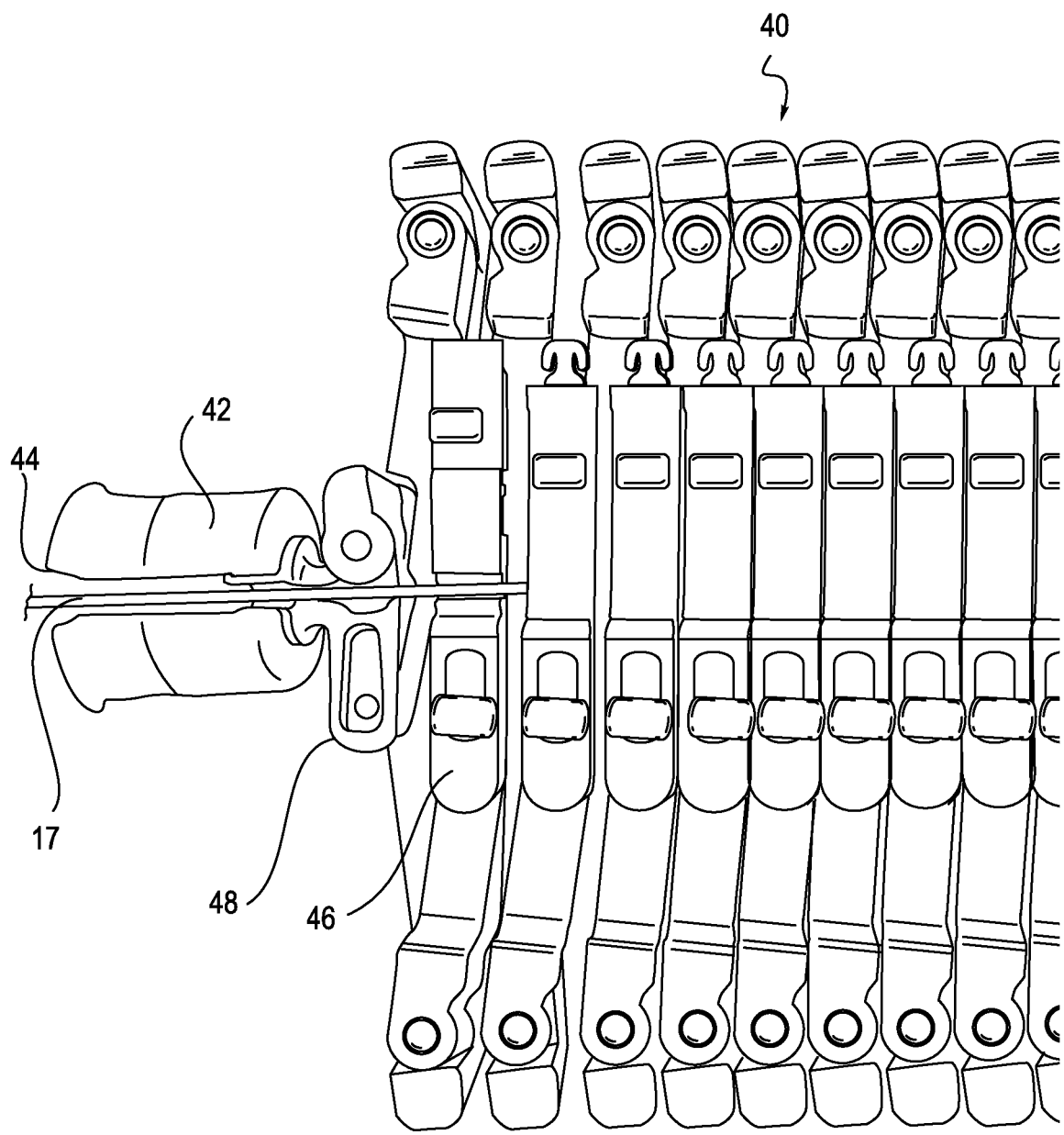
FIG. 2 is a top view of a portion of an exemplary anti-buckling mechanism with a top-loadable coupler, according to one embodiment.

Referring now to FIG. 2, in some embodiments, an anti-buckling mechanism 40 may include a coupler 44 (or multiple couplers 44) that are top-loadable, meaning that the catheter 17 or other elongate member can be loaded into the anti-buckling mechanism 40 from the top. This is opposed to, for example, threading the catheter 17 through a hole at one end of an alternative embodiment anti-buckling mechanism. The coupler 44 may be configured in a C shape, for example, such that the there is a slot or opening 44 in the top of the coupler 44 for receiving the catheter 17 or other elongate member. In alternative embodiments, the coupler 44 may be a rigid connector, and the catheter 17 may pass through a top-loadable eyelet (not shown) on the coupler 44. The first alignment member 46 of the support frame of the anti-buckling mechanism 40 may also include a top loadable eyelet 48 to facilitate top loading of the elongate member 17.

The anti-buckling mechanism 20b is configured to detachably couple to the sheath instrument 30 and a patient or another device, for example a stabilizer (not shown) during use. As shown in FIG. 1C, the anti-buckling mechanism 20b has a first end 35 for detachably coupling to the sheath instrument 30, and a second end 33 for detachably coupling to the stabilizer. During use, the stabilizer is attached to a patient's skin, and the anti-buckling device 20b is placed around the sheath 31. One such exemplary stabilizer is shown and described in U.S. patent application Ser. No. 13/174,563. The distal end of the sheath 31 is then inserted into the patient through the stabilizer. The anti-buckling device 20b is secured to the sheath instrument 30 at the first end 35, and to the stabilizer at the second end 33. The anti-buckling device 20b provides support along the length of the sheath 31 between the stabilizer and the sheath instrument 30, such that as the sheath 31 is pushed towards the patient (resulting in the sheath 31 being compressed), and the sheath 31 is prevented from buckling.

The anti-buckling mechanism 20b further includes a first coupler 23 operatively connected to the first end 35 and a second coupler 25 operatively connected to the second end 33. The first coupler 23 is configured to detachably mate with a mounting element of the sheath instrument 30. The second coupler 25 is configured to detachably mate with a patient or another device, for example a stabilizer mounted to the patient. Alternatively, the second coupler 25 may be configured to detachably mate with an introducer sheath at the insertion site. An exemplary configuration of the first coupler 23 and mounting element and the second coupler 25 and stabilizer is shown and described in U.S. patent application Ser. No. 13/174,563.

Scissor-Like Anti-Buckling Mechanisms

Figure 3:
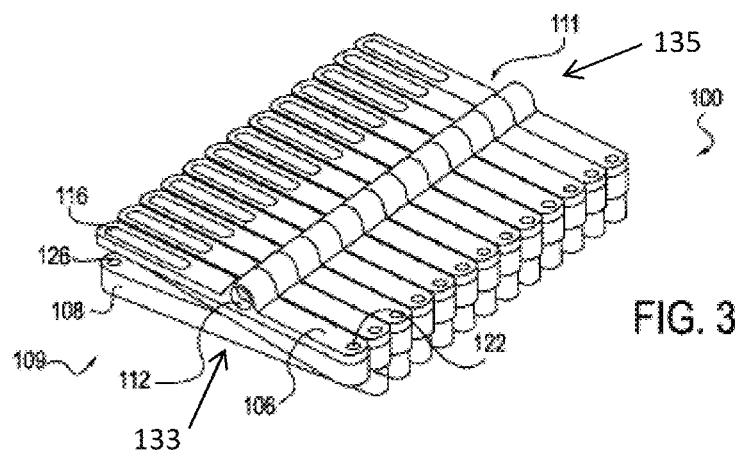
FIGS. 3-5 are perspective views of an exemplary anti-buckling mechanism, in different configurations, which may be used with a robotically controlled surgical system, according to one embodiment.
Figure 4:
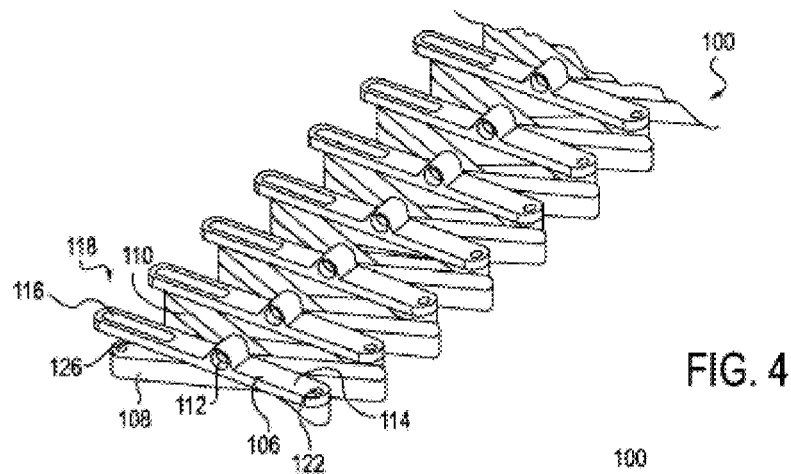
Figure 5:
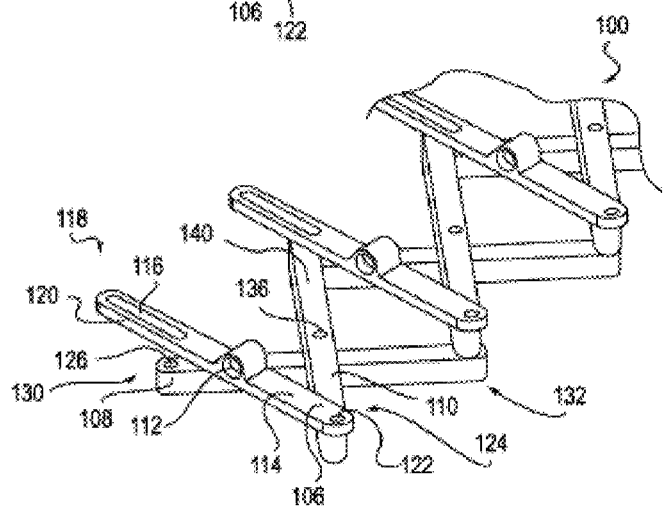
Figure 6:
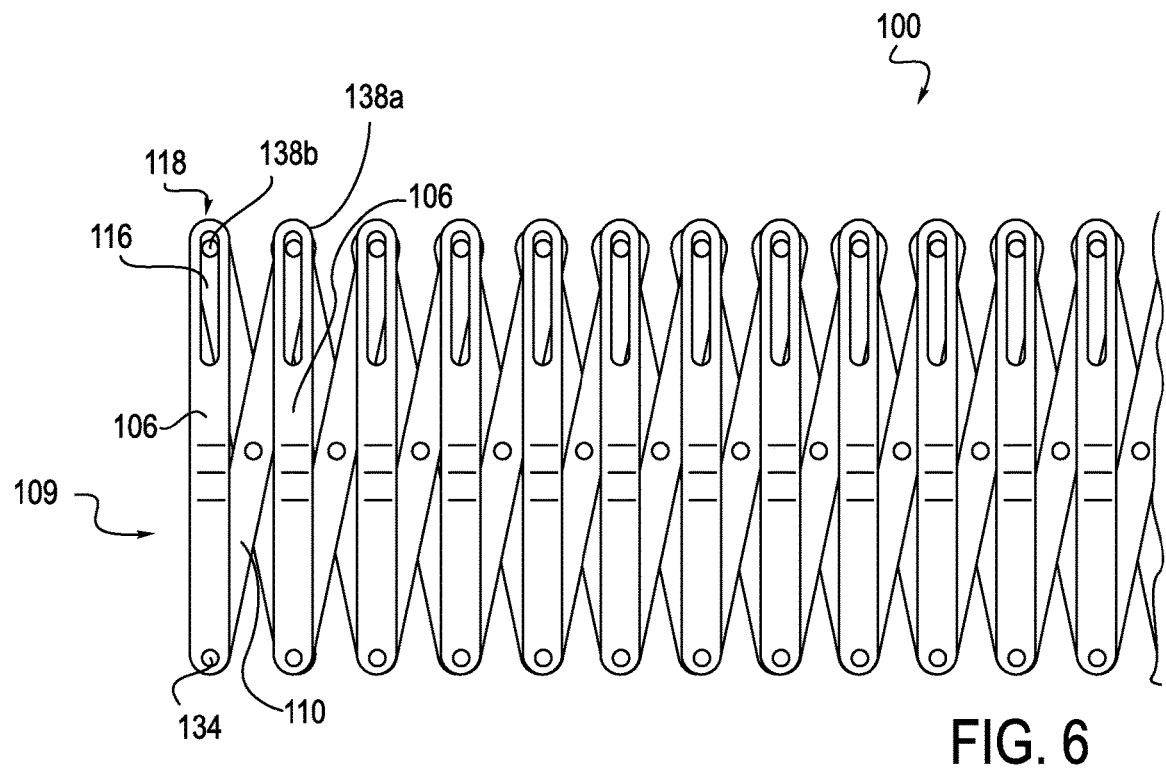
FIGS. 6-8 are top, top and perspective views, respectively, of the anti-buckling mechanism of FIGS. 3-5.
Figure 7:
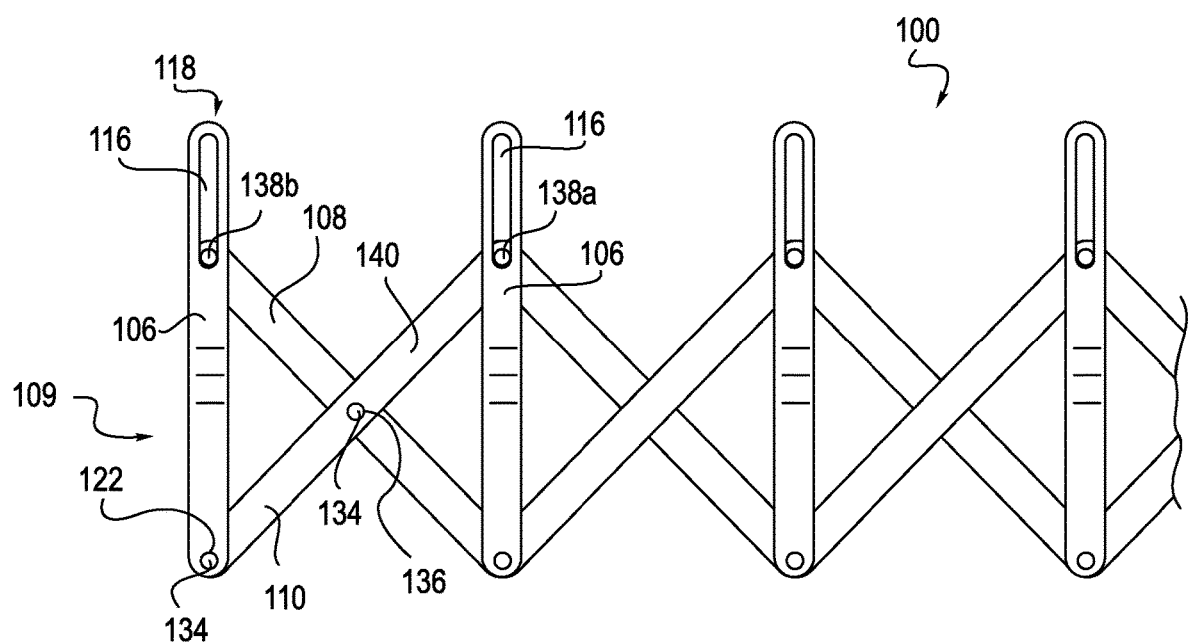
Figure 8:
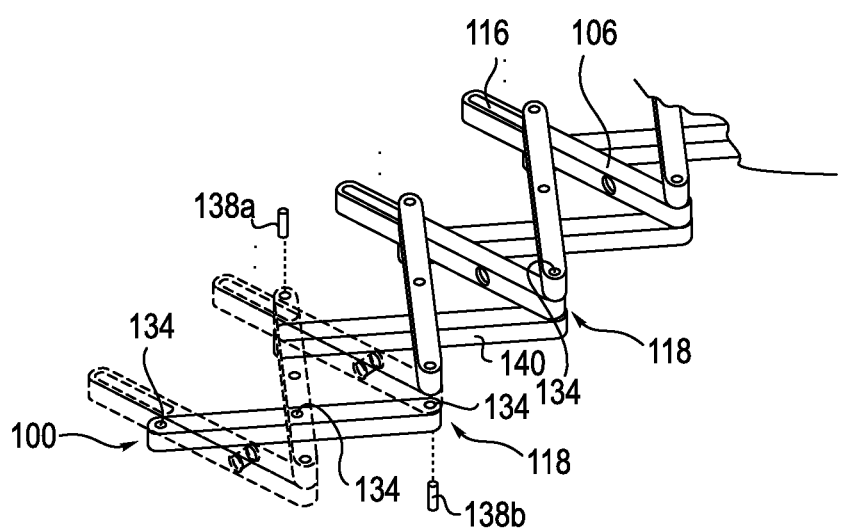

FIGS. 3-8 illustrate different views of an exemplary embodiment of an anti-buckling mechanism 100 in further detail, with the first and second coupling elements being omitted. The anti-buckling mechanism 100 includes multiple support members 108, 110 and an alignment member 106, coupled between a proximal end 109 and a distal end 111 of the anti-buckling mechanism 100, which are connected together to create a selectively expandable scaffolding structure. First support members 108 are positioned on one side of the anti-buckling mechanism 100, and second support members 110 are positioned on the opposite side of the anti-buckling mechanism 100, to create a support frame having a scissor-like configuration having a first end 133 and a second end 135. The alignment members 106 are located on top of the first and second sets of support members 108, 110. Alternatively, in some embodiments, the alignment members are located between or underneath the first and second sets of support members Each alignment member 106 includes an eyelet 112 therethrough, as shown in FIG. 8, or positioned on a top surface 114 thereof, as shown in FIGS. 3-5. The alignment member 106 is generally configured to orient the eyelet 112 such that eyelets 112 defined by a series of alignment members 112 are maintained in an alignment, thus facilitating support of an elongate member, for example a catheter. While eyelet 112 is shown as being integrally formed with the top surface 114 of the alignment member 106, in alternative embodiments eyelet 112 may be separately formed and attached to top surface 114 of the alignment member 106 or a bottom surface of the anti-buckling mechanism 100 or an eyelet or hole passing through the alignment member 106. Further, in one exemplary configuration, the eyelet 112 is slightly offset from a center of the alignment member 106. The eyelet 112 of alignment member 106 functions to receive an elongate instrument, for example a catheter, sheath, guidewire, or any combination thereof.

Alignment member 106 further includes a slot 116 positioned adjacent to one end 118 and extending longitudinally toward eyelet 112. In one configuration, slot 116 extends through both the top and bottom surfaces 114 and 120, respectively, of alignment member 106. However, in alternative embodiments slot 116 is not required to extend through alignment member 106 and thus may only be open on bottom surface 120 or top surface 114.

Alignment member 106 may further include an attachment hole 122, the function of which will be described in greater detail below. In one exemplary arrangement, attachment hole 122 is positioned on end 124, which is opposite end 118.

In one exemplary embodiment, the second support member 108 includes three attachment holes (only 126 being visible in FIGS. 3-5). A first attachment hole 126 is positioned on one end 130 of second support member 108. A second attachment hole (not shown) is positioned on an opposite end 132 of second support member 108. A third attachment hole (not shown) is positioned between the ends 130 and 132. The attachment holes 126 are configured to receive pins, which will be explained in further detail below. The pin joints may also be replaced with other types of joints, for example ball and socket joints or knuckle joints.

The second support member 110 is positioned between alignment member 106 and first support member 108. The second support member 110 also includes three attachment holes 136 (only one of which is visible), which receive pins 138, as shown in FIG. 6. One pin 138a extends upwardly from a top surface 140 of second support member 110. Pin 138a is configured to be received within the slot 116. Pin 138a thus operatively connects second support member 110 to alignment member 106.

Pin 134, as shown in FIG. 7, is configured to hingedly connect the first and second support members 108 and 110. More specifically, in one exemplary embodiment, pin 134 is received in attachment holes 136 (formed in second support member 110), and a corresponding attachment hole (not shown) in first support member 108. Another pin 134 (see FIGS. 6 and 7) hingedly connects the alignment member 106 and the second support member 110 together, such that expanding the anti-buckling device slides pin 138a in slot 116 towards the centerline axis of anti-buckling device, and collapsing the anti-buckling device slides pin 138a in slot 116 outwardly away from the centerline axis of the anti-buckling device. Further, as described above, pin 138a operatively connects second support member 110 to alignment member 106.

The proximal end 109 of the anti-buckling mechanism 100 is configured such that alignment member 106 receives a pin 138b (visible in FIGS. 6 and 7) extending from attachment hole 126 (See FIGS. 3-5). Pins 138a, 138b may be longer than pin 134, to span the distance between a top surface of first support member 108 and at least a portion of the thickness of the alignment member 106, to be slidingly received in the slot 116, as shown in FIGS. 6 and 7.

The interaction between pins 138a and 138b on support members 108, 110 and slots 116 on alignment members 106 allows successively arranged support members 108, 110 to be spaced apart from one another, thereby providing a frame to prevent buckling of a catheter 17 and/or sheath 31. More specifically, with reference to FIG. 6, when the anti-buckling mechanism 100 is moving toward a compressed configuration, pins 138a, 138b are disposed adjacent end 118. When the pins 138a, 138b are positioned at the respective ends 118 of the slots 116, the support frame is collapsed or substantially so, and the successive support members 108, 110 and alignment member 106 are positioned adjacent to one another (see FIG. 3, for example). In contrast, when the anti-buckling mechanism 100 is in a fully expanded configuration, as shown in FIG. 7, the pins 138a, 138b have traveled the length of the respective slots 116, toward the center of the anti-buckling mechanism. In this configuration, the successively arranged support members 108, 110 are spaced apart from one another. More specifically, support members 108 and 110 are pivoted about the pins 134 disposed in the center and at the end 124 of support members 108 and 110, thereby forcing support members 108, 110 to be spaced apart from one another. While the preceding description identifies alignment member 106 positioned on top of support members 108 and 110, the alignment member 106 may also be positioned under or in between support members 108 and 110, as shown in FIG. 8.

This arrangement of anti-buckling mechanism 100 ensures that the individual eyelets 112 of successive support members 108, 110 and alignment members, 106 are automatically aligned to form a pathway for the catheter 17 and/or sheath 30. Thus, the design of anti-buckling mechanism 100 is more robust in negating eyelet misalignment, thereby avoiding damage to the catheter 17 and/or sheath 30. Further, the above-described design also provides sufficient rigidity to the catheter 17 and/or sheath 30 during use, but is configured to yield a lighter design, with minimal components that has fewer tendencies to bind. Accordingly, anti-buckling mechanism 100 is cost-effective to manufacture, while reducing potential failure points.

Figure 9:
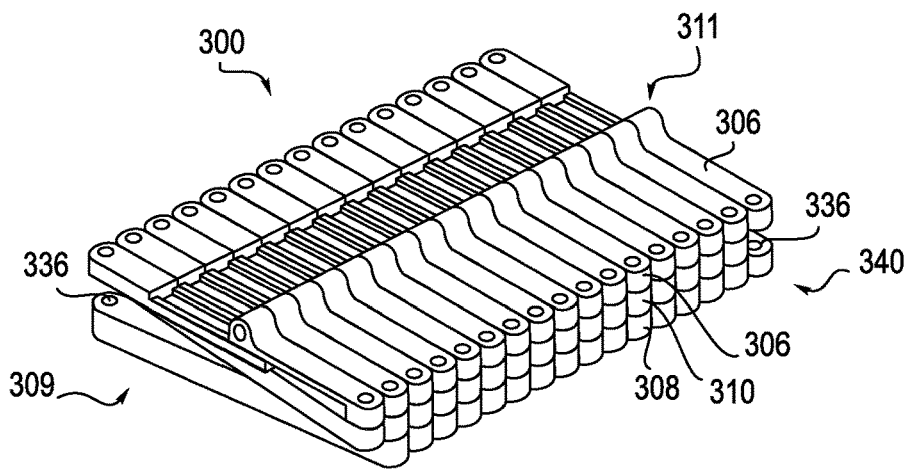
FIGS. 9-11 are perspective views of an exemplary anti-buckling mechanism, in different configurations, which may be used with a robotically controlled surgical system, according to an alternative embodiment.

A further alternative embodiment for an anti-buckling mechanism 300 is illustrated in FIGS. 9-13. FIG. 9 illustrates the anti-buckling mechanism 300 in a compressed arrangement, while FIGS. 10-13 illustrate the anti-buckling mechanism 300 in an expanded arrangement. The anti-buckling mechanism 300 includes multiple successively arranged first and second support members 308, 310, respectively, and alignment member 306 coupled between a proximal end 309 and a distal end 311 of the anti-buckling mechanism 300. Alignment members 306 are on one side of the anti-buckling mechanism 300, and the first support members 308 are on the opposite side of the anti-buckling mechanism 300. Second support members 310 are located between the alignment members 306 and first set of support members 308. In the illustrated embodiments, alignment member 306 and support members 308 and 310 cooperate to create a scissor-like scaffolding mechanism.

Figure 11:
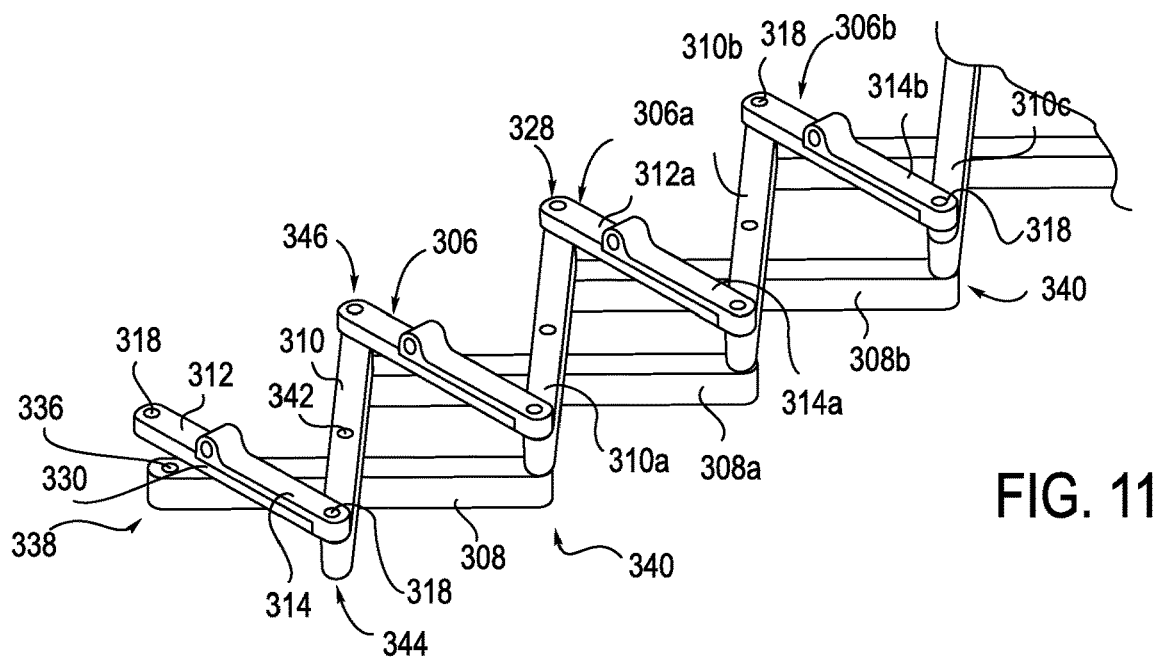

As shown in FIGS. 11 and 12, alignment member 306 is comprised of two mating components; a bottom element 312 and a top element 314. Bottom element 312 is defined by an end 316 that includes an attachment hole 318 therein. A portion of bottom element 312 is formed with rails 320. Rails 320 extend from a wall member 322 to an end 324 of bottom element 312, such that compressing the anti-buckling mechanism drives top element 314 on the rails 320 to connect with bottom element 312, as shown in FIG. 11.

Top element 314 has a bottom surface that is configured to matingly engage with rails 320. In one exemplary arrangement, the bottom surface of top element 214 includes a center projection that is configured to slide between rails 320. In another exemplary arrangement, the bottom surface of top element includes groove members that receive the rails 320 therein such that the top element 214 may slide with respect to bottom element 312.

Top element 314 is defined by an end 326 that also includes an attachment hole 318 therein. An inwardly facing wall member 328 is formed in the bottom surface of top element 314, adjacent end 326.

Each top element 314 of alignment member 306 further includes an eyelet 330 positioned on a top surface 332 thereof. Eyelet 330 is positioned adjacent an end 334 of top element 314. While eyelet 330 is shown as being integrally formed with the top surface 332 of the top element 314 of the alignment member 306, it is understood that eyelet 330 may also be separately formed and attached to top surface 332. Eyelet 330 functions to receive an elongate member, for example a catheter, sheath, and guidewire, or any combination thereof.

In one exemplary embodiment, the first support member 308 includes three attachment holes 336. A first attachment hole 336 is positioned on one end 338 of first support member 308. A second attachment hole 336, as shown in FIG. 9, is positioned on an opposite end 340 of first support member 308. A third attachment hole (not shown) is positioned between the ends 338 and 340, at approximately the center of the first support member 308. The attachment holes 336 are configured to receive pins (not shown), in a similar manner that has been described above in connection with anti-buckling mechanisms 100 and 200.

The second support member 310 is positioned between alignment member 306 and support member 308. The second support member 310 also includes three attachment holes (only one of which is visible, 342), which receive pins, in a manner similar to that which has been described above in connection with anti-buckling mechanisms 100 and 200. The attachment holes 342 of the second support member 310 are positioned adjacent ends 344 and 346, with one being located in the approximate center of second support member 310.

Attachment hole 342 of one of the second support members 310a that is positioned adjacent end 344 is aligned with attachment hole 318 disposed in top element 314 of alignment member 306. A pin (not shown) is received within the aligned attachment holes 342/318 so as to hingedly connect one end of second support member 310a to one end of alignment member 306. Attachment hole 342 of the same second support element 310a that is positioned adjacent end 346 is aligned with attachment hole 318 of another, successively arranged alignment member 306a, as shown in FIG. 11, for example. More specifically, attachment hole 342 positioned adjacent end 346 is aligned with attachment hole 318 of the bottom element 312a. A pin (not shown) is received within the aligned attachment holes 342/318 so as to hingedly connect the other end of the second support member 310a to one end of an adjacent alignment member 306a.

Figure 10:
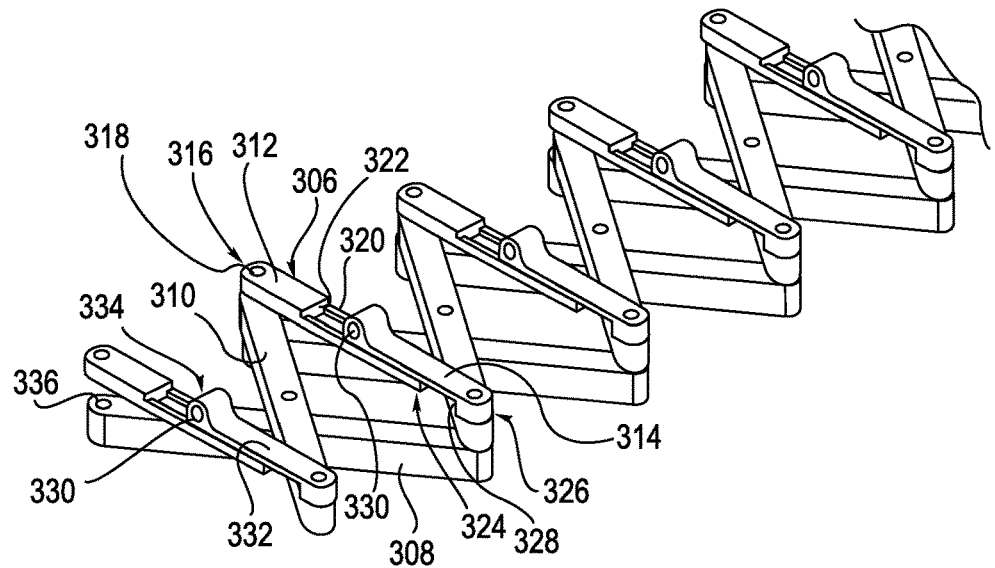

Attachment hole 336 that is positioned adjacent end 338 of the first support member 308b is also aligned with attachment hole 318 disposed in the bottom element 312a of the alignment member 306a. However, as shown in FIGS. 10 and 11, end 346 of the second support member 310a is positioned between the alignment member 306a and first support member 308a. End 340 of the first support member 308b extends away from the connected second support member 310a, and includes an attachment hole 336 that is aligned with an attachment hole 318 disposed in the top element 314b of another, successively arranged, alignment member 306b. Further, as shown in FIGS. 10 and 11, end 346 of another second support member 310c is positioned between the alignment member 306b and first support member 308b. A pin (not shown) is received within the aligned attachment holes 336/318 so as to hingedly connect the other end 340 of the first support member 308b to ends of successively arranged adjacent alignment member 306b and second support member 310c.

In use, when the anti-buckling mechanism 300 is in its compressed configuration, as shown in FIG. 9, the alignment members 306 are positioned adjacent one another, with all of the eyelets 330 aligned, thereby creating a channel for the flexible instrument, such as a catheter or sheath. Due to the interaction of the hinged connections of the first and second support members 308, 310, as the alignment members 306 are being brought closer together, the top and bottom elements 312, 314 of the alignment members 306 slide apart in a telescoping manner, thereby lengthening the alignment member 306, as shown in FIGS. 10 and 12, represented by distance $L_1$. When in the fully compressed position, top element 314 will be positioned adjacent the end 324 of the bottom element 312, as shown in FIG. 9. However, as the anti-buckling mechanism 300 is expanded, the top and bottom elements 314 will slide together in a telescoping manner until end 334 of top element abuts wall 322 of bottom element 312 and end 324 of bottom element 312 abuts wall 328 of top element, as shown in FIGS. 10 and 11. In this configuration, the length L of alignment members 306 is at its shortest length, as shown in FIG. 13.

The interaction between the hinged connections of the first and second support members 308, 310, as well as the telescoping alignment member 306, allows successively arranged support members 308, 310 to be selectively spaced apart from one another, thereby providing a frame to prevent buckling of a catheter 17 and/or sheath 30, as the catheter 17/sheath 30 are advanced toward a patient. Further, this arrangement of anti-buckling mechanism 300 ensures that the individual eyelets 330 of successive alignment members 306 are automatically aligned to form a pathway for the catheter 17 and/or sheath 30. Thus, the design of anti-buckling mechanism 300 is robust in reducing eyelet misalignment, while providing sufficient rigidity to the catheter 17 and/or sheath 30 during use.

Figure 14:
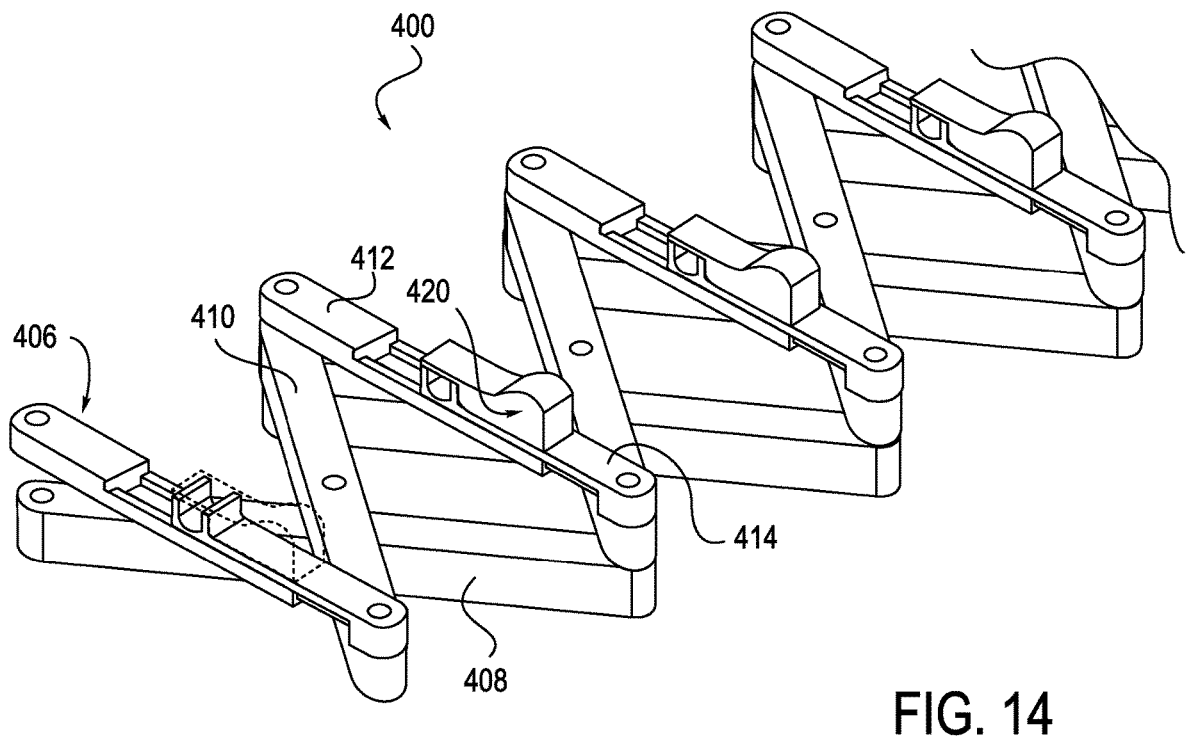
FIGS. 14 and 15 are perspective views of an exemplary anti-buckling mechanism, in different configurations, which may be used with a robotically controlled surgical system, according to an alternative embodiment.
Figure 15:
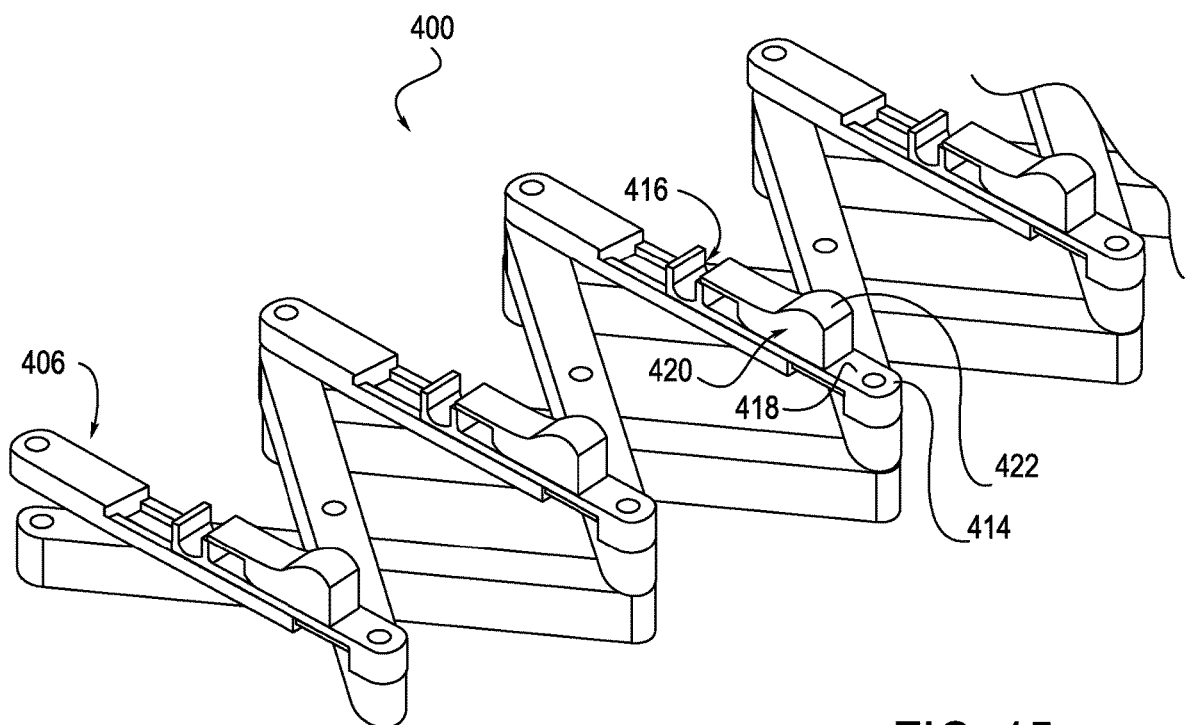

Another alternative embodiment of an anti-buckling mechanism 400 is illustrated in FIGS. 14 and 15. The anti-buckling mechanism 400 is similar to the anti-buckling mechanism 300 in that it includes second and third support members 408, 410, respectively, which are connected together in the same manner as discussed above in connection with the anti-buckling mechanism 300. Further, alignment member 406 is also comprised of bottom and top elements 412 and 414, whereby the bottom element 412 includes rails that are arranged to telescopically engage with complementary elements disposed on a bottom surface of top element 414 so as to selectively expand the length of the anti-buckling mechanism 400 as it moves toward a compressed configuration (not shown).

However, instead of an eyelet, the top element 414 includes an open channel section, which defines a groove 416 formed on a top surface 418 of the top element 414, as shown in FIG. 15. The groove 416 is sized to receive a flexible instrument therein, such as a catheter and/or a sheath. The top element 414 further comprises a slidable closure member 420. Closure member 420 is configured to close off groove 416. To facilitate operation of the closure member 420, a contoured portion 422 may be provided to allow easy opening and closing of groove 416.

The previous exemplary embodiments for anti-buckling mechanisms 100, 200 and 300 all require that the flexible instrument be threaded through the eyelets 112, 330 or apertures 222. The embodiment of anti-buckling mechanism 400 allows for top loading/unloading of the flexible instrument. More specifically, a flexible instrument member may be loaded into each of the open channels in a direction perpendicular to an axis of the open channels, for example perpendicular to the direction of expansion/collapse of the support frame.

The alignment members 406 may be secured to the support frame defined by the pairs of support members 408, 410 such that a fixed rotational position of the supports, for example the channel section grooves 416, is maintained with respect to the other grooves 416 during both expansion and collapse of the support frame defined by the support members 408, 410. The alignment members 406 are generally maintained parallel to each other as the support frame defined by the first and second members 408, 410 is expanded and collapsed. Moreover, the support frame is relatively simplified in arrangement as it employs single pairs of the support members 408, 410 to define a scissor-like arrangement, resulting in a relatively inexpensive and uncomplicated design for the support frame.

Figure 16A:
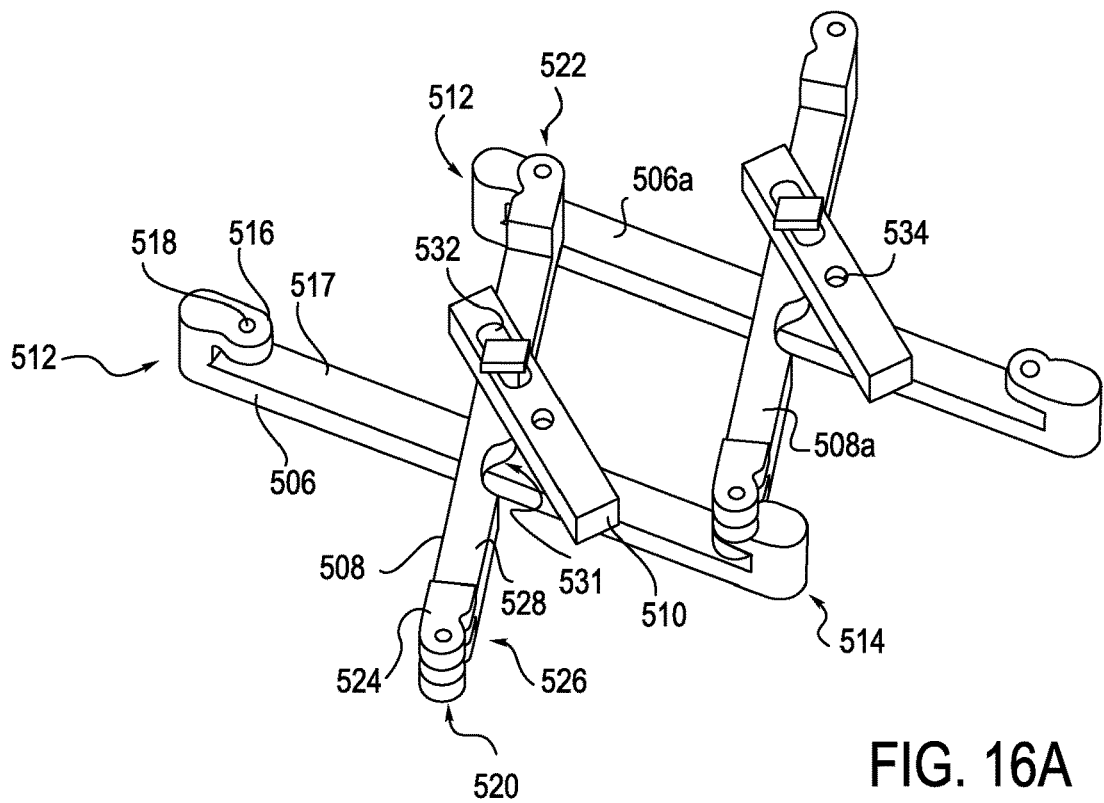
FIG. 16A is a perspective view of an exemplary anti-buckling mechanism that may be used with a moveable eyelet, which may be used with a robotically controlled surgical system, according to one embodiment.

A further exemplary embodiment of an anti-buckling mechanism 500 is partially shown in FIG. 16A. Anti-buckling mechanism 500 includes an alignment member 510, a first support member 506, and a second support member 508. The first support member 506 is defined by first and second ends 512, 514, respectively. Each of the first and second ends 512, 514 include inwardly extending flanges 516 that are positioned over the beam that defines the first support member 506. A bottom surface of the flanges 516 is spaced away from a top surface 517 of the beam so as to define a gap there between. Extending through the flanges 516 are attachment holes 518.

The second support member 508 is defined by first and second ends 520, 522, respectively. Each of the first and second ends 520, 522 includes a pair of inwardly extending flanges 524 that are spaced apart to define a gap 526 there between. Extending upwardly from a top surface 528 of the second support member 508 is a mushroom pin 530. A contoured cut-out 531 is formed within the support member 508 to accommodate a pin connection that serves to connect the first support member 506 to the alignment member 510.

Figure 16B:
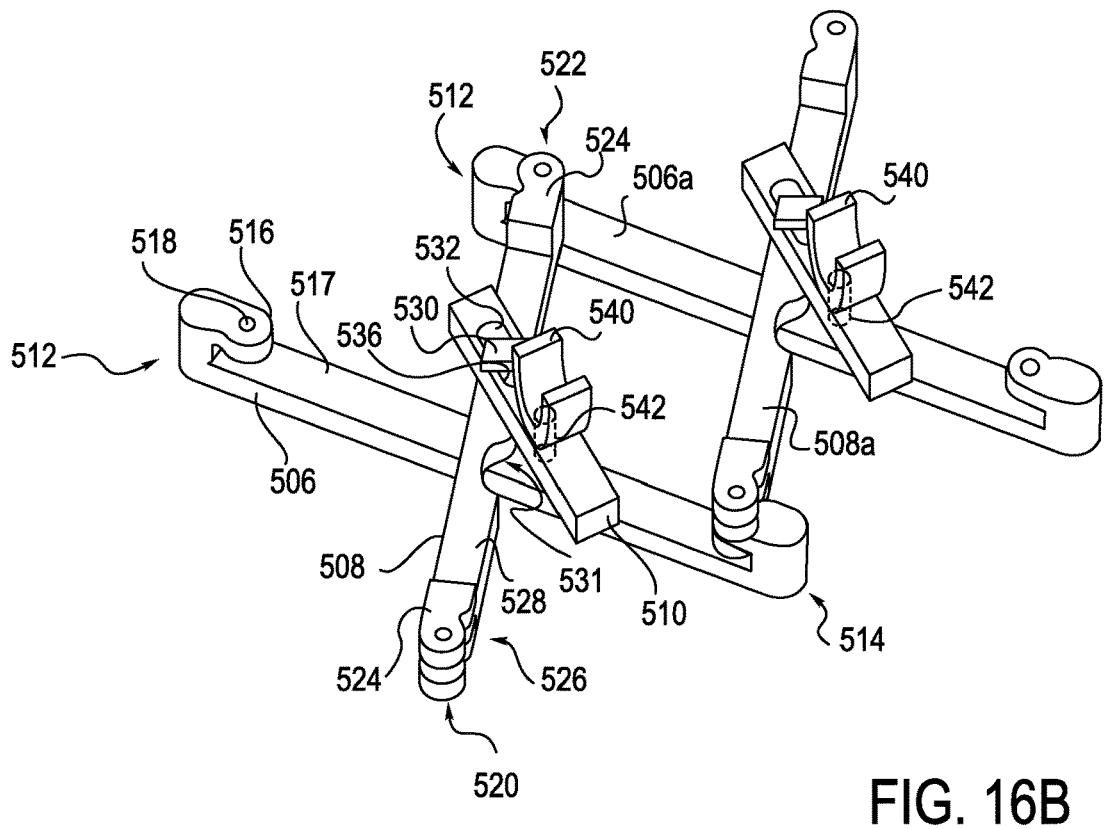
FIG. 16B is a perspective view of an exemplary anti-buckling mechanism with a moveable eyelet, which may be used with a robotically controlled surgical system, according to an alternative embodiment.

The alignment member 510 includes an elongate slot 532 and an attachment hole 534. The slot 534 engages with the mushroom pin 530, as will be explained in further detail below. The attachment hole 534 may receive a pin (not shown in FIG. 16A) that is mounted for rotation that is engaged to the first support member 506. The alignment members 510 are configured to support an eyelet or channel in any suitable manner through which a flexible instrument such as a catheter and/or guide can extend. For example, as shown in FIG. 16B, an eyelet or open channel section 540 may be defined by an alignment pin 542 that is received in the attachment hole 534. Moreover, the attachment hole 534 may facilitate passive rotation of the eyelet 540 and/or the alignment pin 542, thereby allowing a series of eyelets to maintain rotational alignment with respect to an elongate member received within the eyelets 540. In this manner, the eyelets 540 may provide anti-buckling support radially with respect to the flexible member during expansion and contraction of the support frame defined by the support members 506, 508.

End 522 of a second support member 508 is engaged with end 512 of a first support member 506a such that flange 516 of the first support member 506a is received between flanges 524 disposed at end 522 of the second support member 508. Attachment holes 518 of the first and second support members 506a and 508 are aligned. In one exemplary configuration, a tapered pin (not shown) is inserted into the aligned attachment holes 518, thereby forming an external hinge point. The pin is sufficiently long enough to minimize an angle in the lateral direction providing lateral bending, thereby achieving a tight lateral fit between the support members 506, 508.

Second support member 508 extends over the successive and adjacent first support member 506. End 524 of second support member 508 would then be engaged with an end 514 of another first support member (not shown) that would be positioned to the right of first support member 506 in FIG. 16A, in a manner similar to that which was described above (and as shown with the attachment of 508a to 506).

During assembly, the alignment member 510 is positioned over the head of the mushroom pin 530 and rotated such that the head of the mushroom pin 530 extends through the slot 532. Once the mushroom pin 530 clears the slot 532 the alignment member 510 is rotated such that the mushroom head is not able to pass through the slot 532. However, a stem 536 of the mushroom pin 530 is able to slide along the slot 532 during use of the anti-buckling mechanism 500. A pin (not shown) is inserted into attachment hole 534 and engaged with first support member 506 such that the pin is free to rotate within the attachment hole 534.

In use, the first and second support member 506, 508 rotate about a center point defined by the pin that is received within attachment hole 534. The alignment member 510 is rotatable with respect to the second beam 508 due to the pin disposed in the attachment hole 534 and the slidable cooperation of mushroom pin 530 in slot 532. Accordingly, the alignment member 510 may remain aligned generally perpendicular to an axis of insertion of a flexible instrument, thereby also maintaining a generally axial alignment of the eyelets with respect to each other. Further, the eyelet on the alignment members 510 may receive different sized guides for different size catheters, thereby providing greater flexibility for procedures. For those embodiments where the eyelet is integrally attached to the alignment members 510, different sized alignment members may be used with support members 506 and 508.

The above arrangement of the anti-buckling mechanism 500 serve to prevent flexure through use of the long pins, while also allowing eyelet rotation to occur as the anti-buckling device 500 moves from an expanded configuration to a compressed configuration so as to keep the eyelets aligned to an axis of insertion. Accordingly, increased guidance capabilities, as well as increased buckle resistance (of the flexible instrument) may be achieved.

Further, as the exemplary illustrations provided herein use fewer components than traditional anti-buckling mechanisms (i.e. only two main support members and the alignment member), a reduced part count leads to lower manufacturing costs, as well as ease of assembly.

Figure 17:
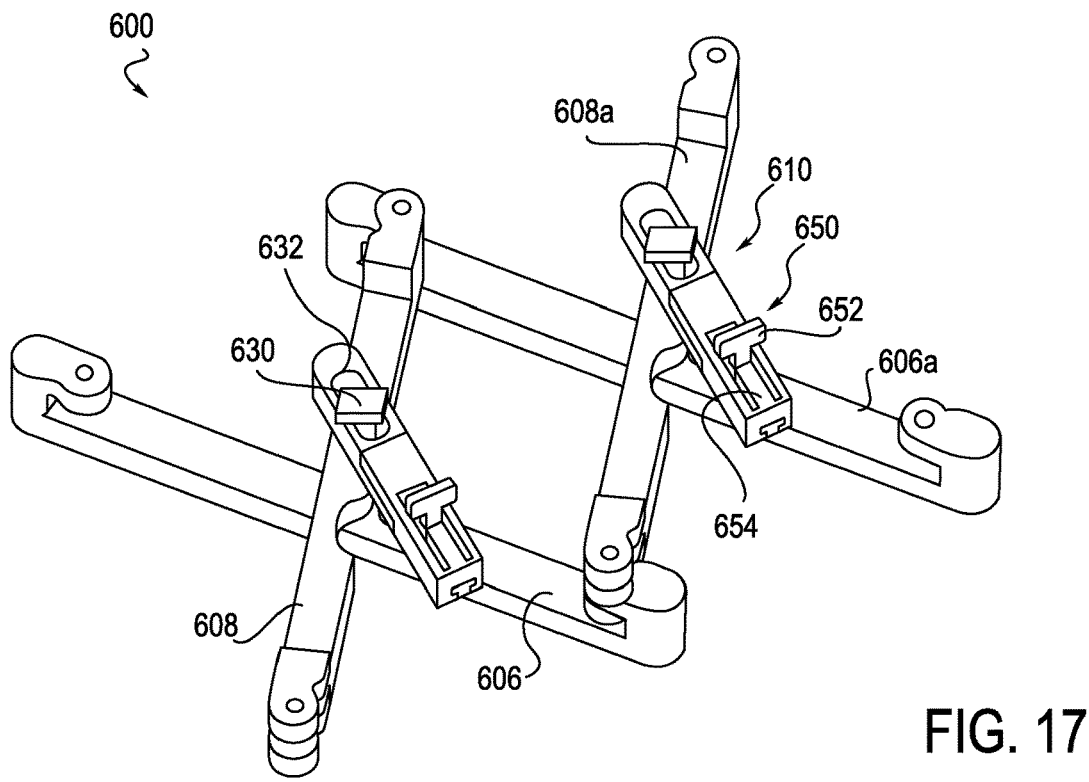
FIG. 17 is a perspective view of an exemplary anti-buckling mechanism with a slider, which may be used with a robotically controlled surgical system, according to another alternative embodiment.

Another alternative embodiment of an anti-buckling mechanism 600 is illustrated in FIG. 17. The anti-buckling mechanism 600 is similar to the anti-buckling mechanism 500 in that it includes first and second support members 606, 608 and an alignment member 610, respectively. The first and second support members 606, 608 and alignment member 610 are connected together in the same manner as discussed above in connection with the anti-buckling mechanism 500, for example the alignment member 610 includes a slot 632 for receiving mushroom pin 630. However, alignment member 610 further includes a slider mechanism 650 on top of the alignment member 610. In one exemplary arrangement, slider mechanism 650 has a catching latch 652 and a living hinge 654 that cooperate to pull back slider mechanism 650 and expose an open channel (not shown) through alignment member 610 to place a catheter. More specifically, slider mechanism 650 is configured to allow the anti-buckling mechanism 600 to be placed over a catheter or removed from a catheter during a procedure, such as to allow for more insertion of a catheter when the anti-buckling mechanism 600 is in its collapsed configuration and close to the insertion site. This selective removal feature eliminates wasted insertion length and negates having to remove the catheter from the patient's body to remove the anti-buckling mechanism 600. Further, this feature also permits the catheter to be inserted into the patient in the beginning of a procedure, and then loading an anti-buckling mechanism onto the catheter.

Figure 18:
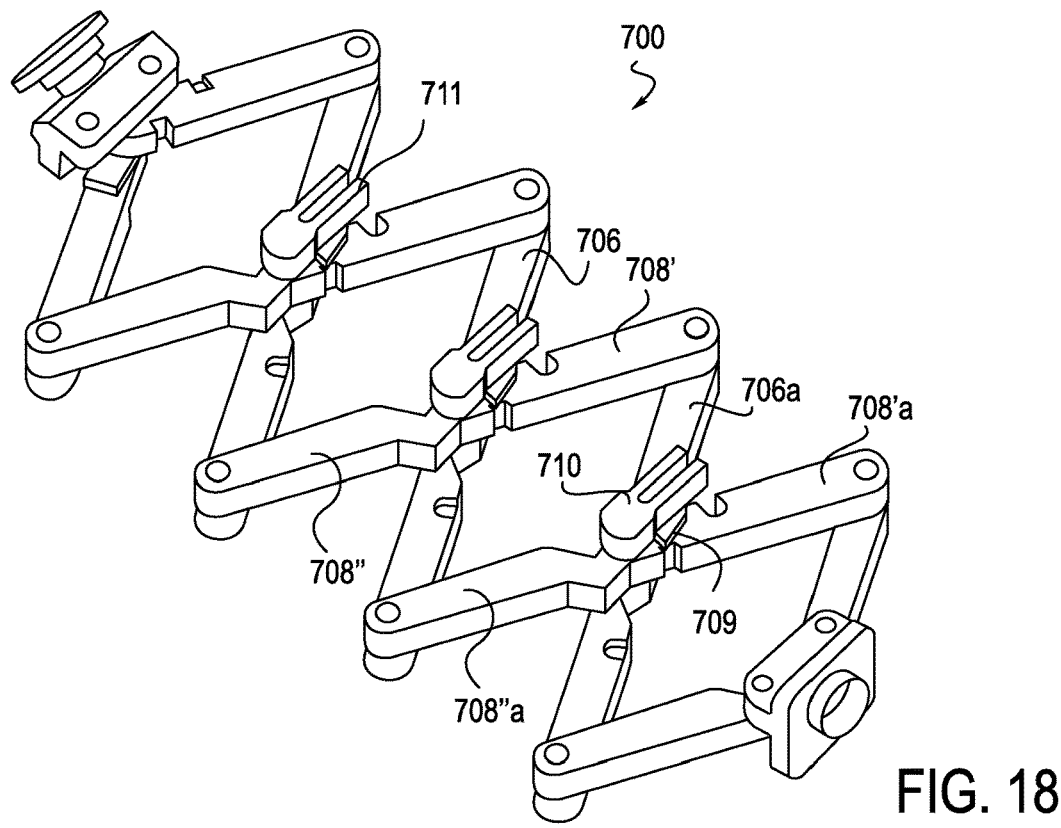
FIG. 18 is a perspective view of an exemplary anti-buckling mechanism with a pinned connection, which may be used with a robotically controlled surgical system, according to another alternative embodiment.

Another alternative embodiment of an anti-buckling device 700 is shown in FIG. 18. Anti-buckling device 700 includes multiple cooperating support members 706, 708 and an alignment member 710. One end of the first support member 706 is connected via a hinge to one of the second support members 708 and a second end of the first support member 706 is connected via a hinge to an adjacent second support member 708a. Alignment member 710 pivots on support member 708. The slot 711 on the alignment member 710 engages with a post (not shown) on support member 706 to maintain alignment member 710 rotationally constrained as the support members expand and contract. An elongate flexible instrument would pass through eyelets or apertures 709 on the alignment member 710.

Figure 19:
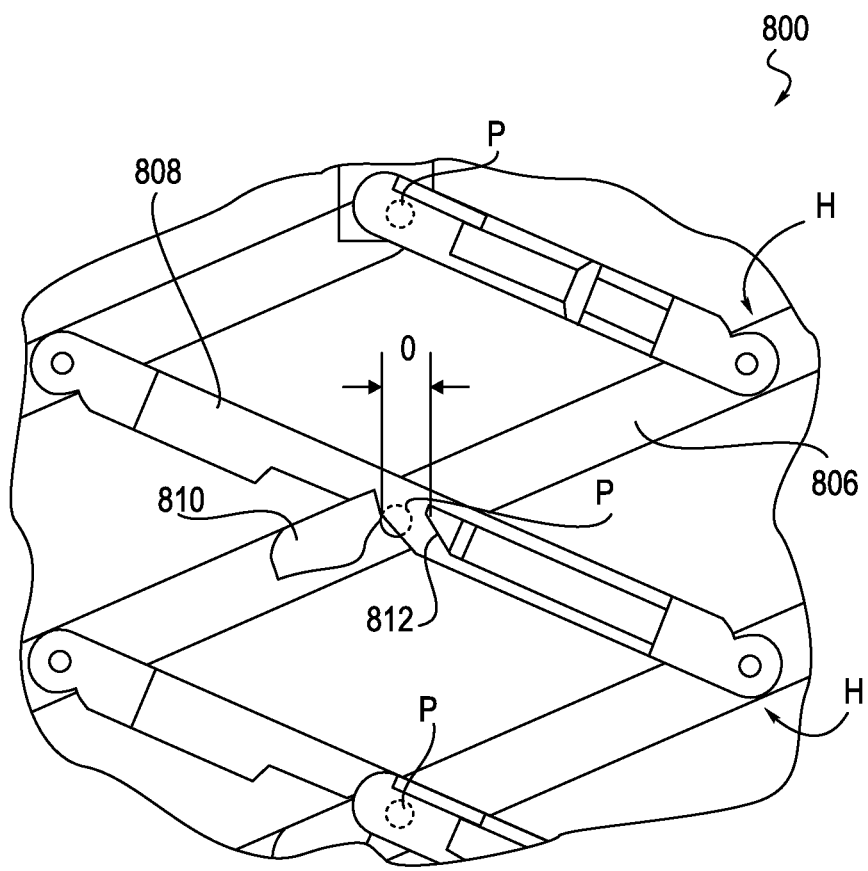
FIG. 19 is a partial top view of an anti-buckling mechanism with a variable eyelet, which may be used with a robotically controlled surgical system, according to one embodiment.
Figure 20:
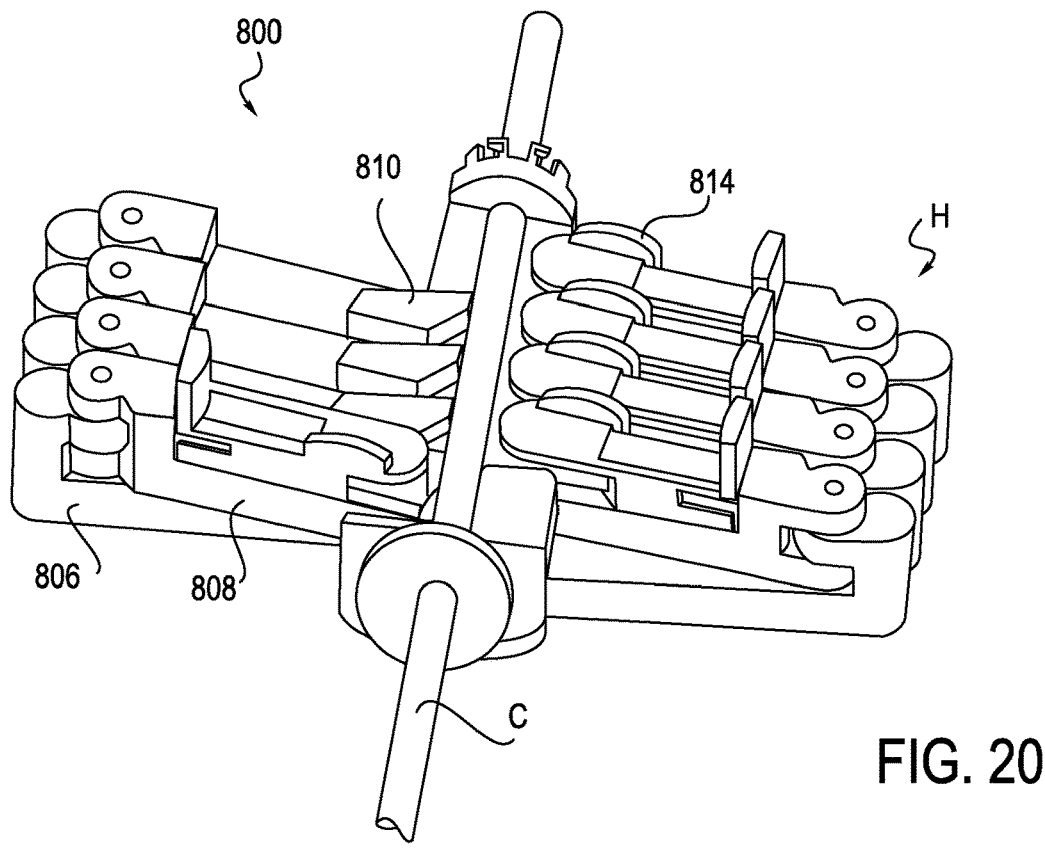
FIGS. 20 and 21 are perspective views of the anti-buckling mechanism of FIG. 19.
Figure 21:
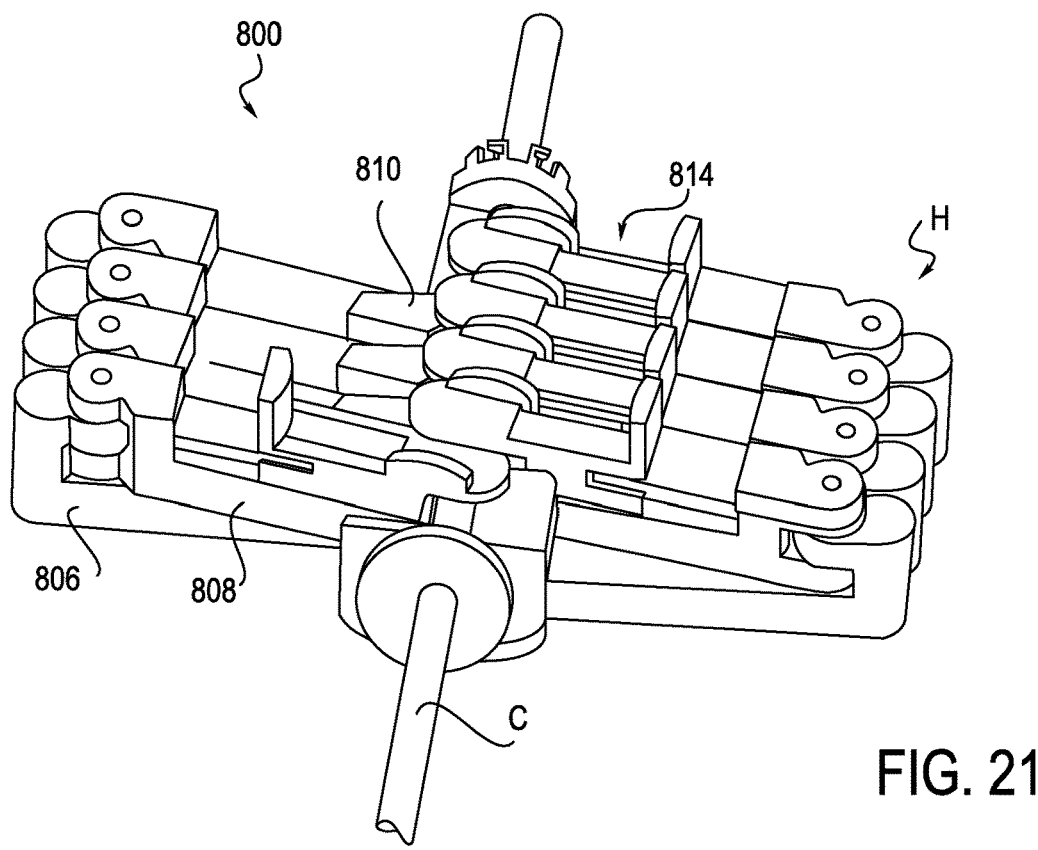

A further exemplary embodiment of an anti-buckling device 800 is shown in FIGS. 19-21. The anti-buckling mechanism 800 is similar in some respects to anti-buckling mechanism 500 and 600, in that both use a dual support member configuration with a center pivot point P and tapered pin exterior hinges H, as described above in connection with anti-buckling mechanism 500 as shown in FIG. 16. However, instead of a separate eyelet, the anti-buckling mechanism 800 uses openings O in the center part of the support members 808 to form an eyelet. The opening O may be shaped to keep the most engagement of the catheter for support of a given catheter dimension.

More specifically, looking at FIG. 19, anti-buckling mechanism 800 includes first and second support members 806, 808, connected in the manner described above in connection with anti-buckling mechanism 500. A first raised land member 810 and second raised land member 812 are mounted to the support member 808 and form a channel or opening O therebetween. A slider 814 can slide on support member 808 to close the channel or opening O. As the first and second support members 806, 808 pivot about pivot point P, they combine to provide a support frame for catheter C which may be disposed within, as shown in FIGS. 20 and 21. Using just the first and second support members 806, 808 serves to reduce the number of parts, thereby reducing assembly time and cost associated with making and assembling the anti-buckling mechanism 800.

In FIG. 20, sliders 814 are in an open position, which allows selective removal of the anti-buckling mechanism 800 during a procedure, or top loading of a catheter. In FIG. 21, sliders 814 are positioned in a closed position. Yet another alternative to design in FIG. 19 would be to provide a static cover that would be positioned over the variable opening O.

Figure 22:
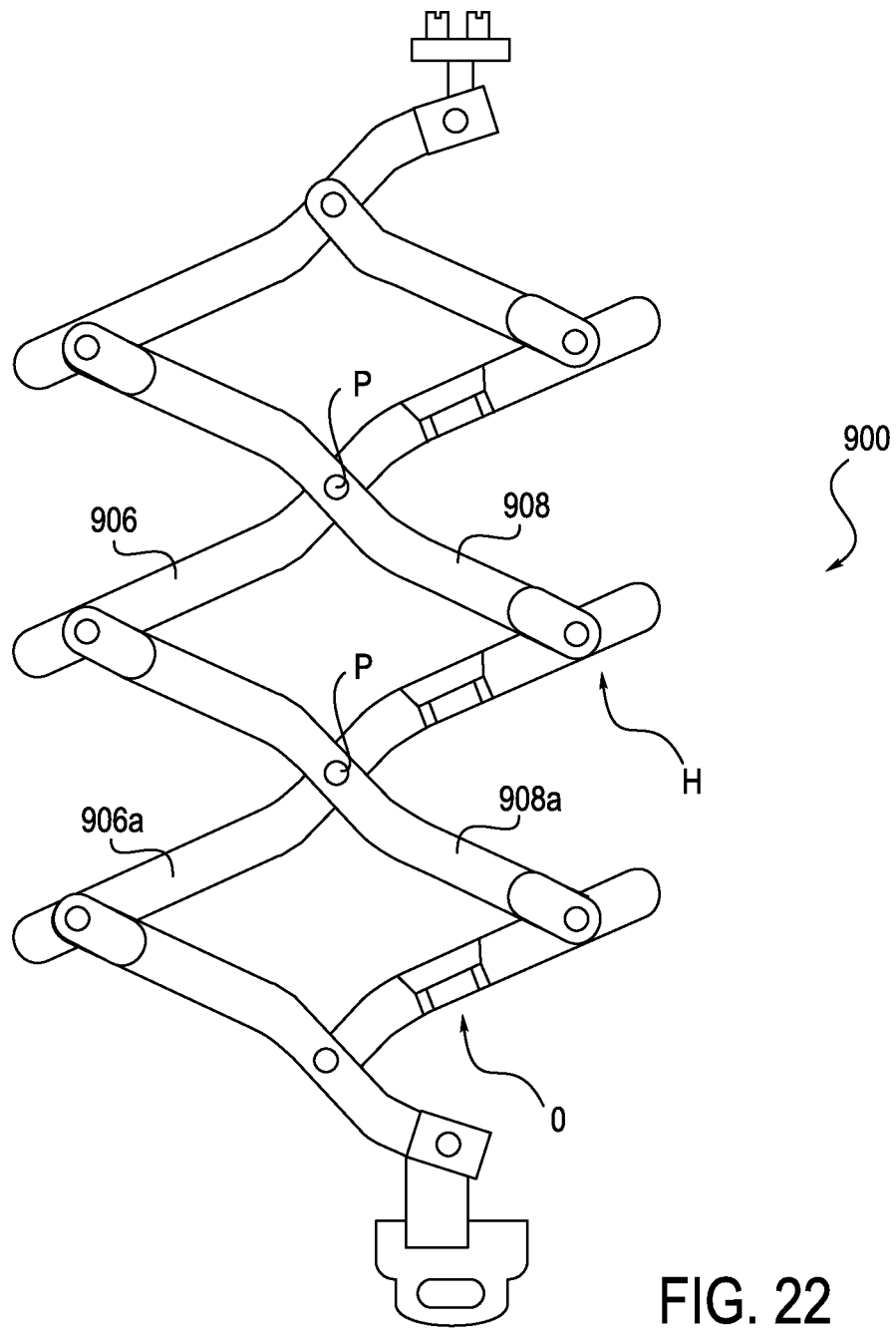
FIGS. 22-24 are top views of an anti-buckling mechanism with an offset variable eyelet, which may be used with a robotically controlled surgical system, according to one embodiment.
Figure 23:
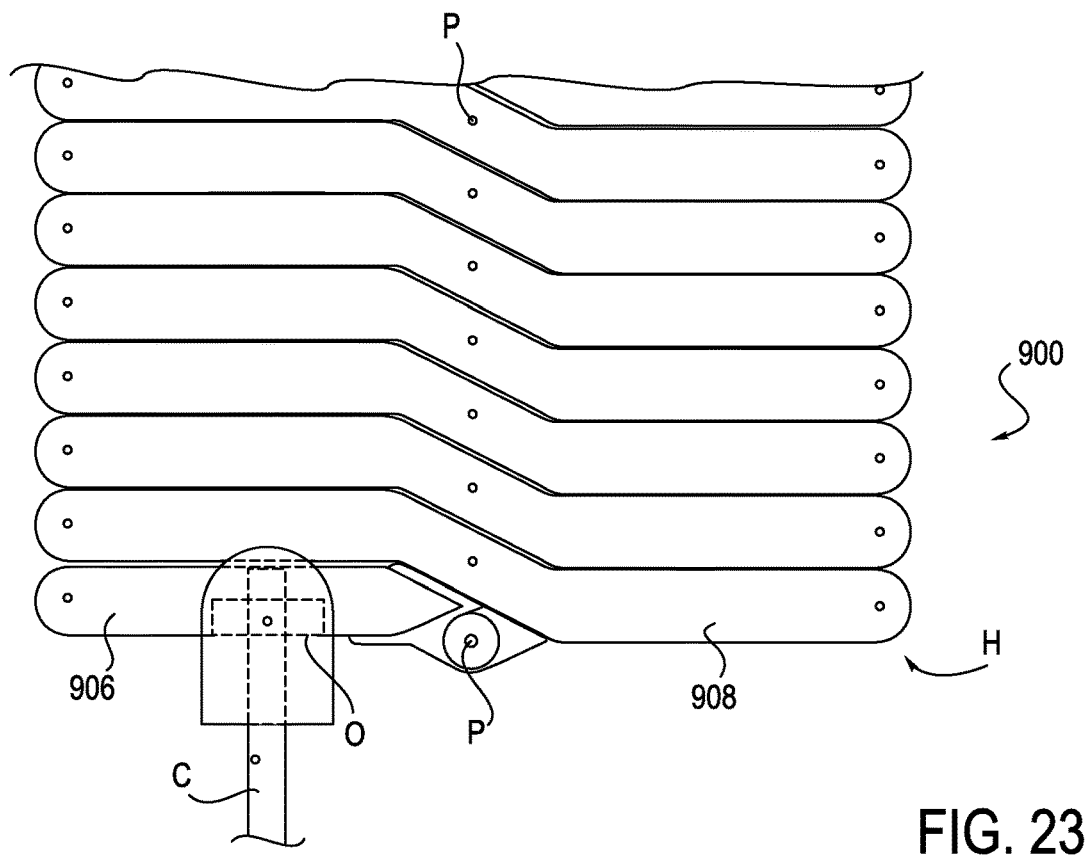
Figure 24:
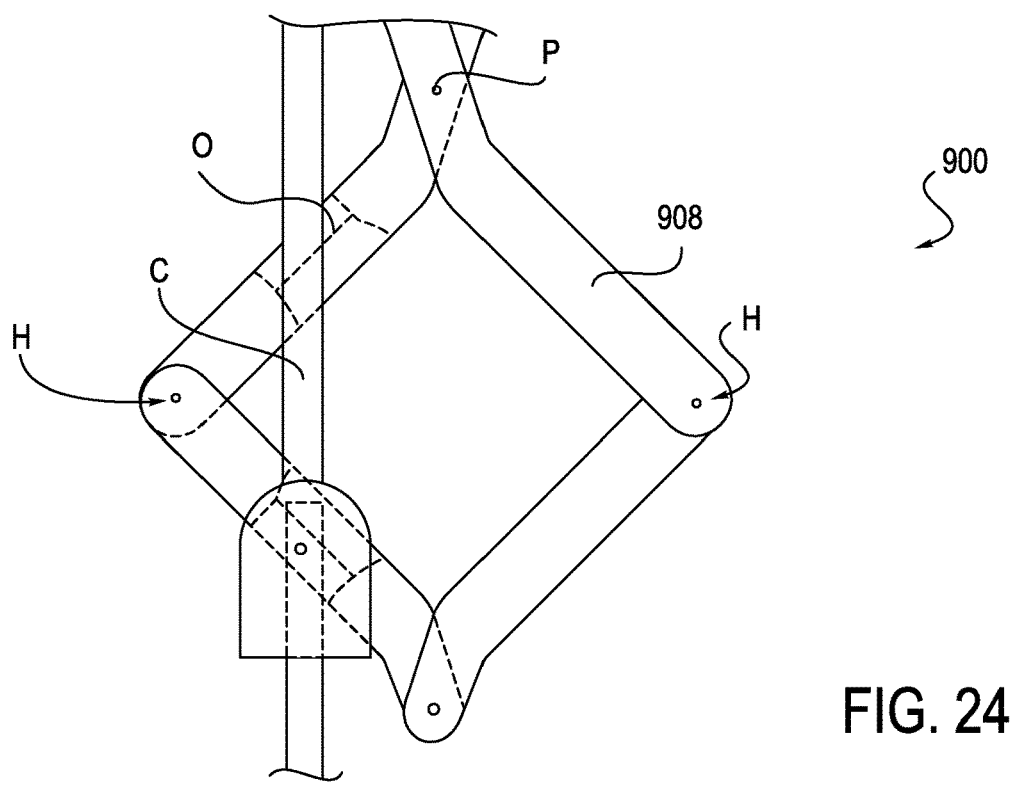

FIGS. 22-24 illustrate a further exemplary embodiment of an anti-buckling mechanism 900. Anti-buckling mechanism 900 is similar to anti-buckling mechanisms 500-800, as shown in FIGS. 16-21, in that anti-buckling mechanism 900 includes first and second support members 906, 908 that are pivotally connected together about a center pivot point P and are connected together to form external hinges H in the manner described above. In this arrangement, however, each of support members 906 includes an opening O extending therethrough. The opening O is positioned to be off-center to the pivot point P. As may be seen, when the anti-buckling mechanism 900 is collapsed, as shown in FIG. 23, all of the openings O of successively arranged support members 906 cooperate to form a channel for guiding a catheter C. Moreover, referring to FIGS. 22 and 24, when in an expanded configuration, the openings O still remain aligned with one another and are sufficiently large enough that catheter C may still extend through, aligned with an insertion site.

The configuration of FIGS. 22-24 provides double the support for the same number of support members of the configurations shown above in FIGS. 14-21. Increased support can be important in certain circumstances because buckling strength is inversely proportional to the square of unsupported length. As the openings O are arranged off-center to the central pivot point P, the openings O are similar to the variable eyelet configuration discussed above in connection with FIGS. 19-21, in that they are points of contact and do not provide a constant width.

The anti-buckling mechanism 900 decreases the space between support members 906, 908. Because this design provides increased support over other designs, the number of overall support members may be reduced. This configuration will therefore allow wasted length to be decreased if the catheter is fully inserted into the body. Because the buckle length is reduced, buckle resistance is increased.

Figure 25:
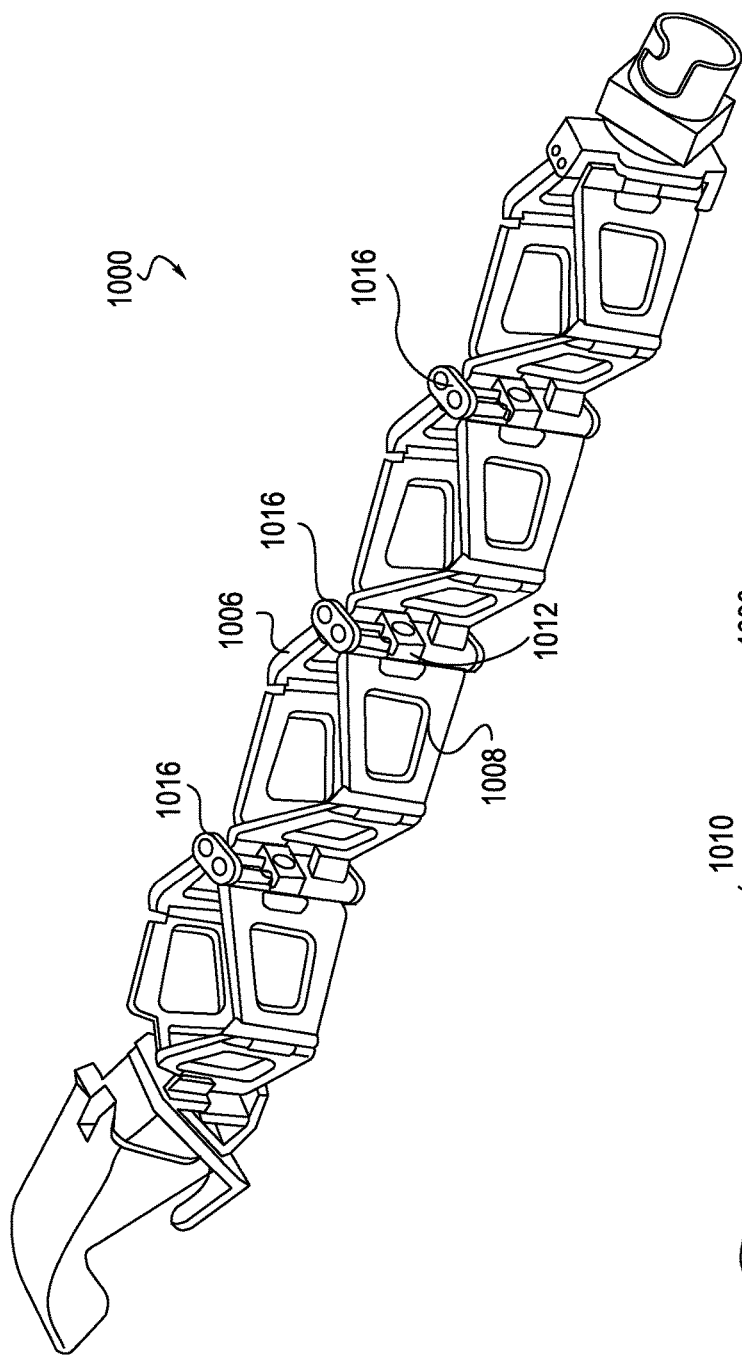
FIGS. 25 and 26 are perspective and partial cross-sectional views, respectively, of an anti-buckling mechanism with geared beams, which may be used with a robotically controlled surgical system, according to one embodiment.
Figure 26:
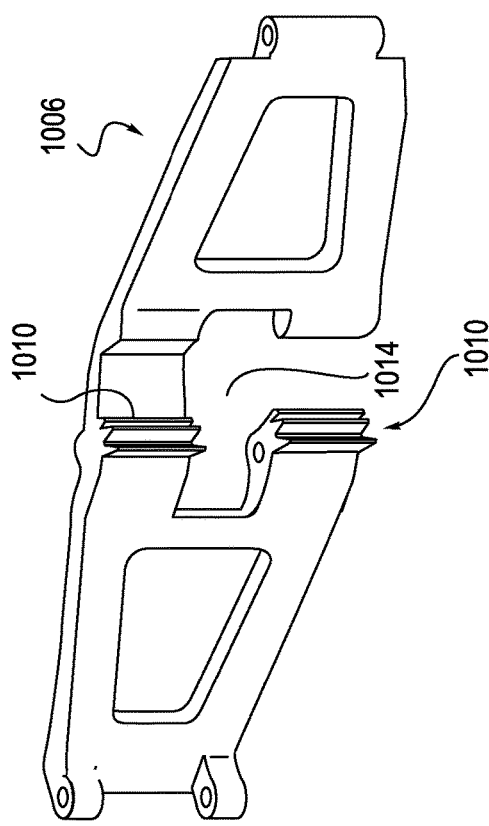

A final exemplary arrangement of an anti-buckling mechanism 1000 is shown in FIGS. 25 and 26. In this arrangement, dual beams 1006, 1008 are each provided with teeth 1010 which cooperate to facilitate extension and collapse of the beams 1006, 1008 in a manner similar to a gear. To ensure that the beams 1006, 1008 rotate symmetrically, the teeth 1010 are slightly offset, similar to a geared protractor. An eyelet 1012 is centered as openings in between the teeth 1010. As may be seen in FIG. 26, the teeth 1010 defined by each of the beams 1006, 1008 (only beam 1006 shown in FIG. 26) are spaced apart from one another leaving a gap 1014 into which eyelet 1012 may be disposed. The eyelets are parallel to the axis of insertion. In an alternative arrangement (not shown), eyelet 1012 may be placed on a top or bottom of a coupler 1016 of the gears 1010. Eyelets 1012 positioned on the top of the coupler may be fixed or having opening features (such as snap-on or sliders) to enable anti-buckling mechanism 1000 to be added or removed during a procedure.

The anti-buckling mechanism 1000 keeps eyelets 1012 centered, increasing buckling resistance, reduces part count, and eases assembly with use of locking features. While the cooperating teeth are only shown at the center of the beam interaction, it is understood that gears may also be used at the outer hinges, and there may be more center gears employed than the gears 1010 shown, as well as concentric gears.

In some embodiments, exemplary anti-buckling supports may be integrated within an instrument driver or remote catheter manipulator (RCM). As shown in FIGS. 27-39, an exemplary anti-buckling support assembly 2820 is illustrated integrated into an exemplary RCM 2800. The RCM 2800 may be employed in conjunction with any catheter system, for example similar to the instrument driver 16 as described above in system (S) in FIGS. 1A-1C.

Figure 27:
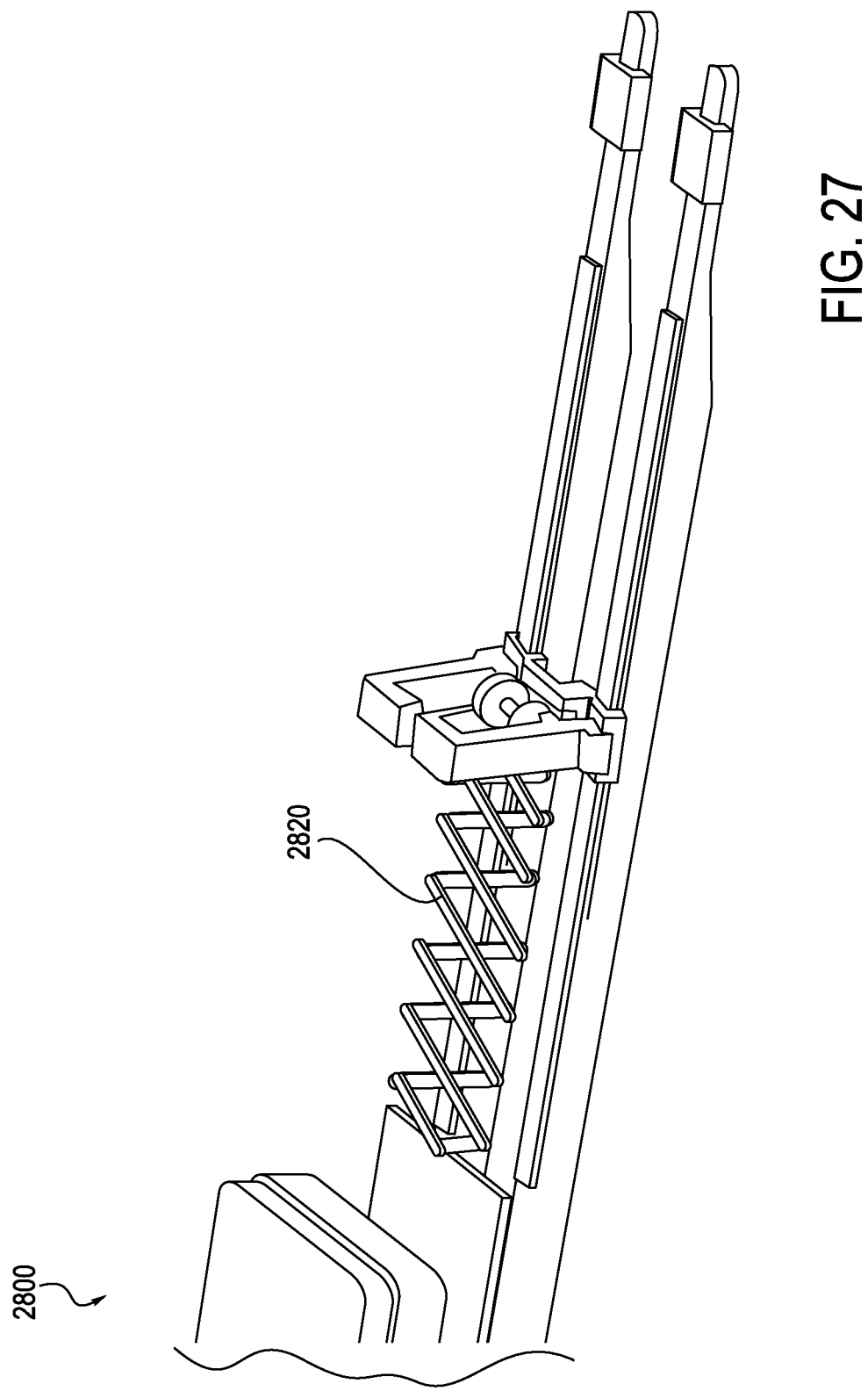
FIG. 27 is a cutaway perspective view of an exemplary instrument driver having an anti-buckling support incorporated within the driver, according to one embodiment.
Figure 35:
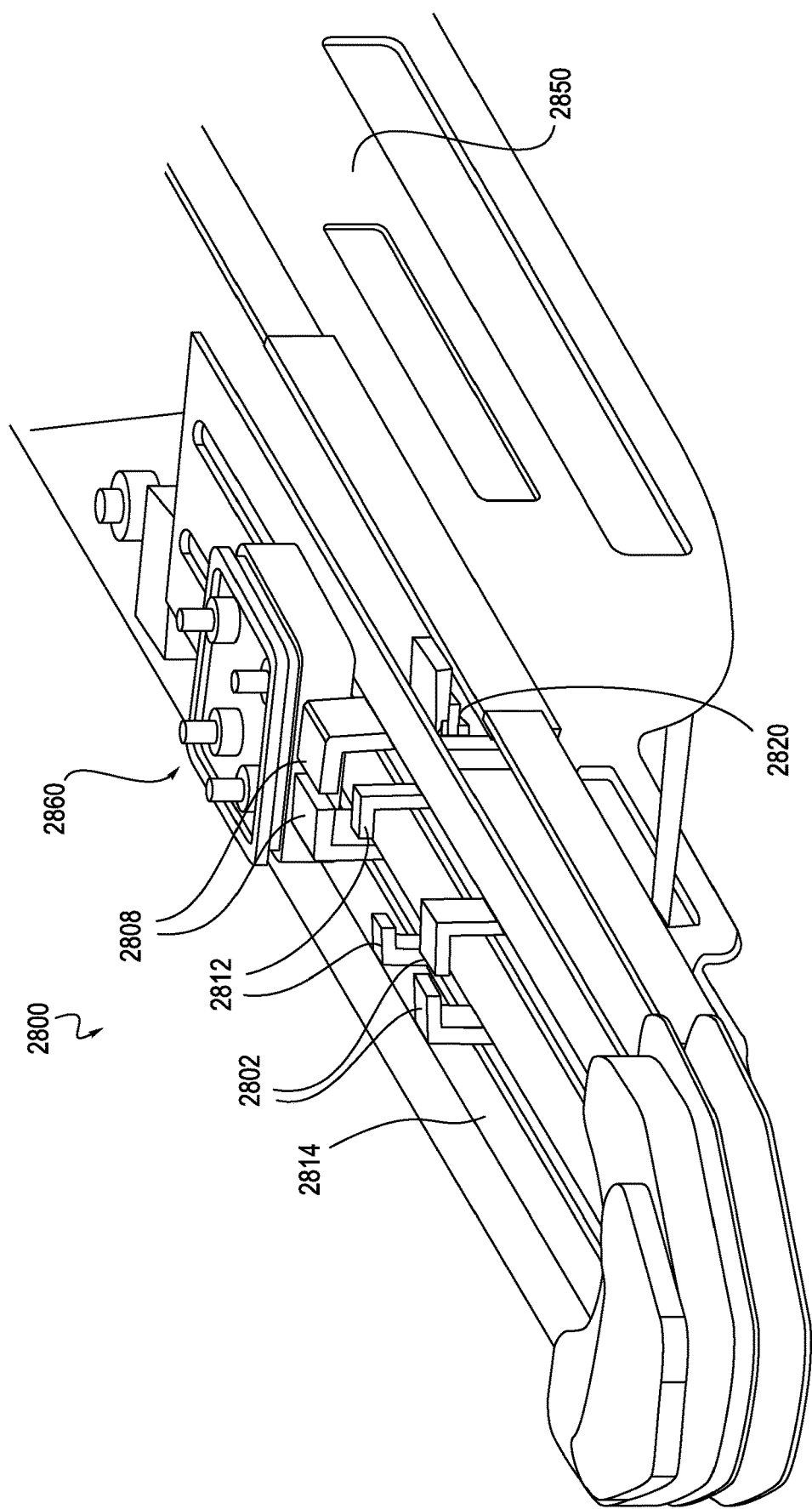
FIG. 35 is a perspective view of the exemplary instrument driver of FIG. 27, illustrating the upper deck and external cover, according to one embodiment.
Figure 36:
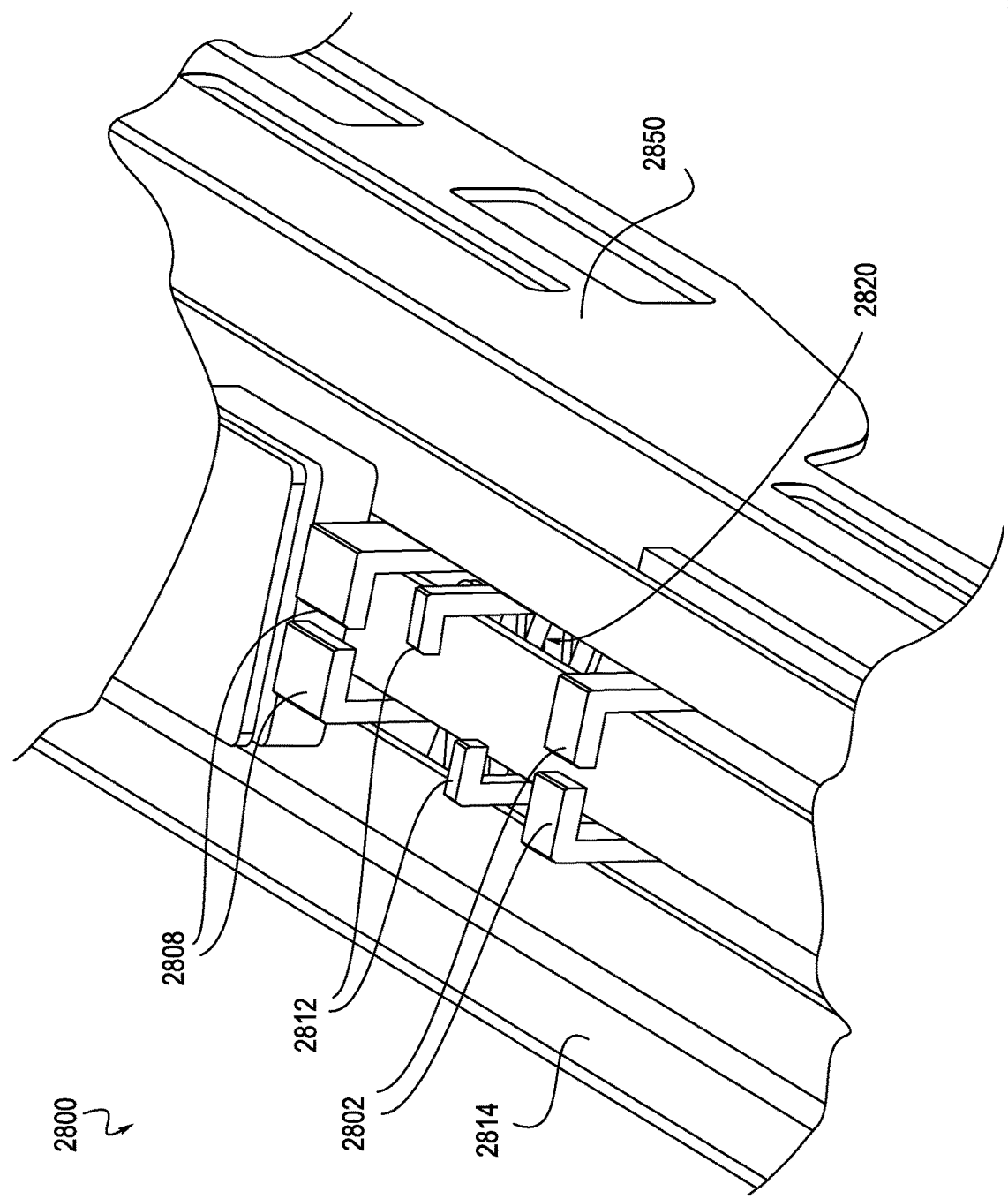
FIG. 36 is an enlarged perspective view of the exemplary instrument driver of FIG. 27, illustrating the upper deck and external cover, according to one embodiment.

As shown in FIGS. 27, 35 and 36, the RCM 2800 may include one or more anti-buckling supports, in this case scissor mechanism 2820, which is generally incorporated internally to the RCM 2800. In this manner, the scissor mechanism 2820 is placed outside of the sterile field, and does not need to be replaced after each procedure. More specifically, the RCM 2800 includes a top deck 2814 and cover 2850, which generally define an outer cover of the RCM 2800. A sterile drape may be laid over the deck 2814 or interfaced with supports 2808, 2802, and 2812. The supports 2808, 2802, 2812 may interface with an elongate member (not shown) in order to provide anti-buckling support to the elongate member. In this manner, the supports 2808, 2802, 2812 each translate the lateral support of the scissor mechanism 2820 across the sterile boundary to the elongate member. The supports 2808, 2802, 2812 may directly interface with the elongate member or may provide the mounting locations where a one-piece, foldable structure anti-buckling mechanism may attach, as will be described in further detail below in connection with FIG. 38. The RCM 2800 may include a splayer interface 2860 configured to drive a splayer associated with the elongate member. It should be noted that the alternative anti-buckling support structures such as that shown in FIGS. 37-40 may also be used instead of scissor mechanism 2820.

Figure 28:
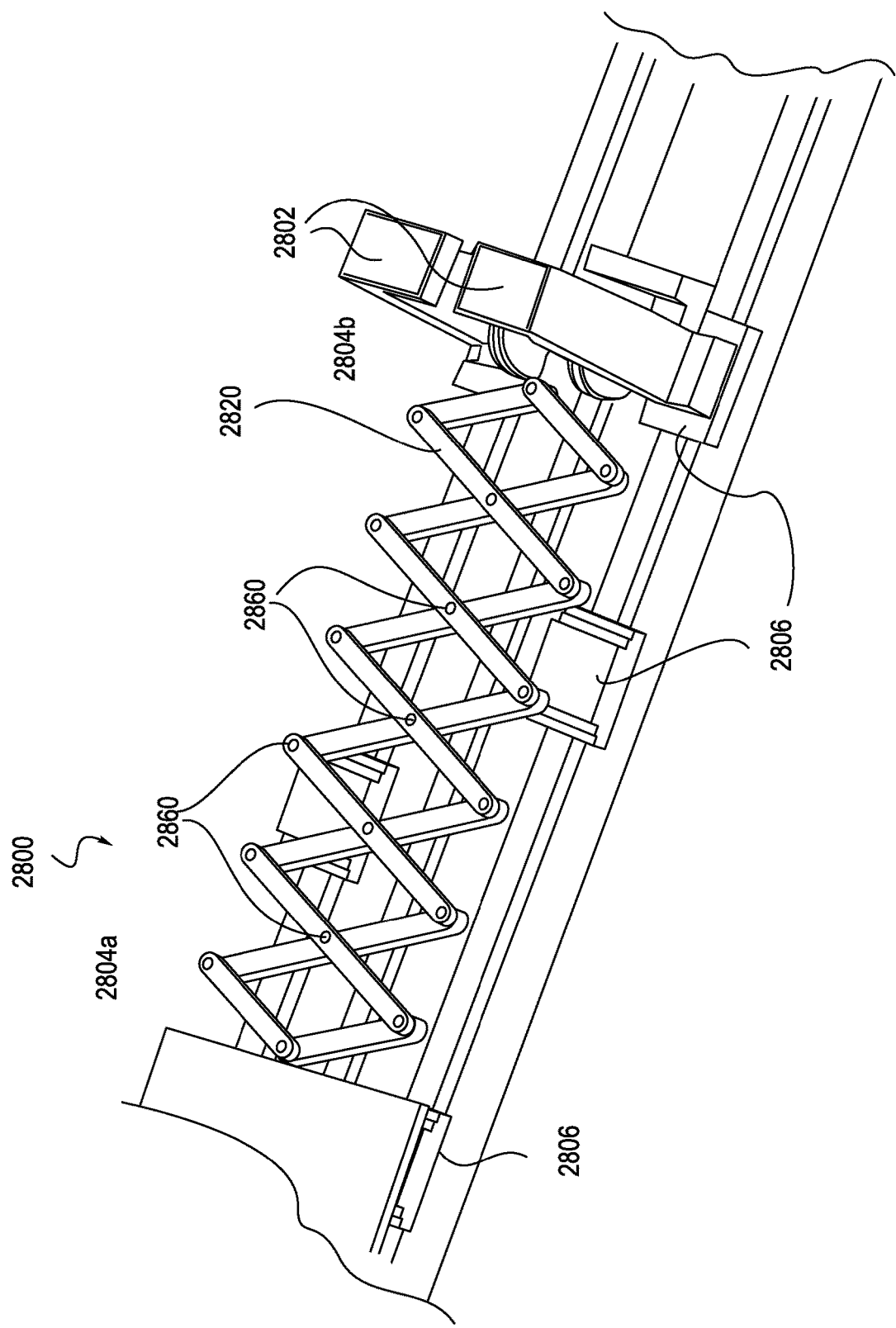
FIG. 28 is an enlarged view of the cutaway of the exemplary instrument driver of FIG. 27, according to one embodiment.
Figure 29:
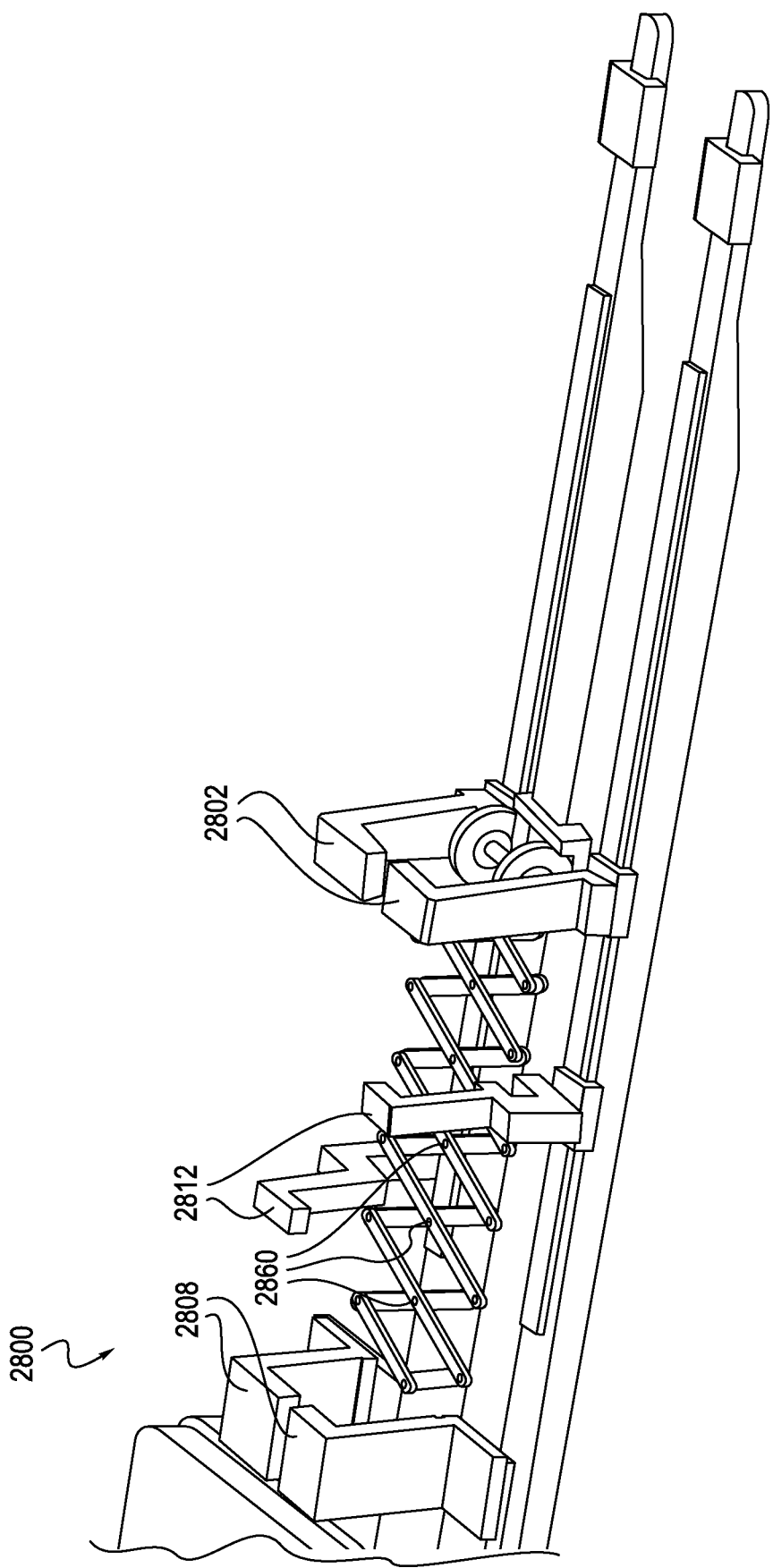
FIG. 29 is another cutaway perspective view of the exemplary instrument driver of FIG. 27, according to one embodiment.

Turning now to FIGS. 27-34, internal construction of the exemplary RCM 2800 is explained in further detail. The RCM 2800 includes a catheter mounting plate 2804a and idler mounting plate 2804b, which are illustrated in a partially retracted position in FIG. 27. An anti-buckling support, here a scissor mechanism 2820, is integrated within the RCM 2800 and may connect to both carriages 2804, for example connecting catheter mounting plate 2804a to idler mounting plate 2804b. A similar anti-buckling support, for example a scissor mechanism, could be mounted forward of the idler mounting plate 2804b, attaching to a sheath mounting plate assembly (or carriage if designed to move independently). As shown in FIG. 28, the idler mounting plate 2804b may travel in connection with the catheter mounting plate 2804a. For example, translation of the idler mounting plate 2804b may occur at a 1:2 ratio with respect to the catheter mounting plate 2804a. Idler mounting plate 2804b employs linear bearings 2806 mounted to linear shafts, which also support the catheter mounting plate 2804a. The idler mounting plate 2804b could be designed such that portions of the mounting plate 2804b extend above a deck 2814 (which may generally function as a top cover) of the RCM 2800, similar to the catheter mounting plate. Additionally, the idler mounting plate 2804b may be positioned such that associated risers 2808, 2812, and 2802, which are configured to carry an elongate member, for example a catheter, are positioned near the center of the catheter mounting plate and sheath mounting plate, as shown in FIG. 29. The support risers 2802 extend upwards above the deck 2814. In this manner, the idler mounting plate 2804*b* may translate at a 50% rate with respect to the catheter mounting plate 2804*a*. A sterile drape (not shown) may interface with the RCM 2800 at the riser portions 2812 of the idler mounting plate 2804*b*, assuring that the center of the drape travels at the same 1:2 ratio as the catheter mounting plate 2804*a*. A catheter eyelet bushing (not shown) may be mounted to an external surface of the drape at the idler mounting plate interface, thus reducing the buckle distance by 50%. Additional mini-carriages with similar riser features can be inserted between the idler mounting plate and the catheter mounting plate, and between the idler mounting plate and the sheath mounting plate. These would provide the disposable's mounting support at each eyelet, second eyelet, or each third eyelet as will be described below in connection with FIGS. 37-39.

Turning now to FIG. 29, catheter mounting plate support risers 2808 are provided, along with intermediate carriages with anti-buckling support risers shown 2812. In this example, the support risers 2812 are coupled to every second scissor cross pivot point 2860. In other exemplary approaches, support risers 2812 may be aligned together (coupled directly together). In the approach illustrated, a higher density of contact points to support the anti-buckling device eyelets is achieved, without increasing the linear length requirements.

Figure 30:
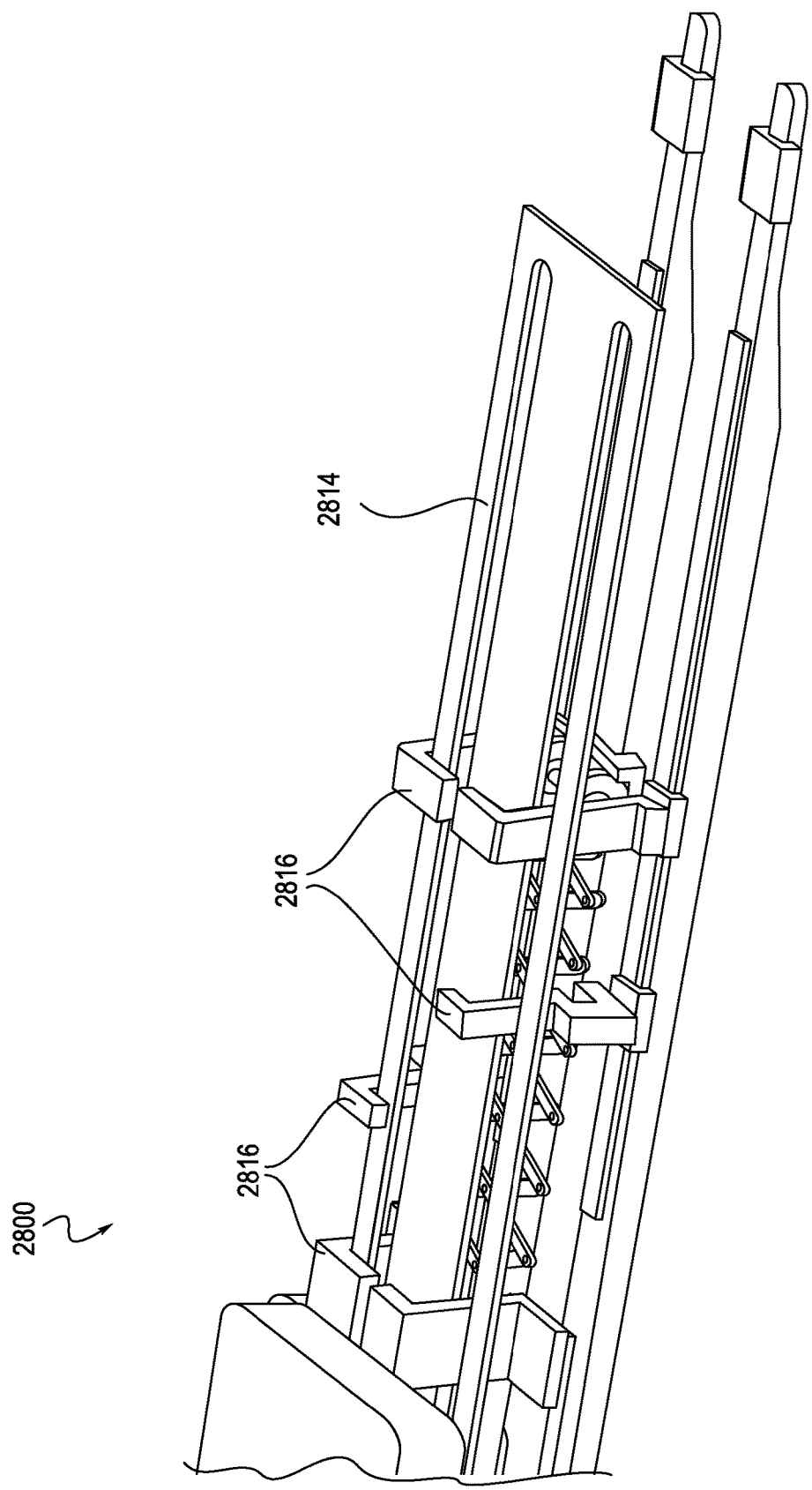
FIG. 30 is another cutaway perspective view of the exemplary instrument driver of FIG. 27, including an upper deck, according to one embodiment.
Figure 31:
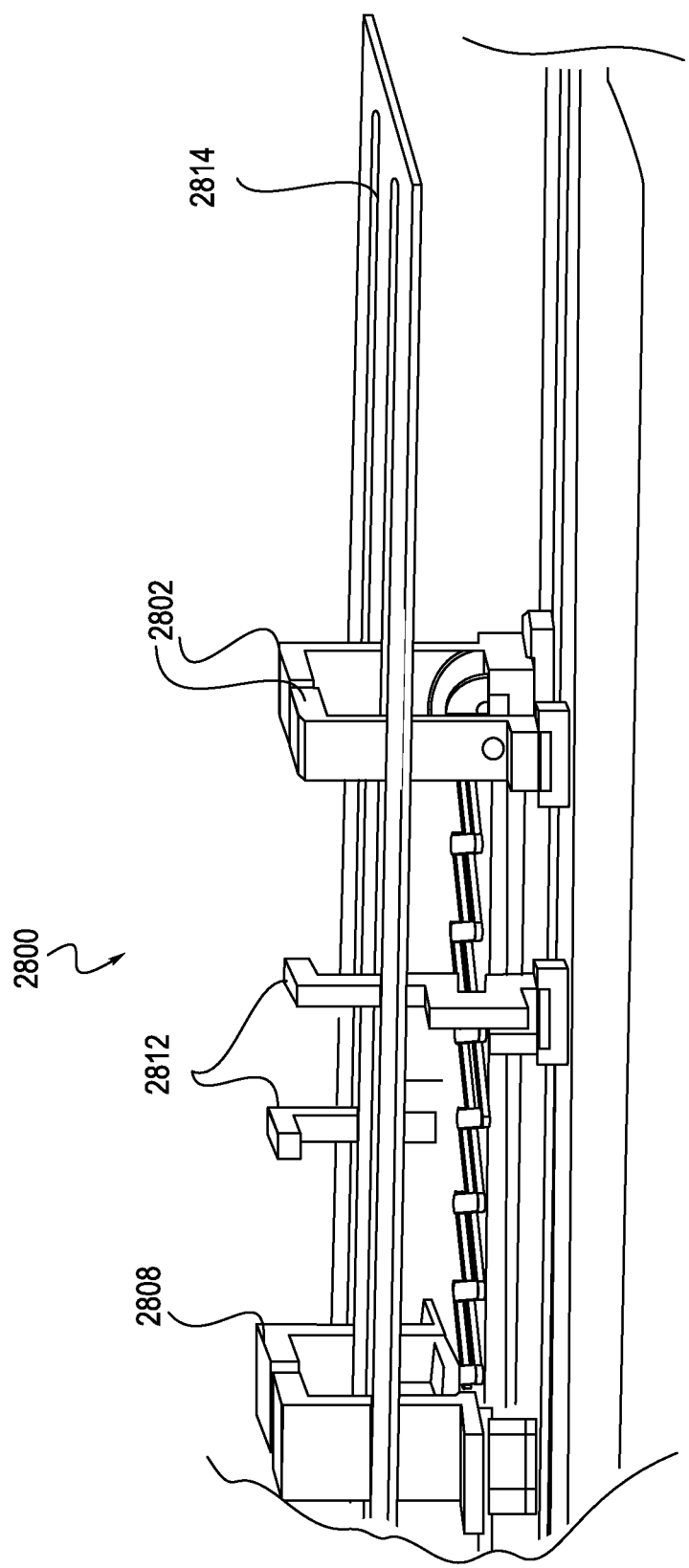
FIG. 31 is another cutaway perspective view of the exemplary instrument driver of FIG. 27, illustrating another view of an upper deck, according to one embodiment.

Referring to FIGS. 30 and 31, the deck (i.e. top cover plate) 2814 is illustrated. Upon installation of the deck 2814, only the eyelets 2816 of the riser supports are visible above the deck 2814. In this manner, an elongate member may be received within the eyelet supports 2816 such that the elongate member is supported above the deck 2814, for example outside of the RCM 2800, and within the sterile filed. Accordingly, a sterile drape may generally be supported by the deck 2814. It should be noted that an additional anti-buckling support, for example scissor mechanism 2820, may typically be provided with dedicated support risers in front of the mechanism 2820 (i.e. the right in FIG. 30), between the idler mounting plate and the sheath (bearing blocks shown). As shown in FIG. 31, the support risers 2802, 2808, 2812 are generally positioned at the same height as the guide mounting plate, so the sterile drape will sit flat, for example upon the deck 2814.

Figure 32:
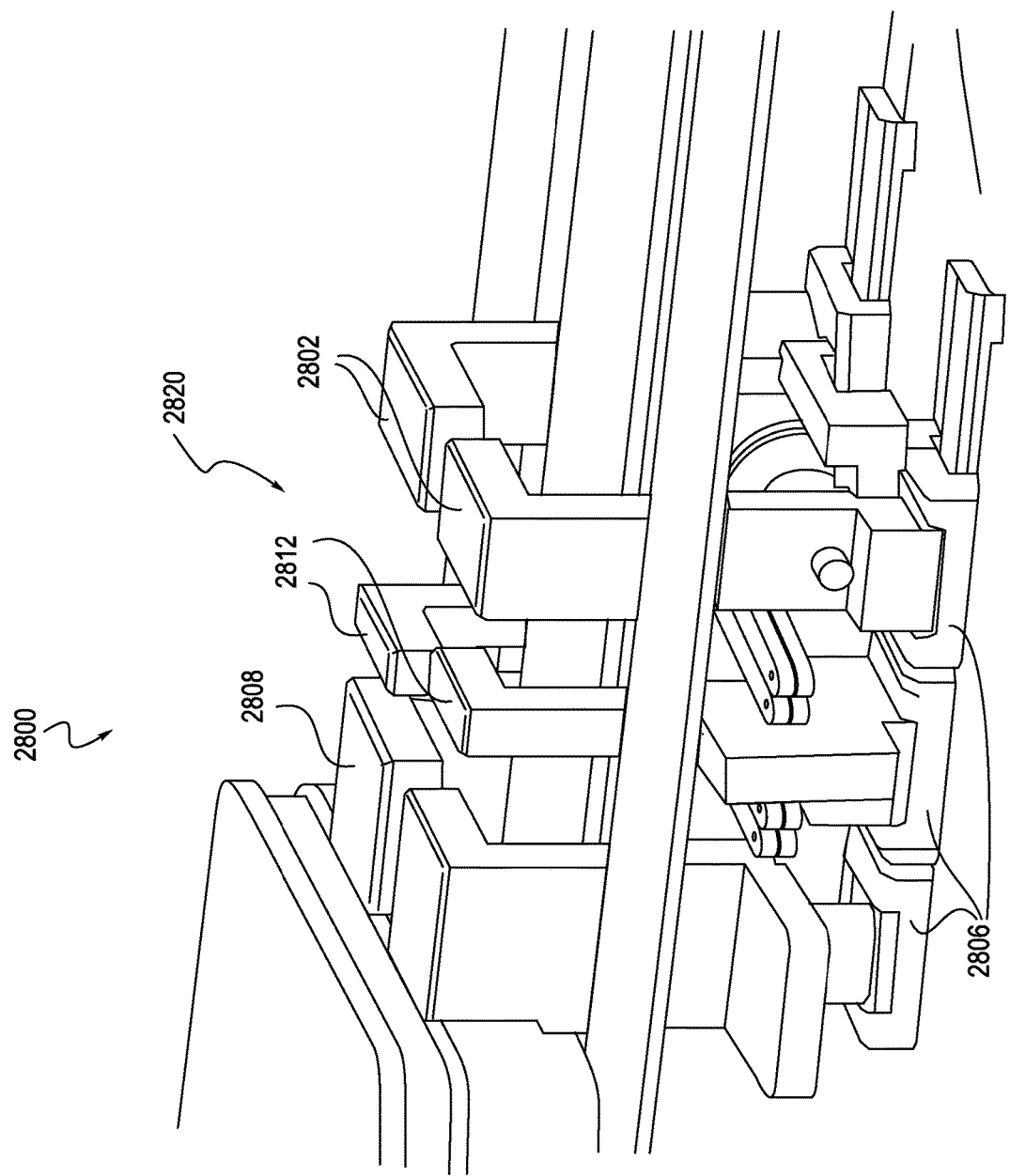
FIG. 32 is another cutaway perspective view of the exemplary instrument driver of FIG. 27, providing an enlarged view of a retracted anti-buckling mechanism within the instrument driver, according to one embodiment.
Figure 33:
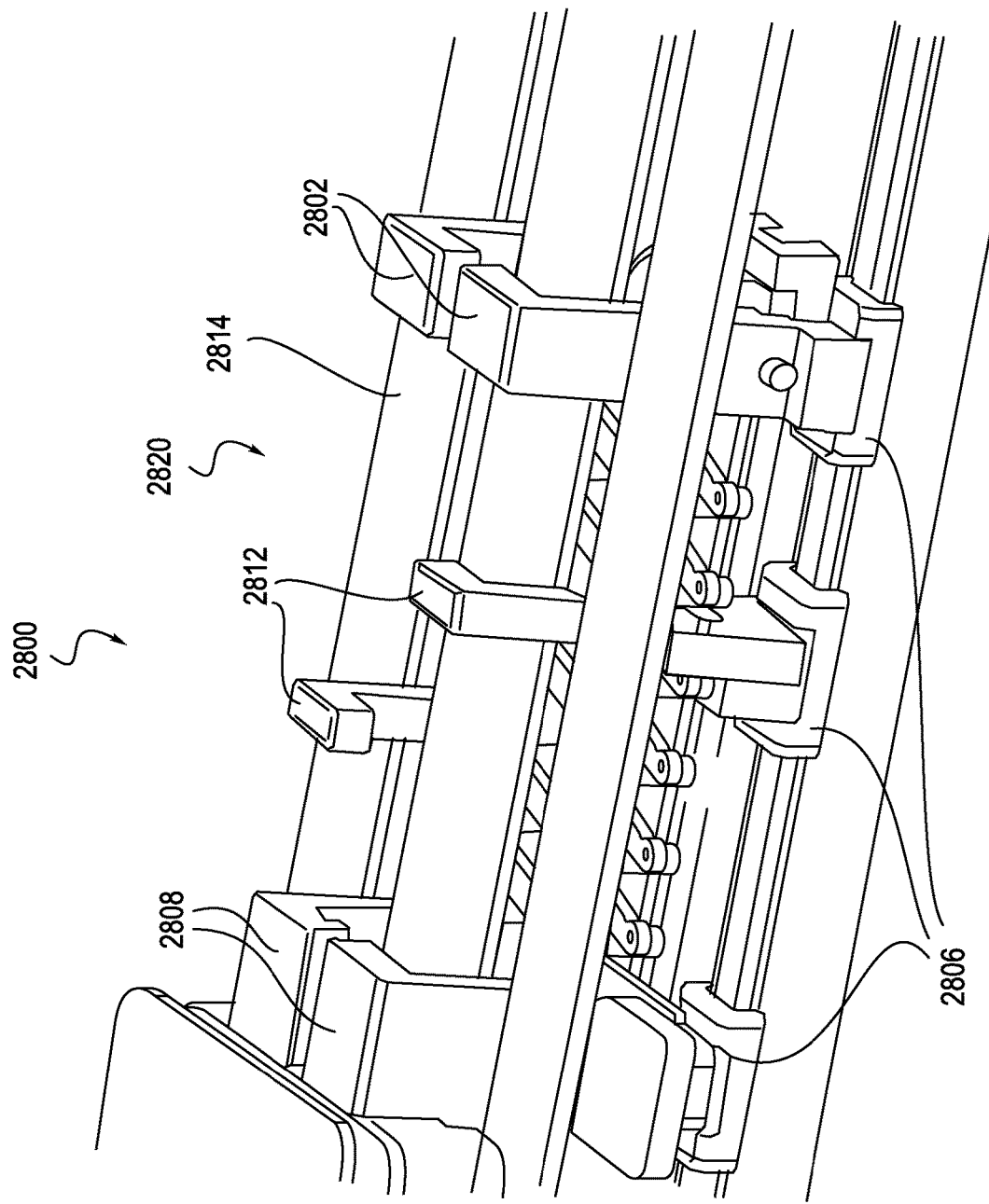
FIG. 33 is another cutaway perspective view of the exemplary instrument driver of FIG. 27, providing an enlarged view of a partially extended anti-buckling mechanism within the instrument driver, according to one embodiment.
Figure 34:
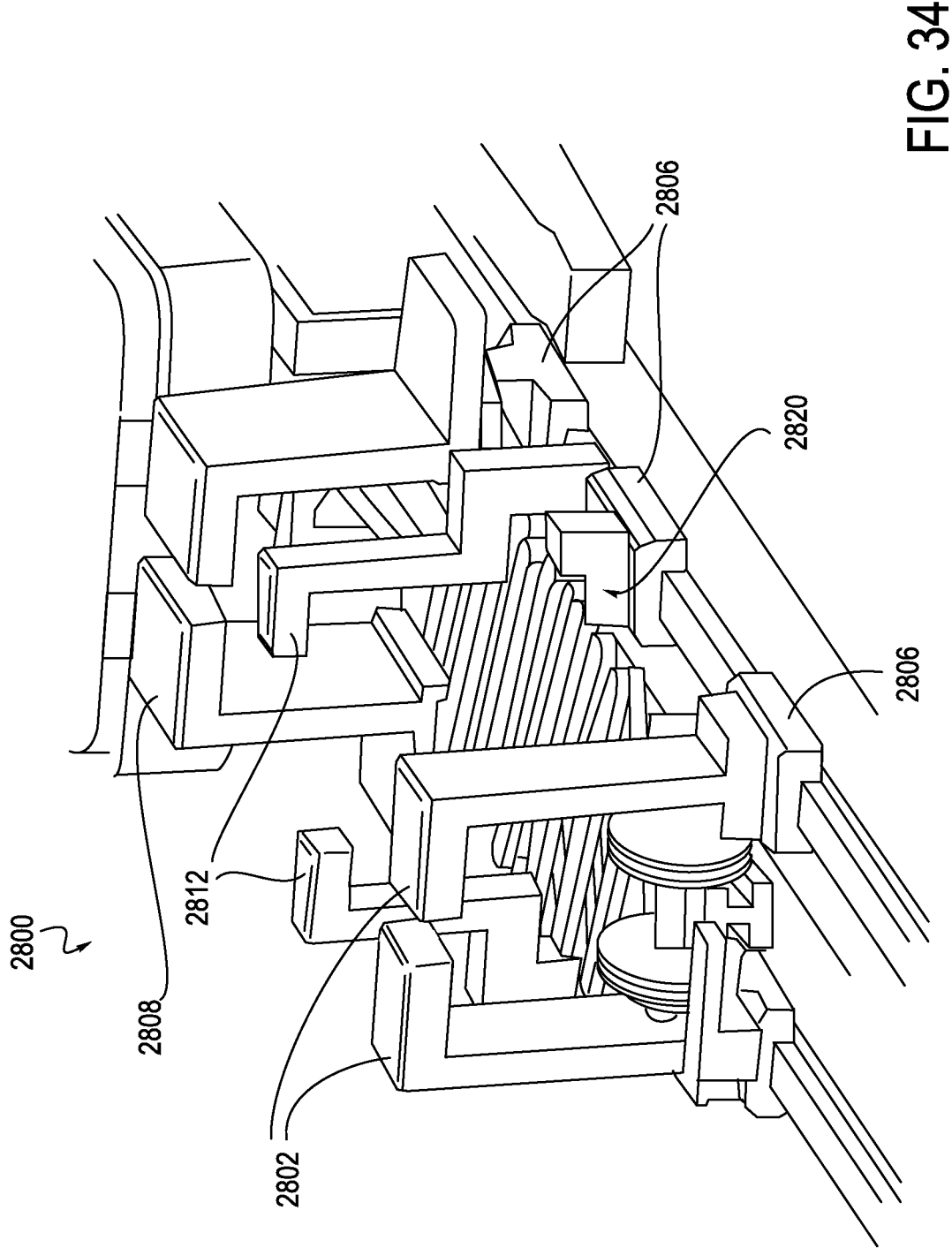
FIG. 34 is another cutaway perspective view of the exemplary instrument driver of FIG. 27, providing an enlarged view of the retracted anti-buckling mechanism within the instrument driver, according to one embodiment.

Turning now to FIGS. 32-34, movement of the scissor assembly 2820 within the RCM 2800 is illustrated in further detail. As shown in FIGS. 32 and 34, the RCM 2800 is illustrated with the catheter and idler mounting plates 2806 in a fully extended, for example full catheter insertion, position. The scissor assembly 2820 is fully compressed, and the bearing blocks 2806 are almost in contact with each other. The mini-carriage bearing blocks 2806 are aligned, however the risers 2802, 2808, 2812 are designed with forwards/backwards offsets, for example in an axial direction or parallel to the direction of movement of the bearing blocks 2806, to enable attachment of different eyelet positions to the elongate member (not shown in FIG. 32). As shown in FIG. 33, the catheter and idler mounting plates 2806 may be extended away from one another, for example as insertion of the elongate member occurs, thereby providing anti-buckling support to an elongate member (not shown in FIGS. 32-34).

Accordion-Like Anti-Buckling Mechanisms

Figure 37:
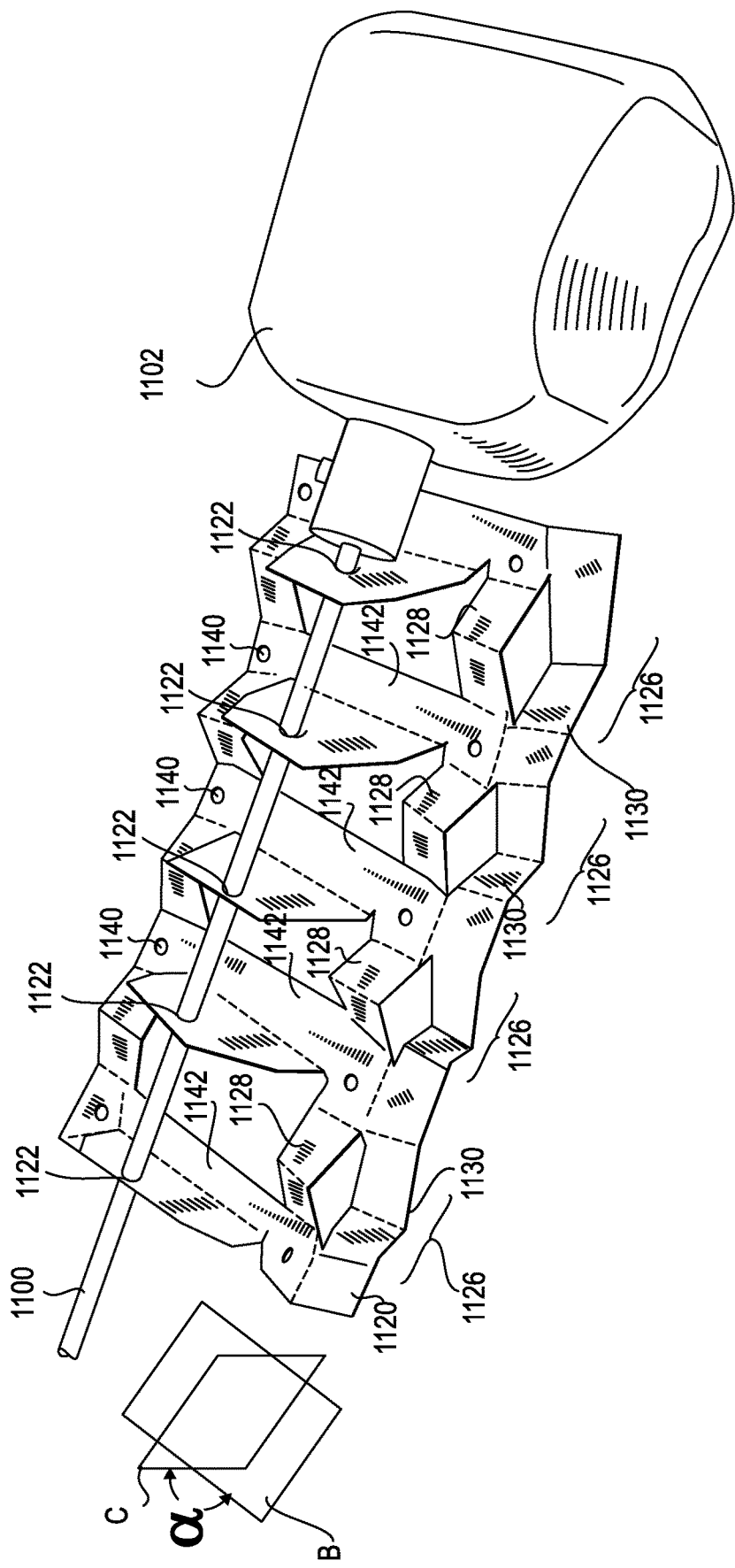
FIG. 37 is a perspective view of an exemplary anti-buckling mechanism positioned to provide anti-buckling support to an exemplary elongate member, which in turn is connected to a splayer, according to one embodiment.
Figure 38:
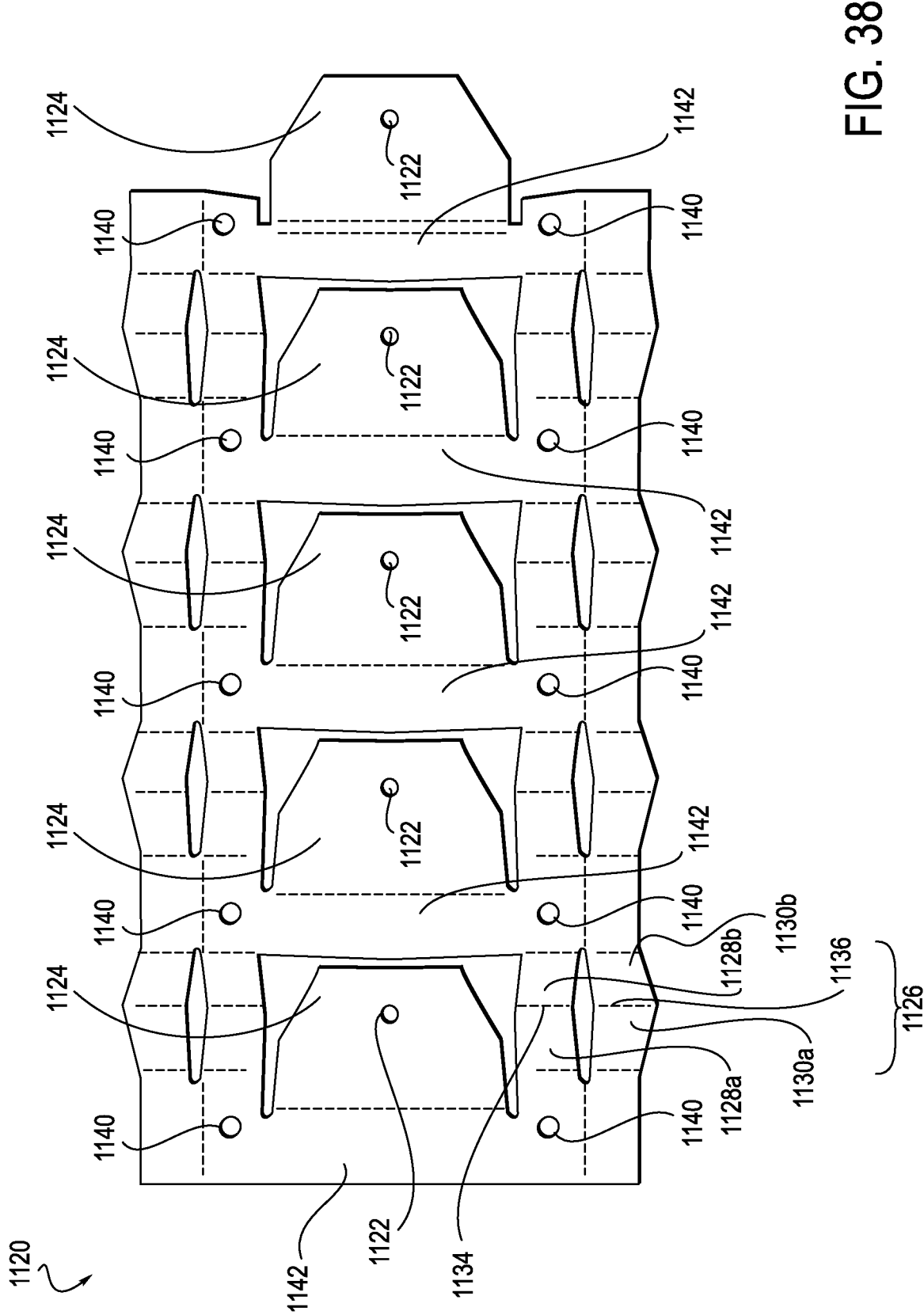
FIG. 38 is a top view of the exemplary anti-buckling mechanism of FIG. 37, illustrated without the elongate member and splayer.
Figure 39:
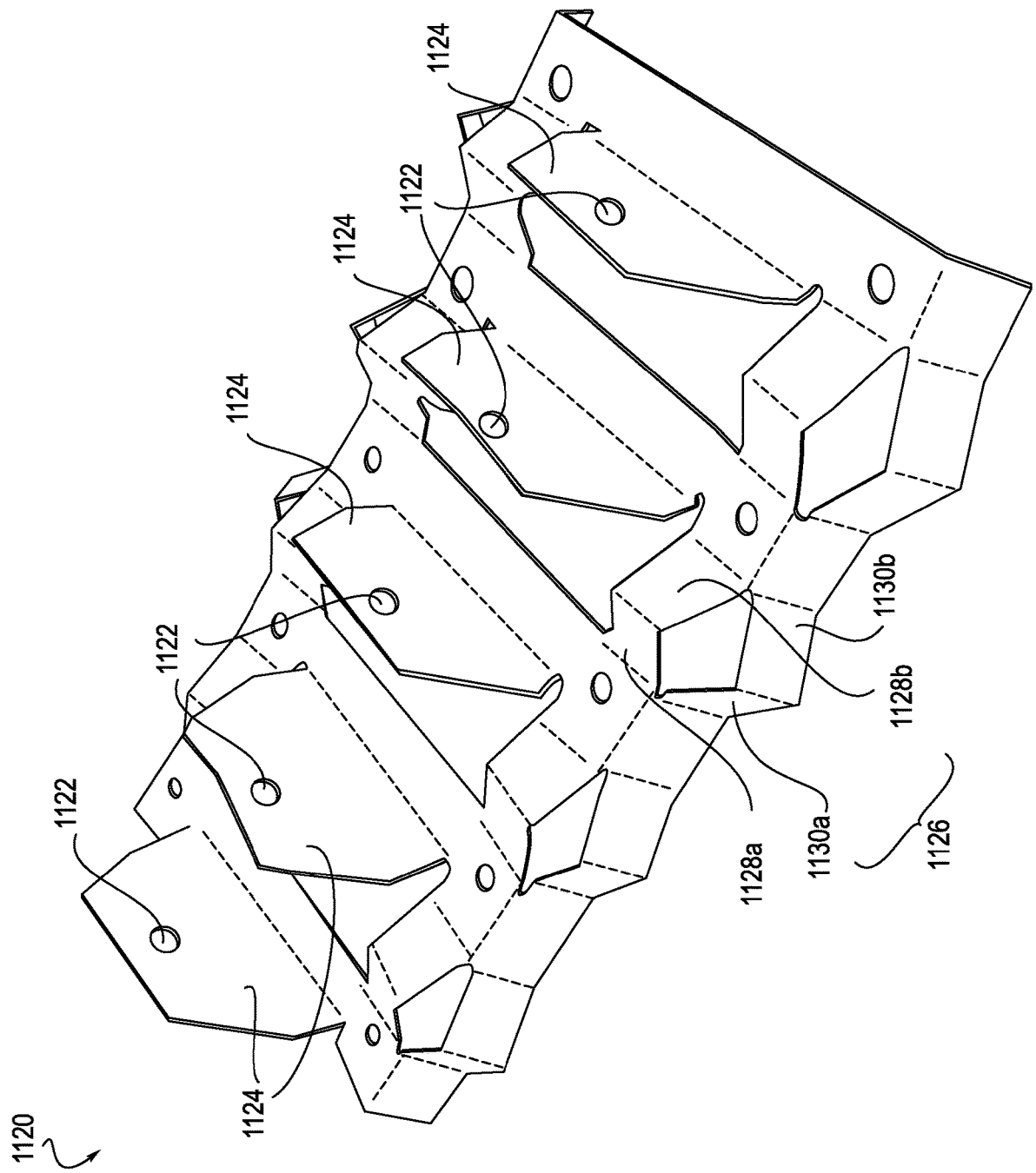
FIG. 39 is a perspective view of the exemplary anti-buckling mechanism of FIGS. 37 and 37, illustrated without the elongate member and splayer.

Turning now to FIGS. 37-39, another exemplary arrangement of an anti-buckling mechanism 1120 is described in detail. Anti-buckling mechanism 1120 may be a generally one-piece, foldable structure that selectively extends and retracts to reduce, inhibit, or prevent buckling of an elongate member 300, for example a catheter or sheath. As noted above, the elongate member 1100 may be actuated by a splayer 1102.

Anti-buckling mechanism 1120 may be formed from a plastic material, for example similar to material commonly employed as a sterile barrier (not shown) or any other type of flexible metal or polymer known to one skilled in the art. The anti-buckling mechanism 1120 may initially be formed of a monolithic single piece that is subsequently folded and/or cut to provide an extensible support structure. More specifically, the anti-buckling mechanism 1120 may be formed of material that can be cut and formed to create multiple eyelets 1122 to support the elongate member 1100. The material thickness can vary depending on the design requirement. Thicker materials will increase overall rigidity to better resist buckling but the thicker materials, when fully compressed, will occupy more space on the catheter or sheath. The eyelets 1122 could be molded or heat-formed into a funnel shape to provide low friction bushings configured to receive the elongate member 1100. The eyelets 1122 may be formed in a support 1124. An accordion section 1126 allowing the distance between the eyelet supports 1124 to expand or contract may be positioned between each eyelet support 1124. The model shown in FIGS. 37-39 generally incorporates accordion sections 1128, 1130 in two planes on either side of the eyelets. The provision of accordion sections 1128, 1130 in two separate planes may provide additional bi-directional stability that in turn increases the lateral rigidity of the elongate member 1100, thereby reducing the probability of buckling of the elongate member. More specifically, the accordion section 1128, as shown in FIG. 37, may generally be aligned in a first plane B while the accordion section 1130 is aligned in a second plane C. In one example, the planes B, C may be generally perpendicular to one another, however the planes B, C may define any non-zero angle α there between that is convenient, as shown in FIG. 37. Each according section 1128, 1130 may include two members 1128*a*, 1128*b*, and 1130*a*, 1130*b*, respectively, as show in FIG. 38. The members 1128*a* and 1128*b* may be hinged along a fold line 1134, while the members 1130*a* and 1130*b* are hinged along a fold line 1136, as shown in FIG. 38.

The anti-buckling mechanism may be generally disposable, and may mount to multiple locations on the RCM through a sterile drape (not shown in FIGS. 37-39). The RCM may drive each of the eyelet supports 1124, each second eyelet support 1124, or each third eyelet support 1124, depending on the density of eyelet supports 1124 and corresponding eyelets 1122, the density of the mini-carriages, and the anti-buckling stability of the accordion feature. For example, the anti-buckling mechanism 1120 may be used in conjunction with the support risers discussed above in relation to FIGS. 27-36, in place of or in addition to the scissor-like anti-buckling mechanism positioned within the RCM. In this manner, the anti-buckling support 1120 may be optimized to provide a desired level of anti-buckling support and axial stiffness.

In some examples, the anti-buckling mechanism 1120 advantageously may be formed of a plastic material or other material capable of being formed of a generally single, monolithic piece that is subsequently cut, folded, molded etc. to form the general configuration illustrated in FIGS. 38 and 39. In such examples, the anti-buckling mechanism 1120 may advantageously be formed using injection molding or other relatively inexpensive methods. Accordingly, costs of producing the anti-buckling mechanism 1120 may be reduced compared with traditional methods of manufacturing anti-buckling supports, and thus even where the anti-buckling mechanism 1120 is within a sterile field associated with a surgical procedure requiring disposal at the conclusion of the procedure, overall system costs may be reduced.

Referring now to FIG. 37, an exemplary anti-buckling mechanism is shown mounted to an elongate member 1100, for example a catheter. The anti-buckling support 1120 may be pre-attached to a sterile drape (not shown) if associated sheath and guide splayers are shipped separately and installed separately on the RCM. Alternatively, the anti-buckling support 1120 may be shipped as a separate unit or shipped pre-attached to the catheter and/or sheath.

The eyelet supports 1124 may be formed perpendicular to horizontal supports 1142 which extend laterally with respect to the elongate member 1100, as shown in FIG. 38. Additionally, the horizontal supports 1142 may include stiffening ribs (not shown), for example to increase an overall stiffness of the anti-buckling support 1120 in axial and/or lateral directions with respect to the elongate member 1100. The eyelets 1122 may themselves be heat-formed, for example in a two-sided funnel shape, to aide installation of the elongate member 1100, and reduce friction in both directions with the elongate member 1100. The accordion sections 1128, 1130 may also be designed to provide a proper living hinge spring force. For example, spring force provided by the hinges defined by fold lines 1134, 1136, as shown in FIG. 38, may be adjusted by perforating or thinning the material of the anti-buckling support 1120.

The accordion sections 1128, 1130 may extend between mounting locations 1140, as shown in FIG. 38. Two mounting locations 1140 may be disposed on either side of horizontal supports 1142, which extend laterally with respect to the elongate member 1100. The mounting locations 1140 may be provided to generally facilitate mounting the anti-buckling mechanism 1120 to RCM support risers (not shown in FIGS. 37-39) as discussed above in accordance with FIGS. 27-36. In one example, the mounting locations may generally snap into position on an RCM through the sterile drape, for example similar to sterile adapters (not shown) for snapping into guide and sheath carriages. Alternatively, a mechanism utilizing screws may couple the anti-buckling mechanism to the RCM.

The anti-buckling support 1120 may be folded and heat staked to retain its shape. The accordion sections 1128, 1130 generally provide "legs" on either side, which generally buckle axially. At the same time, lateral support is generally provided by the horizontal supports 1142. In the example shown, buckling would occur in the two planes B, C on either side of the elongate member 1100. The two-plane configuration may generally provide more support to constrain the catheter shaft from buckling.

Turning now to FIG. 40, a schematic illustration of an exemplary anti-buckling support is provided, which generally illustrates components of an exemplary anti-buckling support in the abstract, which may be generally applied to a representative catheter system (not shown in FIG. 40). The anti-buckling support 4100 includes a base plate 4102 and a rail 4104, which extends away from the base plate 4102. The base plate 4102 may support a splayer or other instrument driving apparatus (not shown) configured to facilitate control of an elongate member (not shown in FIG. 40) supported by the anti-buckling mechanism 4100. The rail 4104 may be fixed to the base plate 4102. The rail 4104 carries a multiple member supports 4106, which are moveable along the rail 4104. Each of the member supports 4106 define an eyelet 4108, which is configured to support the elongate member (not shown in FIG. 40). The elongate member may be snapped into the open eyelet 4108 through a sterile drape. This allows the entire anti-buckling support structure 4100 to remain outside of the sterile field. More specifically, when the elongate member inside the sterile field is snapped into place, each eyelet 4108 may generally prevent lateral movement of the elongate member relative to the rail 4104. As insertion of the elongate member may generally be driving in a direction parallel to the rail 4104, the moveable member supports 4106 may generally reduce buckling of the elongate member by preventing or minimizing lateral movement of the elongate member.

Axial movement of the member supports 4106 may be dictated by movement of the elongate member, for example each member support 4106 may be fixed axially to the elongate member and move passively with the elongate member during insertion. Alternatively, the member supports 4106 may be separately driven. In either case, accordion members 4110a, 4110b (collectively, 4110) may be provided which may bias movement of the member supports 4106 and provide additional lateral support for the elongate member. More specifically, each member support 4106 may be connected to an adjacent member support 4106 by a first accordion support 4110a and a second accordion support 4110b. The first and second accordion supports 4110a, 4110b are linked via a hinge 4112. The stiffness of hinge 4112 can be adjusted as required. Stiffer hinges will require more axial force to compress them but will serve to keep each of the member supports 4106 equidistant as the elongate member is advanced and the entire support structure 4100 is compressed axially Channel-Based Anti-Buckling Mechanisms Referring now to FIGS. 41 and 42, an exemplary illustration of a support assembly 4200 for supporting an elongate member 4202 is shown. The support assembly 4200 generally includes one or more rails, which provide anti-buckling support to the elongate member 4202. As will be described further below, in some exemplary illustrations an elongate member 4202 is supported by a generally single rail, while in other exemplary approaches multiple rail sections may be employed.

In one exemplary illustration, the elongate member 4202 may include a catheter sheath and leader catheter supported by corresponding rail sections. For example, in the exemplary approach shown in FIGS. 41-45, two rails 4204, 4214 are provided to support a catheter leader and a sheath catheter, respectively. More specifically, a leader rail 4204 may extend from a distal end 4206 of a leader splayer 4208 to a proximal end 4210 of a sheath splayer 4212. The leader rail 4204 generally defines a channel, as will be described further below, which laterally supports a catheter leader included in the elongate member 4202. A sheath rail 4214 protrudes from a distal end 4216 of a sheath splayer 4212, and similarly defines a channel, as will be described further below, which laterally supports a sheath catheter included in the elongate member 4202. The sheath splayer 4212 and leader splayer 4208 may include a sheath rail mount 4218 and a leader rail mount 4220, respectively, which allow the sheath splayer 4212 and leader splayer 4208 to translate along their respective rails 4214 and 4204. The sheath rail mount 4218 and leader rail mount 4220 may generally secure the sheath rail 4214 to the sheath splayer 4212 and the leader rail 4204 to the leader splayer 4208, respectively. The leader rail 4204 and sheath rail 4214 may be configured to allow for the elongate member 4202 to be slideably held within the rails 4204 and 4214. For example, the sheath splayer 4212 and leader splayer 4208 may insert and/or rotate a catheter sheath and leader catheter, respectively, of the elongate member 4202. Accordingly, the catheter sheath and leader may travel axially along the sheath rail 4214 and leader rail 4204, respectively.

Support assembly 4200 may further include a first roller assembly 4222 (or leader roller assembly) and a second roller assembly 4224 (or sheath roller assembly). The support assembly 4200 may also include a leader curtain 4226 and a sheath curtain 4228. The leader roller 4222 may selectively roll up the leader curtain 4226 and the sheath roller 4224 may selectively roll up the sheath curtain 4228, respectively. The curtains 4226, 4228 may be used to prevent the elongate member 4202 from buckling and/or being dislodged or otherwise removed from the channels of the rails 4204, 4214, respectively, as will be described further below.

The sheath rail 4214 may extend from the sheath splayer 4212 to a patient insertion site (not shown). More specifically, a proximal end 4232 of the sheath rail 4214 may be coupled to the distal end 4216 of the sheath splayer 4212 and the distal end 4234 of the sheath rail 4214 may be coupled to or otherwise be disposed adjacent the patient insertion site. In one exemplary approach, the distal end 4234 of the sheath rail 4214 may be fixed to the patient insertion site using a coupling device, such as a flexible nylon strap or a stabilizer. The coupling device or strap may be attached to a patient patch (not shown), which may in turn be adhesively secured to the patient. In other exemplary illustrations, other coupling devices may be employed to secure the distal end 4234 of the sheath rail 4214 near the patient insertion site.

Referring to FIG. 42, a cross-sectional view of an exemplary leader rail 4204 and/or sheath rail 4214 is shown with a semi-circular catheter channel 4240 and a rectangular rail mount channel 4242. Both the leader rail 4204 and sheath rail 4214 may have a similar configuration to that shown in FIG. 42, although the leader rail 4204 may define relatively smaller interior dimensions consistent with the smaller size of the leader catheter in comparison to the sheath catheter. While the channels 4240, 4242 are shown as semi-circular and rectangular, respectively, any shape or configuration may be employed that is convenient, for example the channels may be sized and shaped to receive an elongate member. The elongate member 4202 may be disposed within the catheter channel 4240 such that the central axis of the elongate member 4202 coincides with the center axis of the catheter channel 4240 and/or the center of the semi-circular shape of the catheter channel 4240. The catheter channel 4240 may be sized to receive the elongate member 4202 holding it sufficiently secure while providing enough clearance to allow it to slide within the catheter channel 4240 with minimal friction. Accordingly, the catheter channel 4240 generally provides lateral support to the elongate member 4202, thereby preventing buckling of the elongate member 4202, while also allowing axial movement of the elongate member 4202 to permit insertion and retraction. The catheter channel 4240 of the leader rail 4204 may be sized smaller than the catheter channel 4240 of the sheath rail 4214 to accommodate a smaller diameter leader catheter (in comparison to the sheath catheter).

Figure 43:
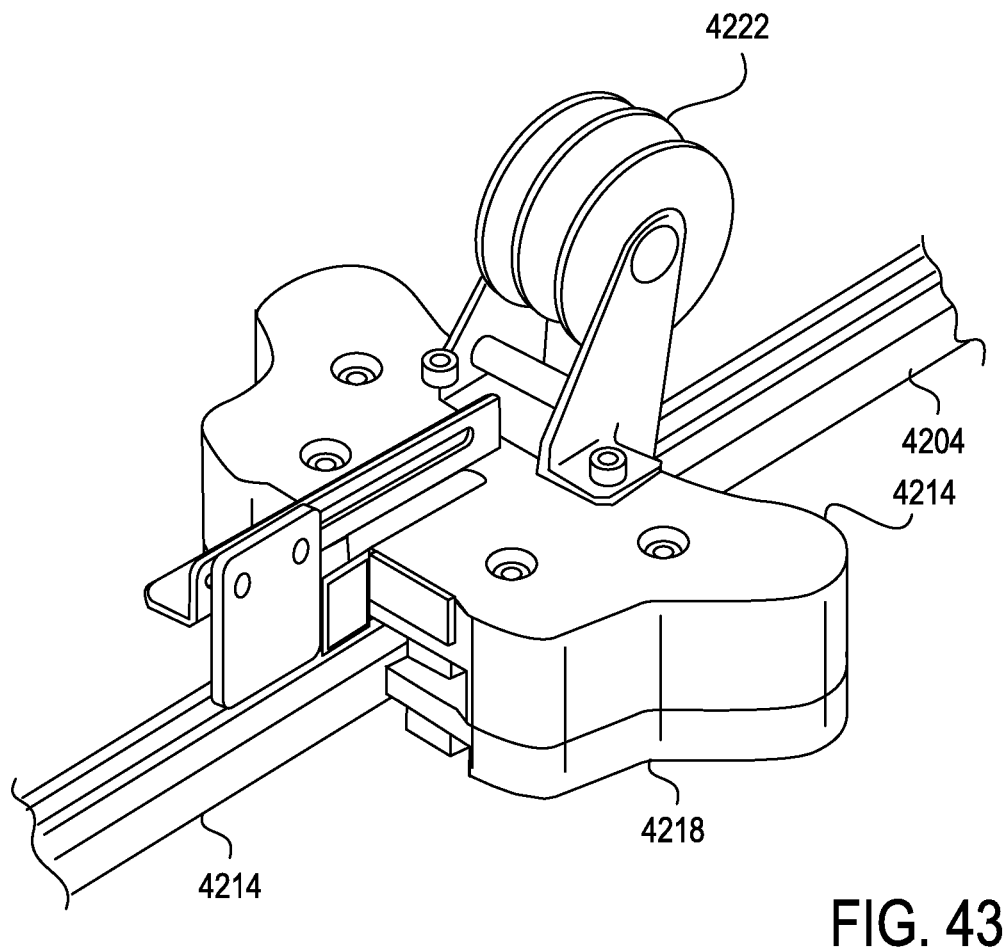
FIG. 43 is a perspective view of the sheath splayer of FIG. 42, including a rear roller assembly, according to one embodiment.
Figure 45:
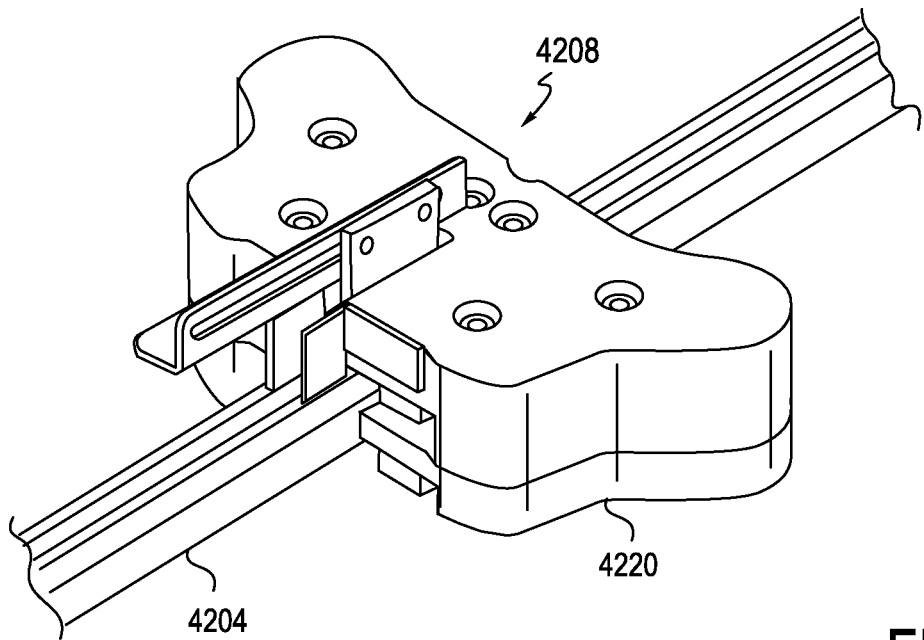
FIG. 45 is an enlarged perspective view of the leader splayer and leader rail mount, according to one embodiment.

Referring now to FIG. 43, an enlarged view of the sheath splayer 4212 is shown. The rail mount channel 4242 (not shown in FIG. 43) of the sheath rail 4214 may couple the sheath rail 4214 to the sheath rail mount 4218 and allow the sheath splayer 4212 to translate axially along the sheath rail 4214. The sheath rail mount 4218 not only couples the sheath splayer 4212 to the sheath rail 4214 but may enclose the elongate member 4202 in place in all radial directions. As shown in FIG. 45, an exemplary leader splayer 4208 and leader rail mount 4220 may be similar in construction to sheath splayer 4212 and the sheath rail mount 4218, and may support the leader catheter in a similar manner to the support provided to a leader catheter by the sheath splayer 4212 and sheath rail mount 4218. Moreover, the leader rail 4204 may be coupled to the leader rail mount 4220 to allow the leader splayer 4208 to translate axially along the leader rail 4204.

The elongate member 4202, for example the leader catheter and/or catheter sheath, may be held within the catheter channel 4240 by the sheath rail mount 4218 or the leader rail mount 4220, however the remaining length of the elongate member 4202 may still be free to move in a vertical direction which might result in unwanted buckling of the elongate member 4202 during catheter insertion.

In order to prevent this vertical buckling, a leader curtain 4226 and a sheath curtain 4228, as shown in FIG. 41, may be provided to enclose the catheter channel 4240 along the length of the leader rail 4204 and the sheath rail 4214, respectively, as will be described further below. The leader curtain 4226 and sheath curtain 4228 may each be selectively inserted into the leader rail 4204 and sheath rail 4214, respectively, to provide further anti-buckling support to the elongate member 4202 disposed in the rails 4204 and 4214. Additionally, as will be described further below, the curtains 4226, 4228 may each be generally rolled up on a mount adjacent their respective rails 4214, 4204 to allow for selective deployment of the curtains 4226, 4228 along the rails 4214, 4204.

Figure 44:
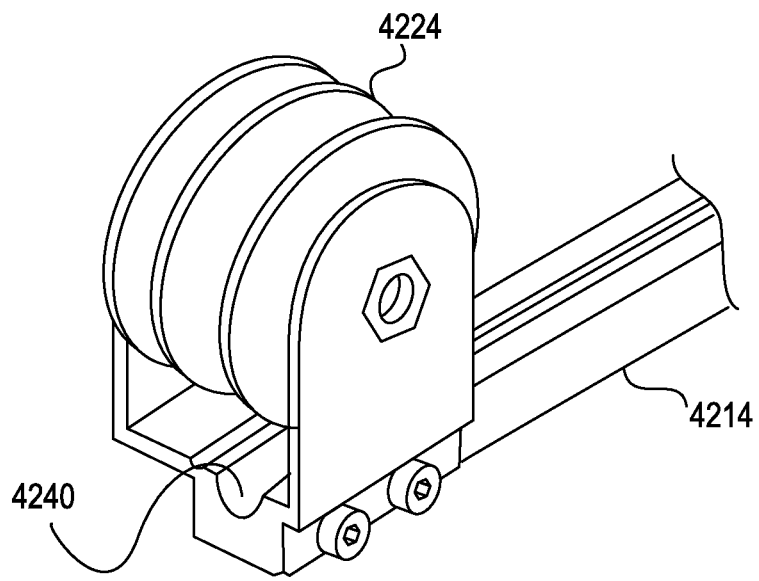
FIG. 44 is a perspective view of a roller assembly mounted to a sheath rail, according to one embodiment.

In one example, the curtains 4226, 4228 may be mounted at distal ends of the rails 4214, 4204, respectively. More specifically, referring now to FIGS. 43 and 44, in one exemplary illustration, a first roller assembly 4222 for rolling up the leader curtain 4226 and a second roller assembly 4224 for rolling up the sheath curtain 4228 are provided. The first roller assembly 4222 may be mounted to the sheath splayer 4212, as shown in FIG. 43, and the second roller assembly 4224 may be mounted to the sheath rail 4214, as shown in FIG. 44. The first roller assembly 4222 may be configured to roll up the leader curtain 4226 as the leader splayer 4208 moves toward the sheath splayer 4212. The second roller assembly 4224 may be configured to roll up the sheath curtain 4228 as the sheath splayer 4212 moves toward the distal end of the sheath rail. The leader curtain 4226 and/or the sheath curtain 4228 may be contained within the rail mount channel 4242 of their respective rails 4204, 4214.

Figure 46:
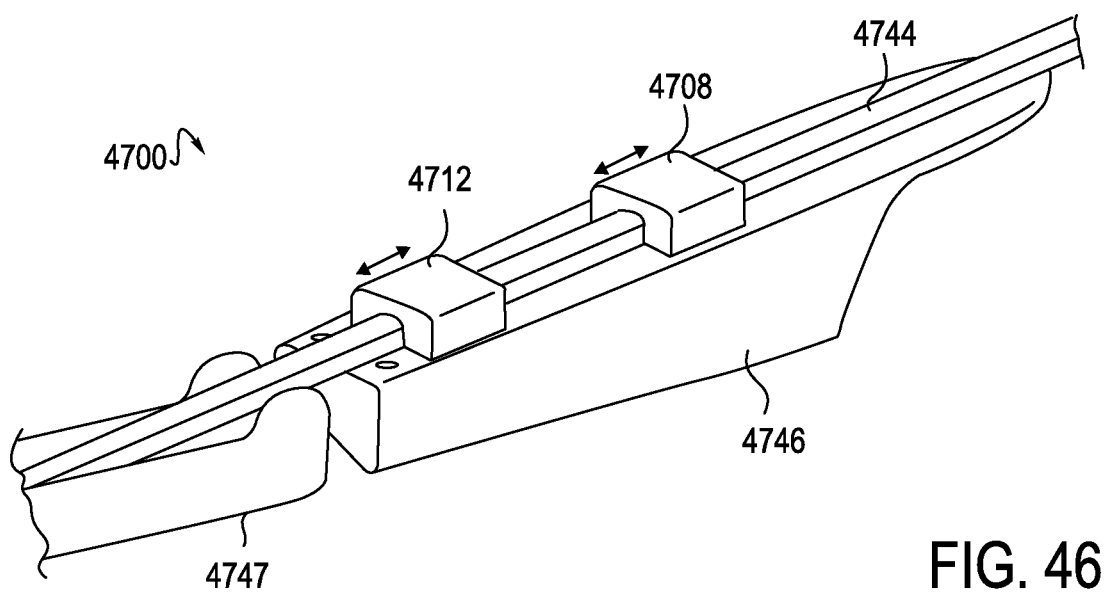
FIG. 46 is a perspective view of another exemplary anti-buckling mechanism, including a long channel extending between a leader splayer and a sheath splayer, according to one embodiment.

FIG. 46 shows another exemplary channel type anti-buckling mechanism 4700. This variation includes a relatively long channel 4744 positioned above a sterile drape 4746, with both leader splayer 4708 and sheath splayer 4712 extending through the sterile drape 4746. The long channel 4744 is generally a single continuous rail, in contrast to other approaches using two separate rails. Accordingly, the channel 4744 of the mechanism 4700 extends as a generally single, monolithic piece through both the leader splayer 4708 and sheath splayer 4712. The channel 4744 may passively support the elongate member 4202. For example, the channel 4744 may remain in a fixed position with respect to a patient 4747 (not shown in FIG. 46). Accordingly, in such examples the elongate member 4202 may move axially with respect to the channel 4744 as the elongate member 4202 is inserted into or retracted out of the patient 4747. In other approaches, the channel 4744 may be selectively moveable, for example in coordination with the elongate member 4202.

Figure 47A:
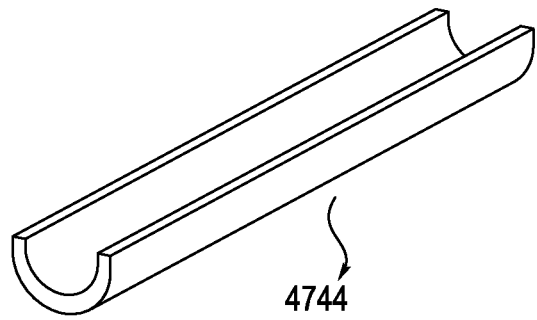
FIGS. 47A and 47B are perspective and end-on cross-sectional views, respectively, of another exemplary anti-buckling mechanism, including a long channel extending between a leader splayer and a sheath splayer, and FIG. 47B further shows an exemplary elongate member installed, according to one embodiment.
Figure 47B:
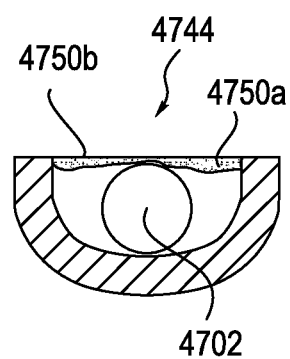

FIGS. 47A and 47B are perspective and end-on cross-sectional views, respectively, of an alternative embodiment of channel 4744. FIG. 47B the channel 4744 with an elongate member 4702, for example a catheter, installed. While not specifically shown in FIGS. 46, 47A, and 47B, the channel 4744 may be provided with one or more curtains for providing vertical anti-buckling support to an elongate member 4702 in substantially a similar manner as that described above regarding support assembly 4200.

In some exemplary approaches, a split cover may be used to prevent egress of an elongate member from an exemplary rail or channel. For example, as shown in FIG. 47B, a split cover 4750a, 4750b is provided along an upper open end of the channel 4744. The split cover generally prevents an elongate member 4702 disposed within the channel 4744 from buckling vertically, for example in a manner in which some portion of the elongate member 4702 would become dislodged from the generally U-shaped interior of the channel 4744. The two sections of the cover 4750a, 4750b may generally be compliant to allow insertion and/or retraction of the elongate member 4702 into the channel 4744, while also being sufficiently stiff to resist buckling of the elongate member 4702 when it is contained within the channel 4744.

Figure 48:
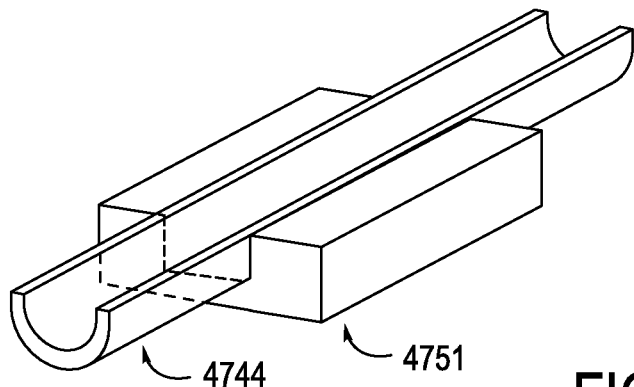
FIG. 48 is a perspective view of an exemplary sterile drape adapter that is coupled to the long channel of FIGS. 47A and 47B, according to one embodiment.

Referring now to FIG. 48, an exemplary support mechanism 4700 may also include a sterile adaptor 4751 coupled to the channel 4744. The sterile adaptor 4751 may be coupled via gears (not shown), which may drive the sterile adaptor 4751 along the channel 4744. In this manner, the sterile adaptor 4751 may be moved along the channel 4744, for example to drive insertion and/or retraction of an elongate member. The leader splayer or the sheath splayer may be mounted to the sterile adaptor 4751. The sterile adaptor 4751 may generally be disposed on an upper side of the channel 4744 and underneath a splayer (not shown in FIG. 48). In some embodiments, the sterile adaptor 4751 may be coupled to a sterile drape (not shown in FIG. 48) that covers a remaining portion of the robotic catheter system and generally provides a barrier between the robotic catheter system and the sterile field.

Turning now to FIGS. 49A and 49B, an exemplary support assembly is illustrated. The support assembly may include a sheath splayer 4708 and a leader splayer 4709, each of which is mounted to the channel 4744. The catheter splayer 4708 may include jaws (not shown), which selectively engage the channel 4744, thereby selectively fixing the sheath splayer 4708 to the channel 4744. More specifically, the jaws may allow selective fixing of the channel 4744 to a splayer, temporarily preventing axial translation of the splayer along the channel 4744. The sheath splayer 4708 may otherwise be axially movable with respect to the channel 4744.

Additionally, the splayer 4708 may move axially with respect to the leader catheter 4760b, which extends from the leader splayer 4709. More specifically, as the splayer 4708 moves along the channel 4744 and the elongate member 4760b, the elongate member 4760b is generally taken up out of the channel 4744 by the sheath splayer 4708 and placed back into the channel 4744. In this fashion, the elongate member 4760b generally remains supported within the channel 4744 save for the portion of the elongate member 4760b that is disposed within the sheath splayer 4708.

The channel 4744 may have a cover for selectively enclosing the elongate member 4760a and/or 4760b within the channel 4744. For example, the channel 4744 may include a split top, or the channel 4744 may have a roll up cover similar to that described above. The cover may generally facilitate movement of the catheter leader 4760b out of and back into the channel 4744 during axial movement of the sheath splayer 4708 with respect to the channel 4744 and catheter leader 4760b.

The exemplary rail systems described herein, for example the rails 4204 and/or 4214, as well as the long channel 4744, generally minimize wasted length of a catheter system, especially in comparison to folding support mechanisms. More specifically, a comparable folding or scissor type support mechanism necessarily takes up at least some axial space even when fully compressed, resulting in some length of the elongate member or catheter that must remain outside the patient. By comparison, a splayer slidably mounted on one of the exemplary rails described herein, for example splayer 4218, can translate axially up to the patient insertion site along the rail 4214, leaving a minimal amount of space, if any, in between the splayer and the patient insertion site.

The mechanisms and methods described herein have broad applications. The foregoing embodiments were chosen and described in order to illustrate principles of the methods and apparatuses, as well as some practical applications. The preceding description enables others skilled in the art to use methods and apparatuses in various embodiments and with various modifications, as suited to the particular use contemplated. In accordance with the provisions of the patent statutes, the principles and modes of operation of this disclosure have been explained and illustrated in exemplary embodiments.

It is intended that the scope of the present methods and apparatuses be defined by the following claims. This disclosure may be practiced otherwise than is specifically explained and illustrated, without departing from its spirit or scope. Various alternatives to the embodiments described herein may be employed in practicing the claims, without departing from the spirit and scope as defined in the following claims. The scope of the disclosure should be determined, not with reference to the above description, but should instead be determined with reference to the appended claims, along with the full scope of equivalents to which such claims are entitled.

Future developments may occur in the arts discussed herein, and the disclosed systems and methods may be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. The following claims define the scope of the invention and that the method and apparatus within the scope of these claims and their equivalents be covered thereby. In sum, the invention is capable of modification and variation and is limited only by the following claims.

What is claimed is:

1. A device for preventing buckling of a flexible elongate member during insertion of the flexible elongate member, the device comprising:
   a support frame comprising a first end, a second end, and multiple pairs of support members, wherein the support frame is configured to reversibly move from a collapsed configuration to an expanded configuration when the first and second ends are moved away from each other; and multiple open channels coupled to the multiple pairs of support members of the support frame, wherein the multiple open channels each comprise a top opening at a top of each of the multiple open channels that is configured to allow the flexible elongate member to be top loaded into the top opening of each of the multiple open channels such that the flexible member is delivered into the multiple open channels in a direction that is transverse to a longitudinal axis that extends through the multiple open channels, and wherein the multiple open channels are maintained in an axial alignment as the support frame is moved between the expanded and collapsed configurations.

2. The device of claim 1, wherein the support frame comprises an alignment member.

3. The device of claim 2, wherein the alignment member defines one of the multiple open channels.

4. The device of claim 2, wherein the alignment member includes a slidable closure member configured to slide laterally with respect to the multiple open channels to close or open the multiple open channels.

5. The device of claim 1, wherein each of the multiple open channels is secured to one of the pairs of support members, such that each open channel is maintained in a substantially fixed rotational position with respect to its corresponding pair of support members.

6. The device of claim 1, further comprising the flexible elongate member, wherein each of the multiple open channels has a diameter that is larger than an outer diameter of the flexible elongate member.

7. The device of claim 1, further comprising at least one closure member configured to selectively cover one of the multiple open channels.

8. The device of claim 7, wherein the at least one closure member is slidably connected to the one of the multiple open channels.

9. The device of claim 8, further comprising multiple alignment members, each defining one of the multiple open channels, wherein the at least one closure member is configured to slide laterally with respect to the one of the multiple open channels.

10. The device of claim 1, wherein a diameter of each of the multiple open channels is sufficiently larger than a diameter of the flexible elongate member to allow the elongate member to maintain the axial alignment when the first and second ends are moved with respect to each other.

11. The device of claim 1, further comprising a first coupler positioned on the first end of the support frame, and a second coupler positioned on the second end of the support frame, wherein the second coupler is configured to position the flexible elongate member.

12. The device of claim 1, wherein the multiple open channels each comprise an open perimeter for receiving the flexible elongate member therein.

* * * * *

UNITED STATES PATENT AND TRADEMARK OFFICE
CERTIFICATE OF CORRECTION

PATENT NO. : 10,569,052 B2  
APPLICATION NO. : 14/713895  
DATED : February 25, 2020  
INVENTOR(S) : Arkady Kokish Page 1 of 1

It is certified that error appears in the above-identified patent and that said Letters Patent is hereby corrected as shown below:

In the Claims

In Column 25, Line 10 (Approx.), Claim 1, delete "flexible member" and insert --flexible elongate member--.

Signed and Sealed this  
Nineteenth Day of May, 2020

Andrei Iancu  
*Director of the United States Patent and Trademark Office*